United States Patent
Frank et al.

(10) Patent No.: US 7,981,883 B2
(45) Date of Patent: Jul. 19, 2011

(54) SUBSTITUTED SPIRO-COMPOUNDS AND THE USE THEREOF FOR PRODUCING MEDICAMENTS

(75) Inventors: Robert Frank, Aachen (DE); Ruth Jostock, Stolberg (DE); Melanie Reich, Aachen (DE); Gregor Bahrenberg, Aachen (DE); Hans Schick, Berlin (DE); Helmut Sonnenschein, Berlin (DE)

(73) Assignee: Gruenenthal GmbH, Aachen (DE)

( * ) Notice: Subject to any disclaimer, the term of this patent is extended or adjusted under 35 U.S.C. 154(b) by 371 days.

(21) Appl. No.: 11/914,821

(22) PCT Filed: May 17, 2006

(86) PCT No.: PCT/EP2006/004653
§ 371 (c)(1),
(2), (4) Date: Mar. 19, 2008

(87) PCT Pub. No.: WO2006/136245
PCT Pub. Date: Dec. 28, 2006

(65) Prior Publication Data
US 2009/0275628 A1 Nov. 5, 2009

(30) Foreign Application Priority Data

May 19, 2005 (DE) .......................... 10 2005 023 779
Sep. 20, 2005 (DE) .......................... 10 2005 044 814

(51) Int. Cl.
*A61K 31/551* (2006.01)
*A61K 31/496* (2006.01)
*A61K 31/4725* (2006.01)
*A61K 31/42* (2006.01)
*C07D 243/08* (2006.01)
*C07D 413/14* (2006.01)
*C07D 217/22* (2006.01)
*C07D 261/04* (2006.01)

(52) U.S. Cl. .................. 514/218; 514/254.04; 514/310; 514/378; 540/575; 544/369; 546/143; 548/240

(58) Field of Classification Search .................. 514/379; 548/241
See application file for complete search history.

(56) References Cited

U.S. PATENT DOCUMENTS

| 2007/0043023 A1* | 2/2007 | Makings et al. ......... 514/212.02 |
| 2007/0208001 A1* | 9/2007 | Zhuo et al. ............... 514/212.02 |

FOREIGN PATENT DOCUMENTS

| WO | WO 98/43962 A1 | 10/1998 |
| WO | WO 2005/021515 A2 | 3/2005 |

OTHER PUBLICATIONS

Vippagunta et al., Crystalline solids, 2001, Advanced Drug Delivery Reviews, 48, pp. 3 and 18.*
Coderre et al., "Contribution of central neuroplasticity to pathological pain: review of clinical and experimental evidence", Pain 52 (1993) 259-285, Elsevier Science Publishers B.V.
Hendershot et al., "Antagonism of the Frequency of Phenylquinone-Induced Writhing in the Mouse by Weak Analgesics and Nonanalgesics", vol. 125, pp. 237-240, The Biochemical Research Laboratory, The Dow Chemical Company, Midland, Michigan, Received for publication Sep. 19, 1958.
Form PCT/IB/338 and Form PCT/IPEA/409 (twelve (12) pages), 2007.
Harshad K. Rami, et al., "The therapeutic potential of TRPVI (VRI) antagonists: clinical answers await", Drug Discovery Today: Therapeutic Strategies, 2004, pp. 97-104, vol. 1, No. 1.
Carlo Alberto Maggi, "Therapeutic Potential of Capsaicin-like Molecules", Therapeutic Potential of Capsaicin-Like Molecules: Studies in Animals and Humans, Life Sciences, 1992, pp. 1777-1781, vol. 51, No. 23.
L. A. Birder, et al., "Altered urinary bladder function in mice lacking the vanilloid receptor TRPV1", Nature Neuroscience, Sep. 2002, pp. 856-860, vol. 5, No. 9.

\* cited by examiner

*Primary Examiner* — Kamal Saeed
*Assistant Examiner* — Kristin Bianchi
(74) *Attorney, Agent, or Firm* — Crowell & Moring LLP

(57) ABSTRACT

The present invention relates to substituted spiro compounds, to processes for preparing them, to medicaments comprising these compounds and to the use of these compounds for producing medicaments.

25 Claims, No Drawings

SUBSTITUTED SPIRO-COMPOUNDS AND THE USE THEREOF FOR PRODUCING MEDICAMENTS

The present invention relates to substituted spiro compounds, to processes for preparing them, to medicaments comprising these compounds and to the use of these compounds for producing medicaments.

The treatment of pain, in particular of neuropathic pain, is of great importance in medicine. Effective pain therapies are in demand across the globe. The urgent need for action to provide patient-friendly and targeted treatment of chronic and non-chronic states of pain, meaning the successful and satisfactory treatment of the patient's pain, is also reflected in the large number of scientific studies which have recently appeared in the field of applied analgesics or basic research in nociception.

A suitable starting point for the treatment of pain, in particular of neuropathic pain, is provided by the subtype 1 vanilloid receptor (VR1/TRPV1) which is often also referred to as a capsaicin receptor. This receptor is stimulated, inter alia, by vanilloids, such as for example capsaicin, heat and protons and plays a central role in the production of pain. In addition, it is important for a large number of further physiological and pathophysiological processes such as, for example, migraine; depression; neurodegenerative diseases; cognitive diseases; panic attacks; epilepsy; coughing; diarrhea; pruritus; disturbances of the cardiovascular system; eating disorders; medication dependency; medication abuse and in particular urinary incontinence.

An object of the present invention was therefore to provide new compounds which are suitable, in particular, as pharmacological active ingredients in medicaments, preferably in medicaments for the treatment of disturbances or diseases which are transmitted, at least in some cases, by vanilloid receptors 1 (VR1/TRPV1 receptors).

It has surprisingly been found that substituted spiro compounds of general formula I as indicated below are suitable for combating pain and display outstanding affinity to the subtype 1 vanilloid receptor (VR1/TRPV1 receptor) and are therefore suitable, in particular, for the prophylaxis and/or treatment of disturbances or diseases transmitted, at least in some cases, by vanilloid receptors 1 (VR1/TRPV1).

The present invention therefore relates to substituted spiro compounds of general formula I,

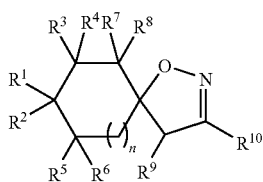

I wherein
n is equal to 0, 1 or 2,
I.)
$R^1$ represents a linear or branched, saturated or unsaturated, unsubstituted or at least singly substituted aliphatic radical optionally having at least one heteroatom as chain member;
    an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system;
    an unsubstituted or at least singly substituted aryl or heteroaryl radical which can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system;
    or a —C(=O)—$NR^{11}R^{12}$ group;
and
$R^2$, $R^3$, $R^4$, $R^5$, $R^6$, $R^7$ and $R^8$, independently of one another, each
    represent a hydrogen radical or
    a linear or branched, saturated or unsaturated, unsubstituted or at least singly substituted aliphatic radical optionally having at least one heteroatom as chain member;
or
II.)
$R^1$ and $R^3$ together represent a —$(CH_2)_p$ group wherein p=3, 4, 5 or 6;
and
$R^2$, $R^4$, $R^5$, $R^6$, $R^7$ and $R^8$, independently of one another, each
    represent a hydrogen radical
    or a linear or branched, saturated or unsaturated, unsubstituted or at least singly substituted aliphatic radical optionally having at least one heteroatom as chain member;
or
III.)
$R^1$, $R^2$, $R^7$ and $R^8$ each represent a hydrogen radical
and
$R^3$, $R^4$, $R^5$ and $R^6$, independently of one another, each
    represent a linear or branched, saturated or unsaturated, unsubstituted or at least singly substituted aliphatic radical optionally having at least one heteroatom as chain member;
and in each case
$R^9$ represents a hydrogen radical;
    a linear or branched, saturated or unsaturated, unsubstituted or at least singly substituted aliphatic radical optionally having at least one heteroatom as chain member;
    an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system;
    or an unsubstituted or at least singly substituted aryl or heteroaryl radical which can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system;
$R^{10}$ represents a linear or branched, saturated or unsaturated, unsubstituted or at least singly substituted aliphatic radical optionally having at least one heteroatom as chain member;
    an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system;

an unsubstituted or at least singly substituted phenyl radical, an unsubstituted or at least singly substituted phenyl radical which is condensed with an unsubstituted or at least singly substituted mono- or polycyclic ring system, an unsubstituted or at least singly substituted naphthyl or heteroaryl radical which can be condensed with an unsubstituted or at least singly substituted mono- or polycyclic ring system, an unsubstituted or at least singly substituted aryl or heteroaryl radical which is bound via a —(CH$_2$)—, —(CH$_2$)$_2$— or —(CH$_2$)$_3$ group and can optionally be condensed with an unsubstituted or at least singly substituted mono- or polycyclic ring system;

or a —C(=O)—NR$^{13}$R$^{14}$ group;

R$^{11}$ and R$^{13}$, independently of one another, each represent a linear or branched, saturated or unsaturated, unsubstituted or at least singly substituted aliphatic radical;

an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system;

or an unsubstituted or at least singly substituted aryl or heteroaryl radical which can be bound via a —(CH$_2$)—, —(CH$_2$)$_2$— or —(CH$_2$)$_3$ group and/or condensed with an unsubstituted or at least singly substituted mono- or polycyclic ring system;

R$^{12}$ and R$^{14}$, independently of one another, each represent a hydrogen radical;

a linear or branched, saturated or unsaturated, unsubstituted or at least singly substituted aliphatic radical;

an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system;

or an unsubstituted or at least singly substituted aryl or heteroaryl radical which can be bound via a —(CH$_2$) group and/or condensed with an unsubstituted or at least singly substituted mono- or polycyclic ring system;

or

R$^{11}$ and R$^{12}$ or R$^{13}$ and R$^{14}$ respectively form together with the nitrogen atom connecting them as ring member an unsubstituted or at least singly substituted, unsaturated or saturated heterocycloaliphatic radical which optionally has at least one further heteroatom as ring member and can be condensed with an unsubstituted or at least singly substituted mono- or polycyclic ring system;

wherein the substituents of the above-mentioned heterocycloaliphatic radical formed by R$^{11}$ and R$^{12}$ or R$^{13}$ and R$^{14}$ can be selected independently of one another from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—NH$_2$, —C(=O)—NH—C$_{1-5}$ alkyl, —C(=O)—N—(C$_{1-5}$ alkyl)$_2$, cyclohexyl, cyclopentyl, pyridinyl, pyridazinyl, pyrimidinyl, [1,2,5]-thiadiazolyl, thiazolyl, —(CH$_2$)-benzo[b]furanyl, —O-phenyl, —O-benzyl, phenyl and benzyl, wherein in each case the cyclic portion of the radicals pyrimidinyl, [1,2,5]-thiadiazolyl, thiazolyl, pyridinyl, cyclopentyl, cyclohexyl, pyridazinyl, —O-phenyl, —O-benzyl, phenyl, —(CH$_2$)-benzo[b]furanyl and benzyl can be substituted with substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl, and the substituents of the above-mentioned aliphatic radicals can be selected independently of one another from the group consisting of F, Cl, Br, I, —CN, —NO$_2$, —OH, —SH and —NH$_2$;

in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

Preferably, the radicals R$^{10}$, R$^{11}$, R$^{12}$, R$^{13}$ and R$^{14}$ have alkylene, alkenylene or alkinylene groups which can be respectively substituted with substituents selected independently of one another from the group consisting of F, Cl, Br, —OH, —SH, —NH$_2$, —CN, —NO$_2$ and phenyl; wherein the phenyl radical can be substituted with 1, 2, 3, 4 or 5 substituents selected independently of one another from the group consisting of methyl, ethyl, n-propyl, isopropyl, n-butyl, isobutyl, sec-butyl, tert-butyl, n-pentyl, isopentyl and neopentyl.

Preferably, the radical R$^{10}$, in any of the definitions indicated in the present document, can represent an unsubstituted or at least singly substituted phenyl radical, on the condition that not one of the meta positions and the para position of this phenyl radical are substituted with substituents which are respectively bound via an identical atom selected from the group consisting of oxygen, sulphur and nitrogen. This condition rules out the substituents mentioned in a corresponding position in document WO 2005/21515 A1.

Preferably, the radical R$^{10}$ can comprise a phenyl radical as defined above or an unsubstituted or at least singly substituted phenyl radical which is condensed with an unsubstituted or at least singly substituted mono- or polycyclic ring system, or represents an unsubstituted or at least singly substituted naphthyl or heteroaryl radical which can be condensed with an unsubstituted or at least singly substituted mono- or polycyclic ring system which is selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl; 2H-benzo[1.4]oxazin-3(4H)-onyl, (3,4)-dihydroquinolin-2(1H)-onyl,

[3,4]-dihydro-2H-1,4-benzoxazinyl and benzothiazolyl, wherein the radicals can be respectively unsubstituted or at least singly substituted.

Aliphatic radicals include in the sense of the present invention acyclic saturated or unsaturated hydrocarbon radicals which can be branched or straight chained and unsubstituted or singly substituted or multiply substituted by the same or different substituents, containing preferably 1 to 20 (i.e. 1, 2, 3, 4, 5, 6, 7, 8, 9, 10, 11, 12, 13, 14, 15, 16, 17, 18, 19 or 20), particularly preferably 1 to 12 (i.e. 1, 2, 3, 4, 5, 6, 7, 8, 9, 10, 11 or 12), most particularly preferably 1 to 6 (i.e. 1, 2, 3, 4, 5 or 6) carbon atoms, i.e. $C_{1-20}$, $C_{1-12}$, $C_{1-6}$ alkyls, $C_{2-20}$, $C_{2-12}$, $C_{2-6}$ alkenyls and $C_{2-20}$, $C_{2-12}$, $C_{2-6}$ alkinyls.

Alkenyls have at least one C—C double bond and alkinyls at least one C—C triple bond. Advantageously, aliphatic radicals can be selected from the group comprising methyl, ethyl, n-propyl, isopropyl, n-butyl, isobutyl, sec-butyl, tert-butyl, n-pentyl, isopentyl, neopentyl, n-hexyl, 2-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosanyl, ethenyl (vinyl), ethinyl, propenyl (—CH$_2$CH═CH$_2$, —CH═CH—CH$_3$, —C(═CH$_2$)—CH$_3$), 2-methylpropenyl, propinyl (—CH$_2$—C≡CH, —C≡C—CH$_3$), butenyl, butinyl, pentenyl, pentinyl, hexenyl, hexinyl, octenyl and octinyl.

The above-mentioned aliphatic radicals can preferably have 1, 2 or 3 heteroatoms selected from the group comprising oxygen, sulphur and nitrogen, i.e. —N(H)— and —N(C$_{1-6}$ alkyl).

Examples of aliphatic radicals having 1, 2 or 3 heteroatoms include —(CH$_2$)—(CH$_2$)—O—CH$_3$, —(CH$_2$)—(CH$_2$)—(CH$_2$)—O—CH$_3$, —(CH$_2$)—(CH$_2$)—(CH$_2$)—N(C$_2$H$_5$)—(C$_2$H$_5$), —(CH$_2$)—(CH$_2$)—S—CH$_3$, —(CH$_2$)—(CH$_2$)—(CH$_2$)—S—CH$_3$, —(CH$_2$)—(CH$_2$)—(CH$_2$)—N(CH$_3$)—(CH$_3$) and —(CH$_2$)—O—CH$_3$.

In relation to aliphatic radicals, the term "substituted"—unless otherwise defined—refers in the sense of the present invention to the single or multiple substitution, preferably the single, double, triple, quadruple, quintuple, sextuple, septuple, octuple or nonuple substitution, of one or more hydrogen atoms by, for example, F, Cl, Br, I, —CN, —NO$_2$, —OH, —SH and —NH$_2$, the multiple substitution being carried out either on different or on identical atoms several times, for example twice or three times, for example three times on the same carbon atom as in the case of —CF$_3$ or —CH$_2$CF$_3$ or at various locations as in the case of —CH(OH)—CH═CCl—CH$_2$Cl. The multiple substitution can be carried out with the same or with different substituents. Preferred substituted aliphatic radicals include —CH$_2$—Cl, —CH$_2$—Br, —CH$_2$—CH$_2$—Cl, —CH$_2$—CH$_2$—Br, —CH$_2$—CH$_2$—H$_2$—Br and —CH$_2$—CH$_2$—CH$_2$—Cl.

Cycloaliphatic radicals in the sense of the present invention are cyclic saturated or unsaturated hydrocarbon radicals containing preferably 3, 4, 5, 6, 7, 8, 9, 10, 11, 12, 13, 14, 15 or 16, particularly preferably 3, 4, 5, 6, 7 or 8 carbon atoms, wherein each radical can be unsubstituted or singly substituted or multiply substituted by the same or different substituents. Cycloaliphatic radicals preferably have 1, 2, 3, 4 or 5 heteroatoms selected independently of one another from the group consisting of oxygen, nitrogen (NH) and sulphur as ring members.

Examples of cycloaliphatic radicals which can optionally be bridged with 1 or 2 linear or branched $C_{1-5}$ alkylene groups and condensed with a mono- or polycyclic ring system include cyclopropyl, cyclobutyl, cyclopentyl, cyclohexyl, cyclooctyl, cyclononyl, cyclodecyl, cycloundecyl, cyclododecyl, cycloheptyl, cyclopentenyl, cyclohexenyl, cycloheptenyl, [6,6]-dimethyl-[3.1.1]-bicycloheptyl, adamantyl, oxiranyl, aziridinyl, tetrahydrofuranyl, tetrahydrothienyl, pyrrolidinyl, isoxazolidinyl, isothioazolidinyl, pyrazolidinyl, oxazolidinyl, thiazolidinyl, imidazolidinyl, (1,2,4)-oxadiazolidinyl, (1,2,4)-thiadiazolidinyl, (1,2,4)-triazolidin-3-yl, (1,3,4)-thiadiazolidinyl, (1,3,4)-triazolidin-1-yl, (1,3,4)-triazolidin-2-yl, (2,3)-dihydrofuryl, (2,5)-dihydrofuryl, (2,3)-dihydrothienyl, (2,5)-dihydrothienyl, (2,3)-dihydropyrrolyl, (2,5)-dihydropyrrolyl, (2,3)-dihydroisoxazolyl, (4,5)-dihydroisoxazolyl, (2,5)-dihydroisothiazolyl, (2,3)-dihydropyrazolyl, (4,5)-dihydropyrazolyl, (2,5)-dihydropyrazolyl, (2,3)-dihydrooxazolyl, (4,5)-dihydrooxazolyl, (2,5)-dihydrooxazolyl, (2,3)-dihydrothiazolyl, (4,5)-dihydrothiazolyl, (2,5)-dihydrothiazolyl, (2,3)-dihydroimidazolyl, (4,5)-dihydroimidazolyl, (2,5)-dihydroimidazolyl, morpholinyl, piperidinyl, piperazinyl, tetrahydropyridazinyl, tetrahydropyrimidinyl, tetrahydropyrazinyl, (1,3,5)-tetrahydrotriazinyl, (1,2,4)-tetrahydrotriazin-1-yl, (1,2,4)-tetrahydrotriazin-3-yl, (1,3)-dihydrooxazinyl, (1,3)-dithian-2-yl, tetrahydropyranyl, (1,3)-dioxolan-2-yl, (3,4,5,6)-tetrahydropyridin-2-yl, (1,2,5,6)-tetrahydropyridin-1-yl, (1,2,3,4)-tetrahydropyridin-1-yl, (1,2)-dihydropyridin-1-yl, (1,4)-dihydropyridin-1-yl, 4H-1,3-thiazinyl, 4H-1,3-benzothiazin-2-yl, (1,1)-dioxo-2,3,4,5-tetrahydrothien-2-yl, 2H-1,4-benzothiazinyl, (1,3)-dihydrooxazin-2-yl, hexahydroazepin-1-yl, (1,4)-diazepanyl, thiomorpholinyl, dithiolanyl, indanyl, indenyl, (1,4)-benzodioxanyl, (1,2,3,4)-tetrahydronaphthyl, (1,2,3,4)-tetrahydroquinolinyl, (1,2,3,4)-tetrahydroquinazolinyl, (1,3,4,5)-tetrahydropyrido[4,3-b]indolyl, (3,4)-dihydro-1H-isoquinolinyl, decahydroquinolin-1-yl, (1,2,3,4)-tetrahydroisoquinolin-1-yl, decahydroisoquinolin-1-yl and (1,3,4,9)-tetrahydro-[b]-carbolinyl.

A mono- or polycyclic ring system refers in the sense of the present invention to mono- or polycyclic hydrocarbon radicals which are saturated or unsaturated and can optionally have 1, 2, 3, 4 or 5 heteroatom(s) as ring member(s) which are selected independently of one another from the group consisting of oxygen, nitrogen and sulphur. A mono- or polycyclic ring system of this type can, for example, be condensed (anellated) with an aryl radical or a heteroaryl radical.

If a polycyclic ring system such as, for example, a bicyclic ring system is present, the various rings can, each independently of one another, have a differing degree of saturation, i.e. be saturated or unsaturated. Preferably, a polycyclic ring system is a bicyclic ring system.

Examples of aryl radicals which are condensed with a mono- or polycyclic ring system include [1,3]-benzodioxolyl, [1,4]-benzodioxanyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl and [3,4]-dihydro-2H-1,4-benzoxazinyl.

In relation to cycloaliphatic radicals and mono- or polycyclic ring systems, the term "substituted"—unless otherwise defined—refers in the sense of the present invention to the single or multiple substitution, preferably the single, double, triple, quadruple, quintuple, sextuple, septuple, octuple or nonuple substitution, of one or more hydrogen atoms by, for example, oxo (═O), thioxo (═S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(═O)—OH, —C(═O)—O—C$_{1-5}$ alkyl, —O—C(═O)—C$_{1-5}$ alkyl, —NH—C$_{1-5}$ alkyl, —N(C$_{1-5}$ alkyl)$_2$, —NH—C(═O)—O—C$_{1-5}$ alkyl, —C(═O)—H, —C(═O)—C$_{1-5}$ alkyl, —C(═O)—NH$_2$, —C(═O)—

NH—$C_{1-5}$ alkyl, C(=O)—N—($C_{1-5}$ alkyl)$_2$, —S(=O)$_2$—$C_{1-5}$ alkyl, —S(=O)$_2$ phenyl, —NH—S(=O)$_2$—$C_{1-5}$ alkyl, —S(=O)$_2$—NH—$C_{1-5}$ alkyl, cyclohexyl, cyclopentyl, pyridinyl, pyridazinyl, —(CH$_2$)— benzo[b]furanyl, —O-phenyl, —O-benzyl, phenyl and benzyl, wherein in each case the cyclic portion of the radicals pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl can be substituted with 1, 2, 3, 4 or 5 substituents selected independently of one another from the group consisting of F, Cl, Br, —OH, —CF$_3$, —SF$_5$, —CN, —NO$_2$, —$C_{1-5}$ alkyl, —O—$C_{1-5}$ alkyl, —O—CF$_3$, —S—CF$_3$, phenyl and —O-benzyl. The multiple substitution be carried out either on different or on identical atoms several times, for example twice or three times. The multiple substitution can be carried out with the same or with different substituents.

The expression aryl radical refers for the purposes of the present invention preferably to a radical which is selected from the group comprising phenyl, naphthyl, phenanthrenyl and anthracenyl and is unsubstituted or singly or multiply substituted by the same or different substituents. Particularly preferably, the aryl is an unsubstituted or singly substituted phenyl, 1-naphthyl or 2-naphthyl or a phenyl, 1-naphthyl or 2-naphthyl substituted several times, for example twice, three, four or five times, by the same or different substituents.

Heteroaryl radicals in the sense of the present invention are heterocycles which are heteroaromatic. Heteroaryl radicals have preferably 5 to 14 members, i.e. 5, 6, 7, 8, 9, 10, 11, 12, 13 or 14 members, and have preferably 1, 2, 3, 4 or 5 heteroatoms selected independently of one another from the group comprising oxygen, nitrogen and sulphur. Each heteroaryl radical can be unsubstituted or singly substituted or substituted several times, for example twice, three, four or five times, by the same or different substituents.

Examples of heteroaryl radicals in the sense of the present invention include thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzisoxazolyl, benzothiazolyl, benzo[2,1,3]thiadiazolyl, [1,2,3]-benzothiadiazolyl, [2,1,3]-benzoxadiazolyl and [1,2,3]-benzoxadiazolyl.

In relation to aryl and heteroaryl radicals, in the sense of the present invention, "substituted" refers to the single or multiple, for example the single, double, triple, quadruple or quintuple, substitution of one or more hydrogen atoms of the ring system by suitable substituents. Insofar as these suitable substituents are not defined in relation to aryl or heteroaryl radicals elsewhere in the description or in the claims, suitable substituents include F, Cl, Br, I, —CN, —CF$_3$, —SF$_5$, —OH, —O—$C_{1-10}$ alkyl, —NH$_2$, —NO$_2$, —O—CF$_3$, —S—CF$_3$, —SH, —S—$C_{1-5}$ alkyl, —$C_{1-5}$ alkyl, —C(=O)—OH, —C(=O)—O—$C_{1-5}$ alkyl, —O—C(=O)—$C_{1-5}$ alkyl, —NH—$C_{1-5}$ alkyl, —N($C_{1-5}$ alkyl)$_2$, —NH—C(=O)—O—$C_{1-5}$ alkyl, —C(=O)—H, —C(=O)—$C_{1-5}$ alkyl, —C(=O)—NH$_2$, —C(=O)—NH—$C_{1-5}$ alkyl, C(=O)—N—($C_{1-5}$ alkyl)$_2$, —S(=O)$_2$—$C_{1-15}$ alkyl, —S(=O)$_2$ phenyl, —NH—S(=O)$_2$—$C_{1-5}$ alkyl, —N[S(=O)$_2$)—$C_{1-5}$ alkyl]$_2$, —NH—S(=O)$_2$—$C_{1-5}$ alkylenephenyl, —NH—S(=O)$_2$—$C_{1-5}$ alkylenenaphthyl, —NH—S(=O)$_2$ phenyl, —NH—S(=O)$_2$ naphthyl, —S(=O)$_2$—NH—$C_{1-5}$ alkyl, cyclohexyl, cyclopentyl, piperidinyl, morpholinyl, pyrrolidinyl, pyridinyl, pyridazinyl, —(CH$_2$)-benzo[b]furanyl, —O-phenyl, —O-benzyl, phenyl and benzyl, wherein in each case the cyclic portion of the radicals pyridinyl, cyclopentyl, cyclohexyl, piperidinyl, morpholinyl, pyrrolidinyl, pyridazinyl, —S(=O)$_2$ phenyl, —O-phenyl, —O-benzyl, phenyl, —(CH$_2$)-benzo[b]furanyl, —NH—S(=O)$_2$—$C_{1-5}$ alkylenephenyl, —NH—S(=O)$_2$—$C_{1-5}$ alkylenenaphthyl, —NH—S(=O)$_2$ phenyl, —NH—S(=O)$_2$ naphthyl and benzyl can be substituted with 1, 2, 3, 4 or 5 substituents selected independently of one another from the group consisting of F, Cl, Br, —OH, —CF$_3$, —SF$_5$, —CN, —NO$_2$, —$C_{1-5}$ alkyl, —O—$C_{1-5}$ alkyl, —O—CF$_3$, —S—CF$_3$, phenyl and —O-benzyl. The multiple substitution is carried out with the same or with different substituents.

The radicals selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl, [3,4]-dihydro-2H-1,4-benzoxazinyl and benzothiazolyl can be substituted like the above-mentioned aryl and heteroaryl radicals.

If R$^2$ represents a substituted phenyl radical, this substituted phenyl radical can particularly preferably be selected from the group consisting of biphenyl, 2-pentafluorosulphanylphenyl, 2-methanesulphonamidephenyl, 2-ethanesulphonamidephenyl, 2-trifluoromethylphenyl, 2-butoxyphenyl, 2-(1,1)-dimethylpropylphenyl, 2-nitrophenyl, 2-ethylbenzoate, 2-acetamidephenyl, 2-dimethylaminophenyl, 2-diethylaminophenyl, 2-aminophenyl, 2-benzenesulphonamide, 2-trifluoromethylsulphanylphenyl, 2-ethylphenyl, 2-tert-butylphenyl, 2-methylbenzoate, 2-methanesulphonylphenyl, 2-ethylaminosulphonylphenyl, 2-methylaminosulphonylphenyl, 2-bromophenyl, 2-chlorophenyl, 2-fluorophenyl, 2-methylphenyl, 2-trifluoromethoxyphenyl, 2-methoxyphenyl, 2-ethoxyphenyl, 2-propylphenyl, 2-cyanophenyl, 2-acetylphenyl, 2-isopropylphenyl, 2-iodophenyl, 3-pentafluorosulphanylphenyl, 3-chlorophenyl, 3-methylphenyl, 3-butoxyphenyl, 3-nitrophenyl, 3-tert-butylphenyl, 3-trifluoromethylsulphanylphenyl, 3-trifluoromethylphenyl, 3-methanesulphonylphenyl, 3-methanesulphonamidephenyl, 3-ethanesulphonamidephenyl, 3-benzenesulphonamide, 3-ethylbenzoate, 3-fluorophenyl, 3-propylphenyl, 3-isopropylphenyl, 3-bromophenyl, 3-dimethylaminophenyl, 3-(1,1)-dimethylpropylphenyl, 3-acetamidephenyl, 3-diethylaminophenyl, 3-aminophenyl, 3-methoxyphenyl, 3-ethylphenyl, 3-ethylaminosulphonylphenyl, 3-methylaminosulphonylphenyl, 3-ethoxyphenyl, 3-cyanophenyl, 3-iodophenyl, 3-trifluoromethoxyphenyl, 3-acetylphenyl, 4-methanesulphonylphenyl, 4-methylaminosulphonylphenyl, 4-ethylaminosulphonylphenyl, 4-methanesulphonamidephenyl, 4-ethanesulphonamidephenyl, 4-pentafluorosulphanylphenyl, 4-bromophenyl, 4-methoxyphenyl, 4-chlorophenyl, 4-benzenesulphonamide, 4-fluorophenyl, 4-tert-butylphenyl, 4-cyanophenyl, 4-butoxyphenyl, 4-nitrophenyl, 4-trifluoromethylsulphanylphenyl, 4-methylphenyl, 4-isopropylphenyl, 4-trifluoromethylphenyl, 4-dimethylaminophenyl, 4-propylphenyl, 4-diethylaminophenyl, 4-ethylbenzoate, 4-aminophenyl, 4-iodophenyl, 4-trifluoromethoxyphenyl, 4-(1,1)-dimethylpropylphenyl, 4-(3,5-dichlorophenylsulphamoyl)phenyl, 4-acetamidephenyl, 4-ethylphenyl, 4-ethoxyphenyl, 4-methylbenzoate, 4-acetyl phenyl, 2-fluoro-3-trifluoromethylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, 2-chloro-4-nitrophenyl, (2,4)-dibromophenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-methoxy-5-nitrophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, (3,4)-dichlorophenyl, 4-chloro-3-nitrophenyl, 4-fluoro-3-trifluoromethylphenyl, 3-fluoro-4-trifluoromethylphenyl, (3,4)-difluorophenyl, 4-chloro-3-trifluoromethyl, 4-bromo-3-methylphenyl, 4-bromo-5-methylphenyl, 3-chloro-4-fluorophenyl, 4-fluoro-3-nitrophenyl, 4-bromo-3-nitrophenyl, (3,4)-dibromophenyl, 4-chloro-3-methylphenyl, 4-bromo-3-methylphenyl, 4-fluoro-3-methylphenyl, 4-methyl-3-nitrophenyl, (3,5)-dimethoxyphenyl, (3,5)-bis-trifluoromethylphenyl, (3,5)-difluorophenyl, (3,5)-dinitrophenyl, (3,5)-dichlorophenyl, 3-fluoro-5-trifluoromethylphenyl, 5-fluoro-3-trifluoromethylphenyl, (3,5)-dibromophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methylphenyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (2,3,4,5)-tetrafluorophenyl, 4-methoxy-2,3,6-trimethylphenyl, 4-methoxy-2,3,6-trimethylphenyl, 4-chloro-2,5-dimethylphenyl, 2-chloro-6-fluoro-3-methylphenyl, 6-chloro-2-fluoro-3-methyl and (2,3,4,5,6)-pentafluorophenyl.

The above-mentioned linear or branched alkylene, alkenylene or alkinylene groups preferably have 1 to 5 carbon atoms, i.e. the groups are $C_{1-5}$ alkylene, $C_{2-5}$ alkenylene or $C_{2-5}$ alkinylene groups which can be respectively unsubstituted or substituted with 1, 2, 3, 4 or 5 substituents selected independently of one another from the group consisting of F, Cl, Br, —OH, —SH, —NH$_2$, —CN, —NO$_2$ and phenyl, wherein the phenyl radical can be substituted with 1, 2, 3, 4 or 5 substituents selected independently of one another from the group consisting of methyl, ethyl, n-propyl, isopropyl, n-butyl, isobutyl, sec-butyl, tert-butyl, n-pentyl, isopentyl and neo-pentyl.

The above-mentioned alkylene, alkenylene or alkinylene groups optionally each have 1 or 2 heteroatom(s) selected from the group consisting of oxygen, nitrogen, i.e. —N(H)— and —N($C_{1-6}$ alkyl)-, and sulphur as chain member(s).

Preferably, alkylene groups can be selected from the group consisting of —(CH$_2$)—, —(CH$_2$)$_2$—, —C(H)(CH$_3$)—, —C(CH$_3$)$_2$—, —(CH$_2$)$_3$—, —(CH$_2$)$_4$—, —(CH$_2$)$_5$—, —C(H)(CH$_3$)—(CH$_2$)—, —C(H)(C$_2$H$_5$)—(CH$_2$)—, —C(phenyl)$_2$-, —C(H)(phenyl)-, —(CH$_2$)—O—, —(CH$_2$)—N(CH$_3$)—, —(CH$_2$)—S—, —(CH$_2$)—(CH$_2$)—N(CH$_3$)— and —(CH$_2$)—(CH$_2$)—N(C$_2$H$_5$)—.

Preferably, alkenylene groups can be selected from the group consisting of —CH═CH—, —C(CH$_3$)═CH—, —C(C$_2$H$_5$)═CH—, —CH═C(CH$_3$)—, —CH═C(C$_2$H$_5$)—, —CH═C(phenyl)-, —CH═C(p-tolyl), —C(phenyl)═CH— and —C(p-tolyl)═CH—.

Preferably, an alkinylene group can represent —C≡C—.
Preferred are substituted spiro compounds of the above-indicated general formula I, wherein
n is equal to 0, 1 or 2,
I.)
$R^1$ represents a linear or branched, saturated or unsaturated, optionally substituted $C_{1-10}$ aliphatic radical;
an unsaturated or saturated, optionally substituted 3, 4, 5, 6, 7, 8 or 9-membered cycloaliphatic radical which can be condensed with a saturated, unsaturated or aromatic, optionally substituted mono- or polycyclic ring system;
an optionally substituted 5 to 14-membered aryl or heteroaryl radical which can be condensed with a saturated or unsaturated, optionally substituted mono- or polycyclic ring system,
a —C(═O)—NR$^{11}$R$^{12}$ group,
or —(CHR$^{15}$)—X$_e$—(CHR$^{16}$)$_f$—Y$_g$—(CHR$^{17}$)$_h$—Z$_k$—R$^{18}$ wherein e=0 or 1, f=0 or 1, g=0 or 1, h=0 or 1 and k=0 or 1, wherein X, Y and Z, independently of one another, each represent O, S, NH, N(CH$_3$), N(C$_2$H$_5$) or N[CH(CH$_3$)$_2$];
and
$R^2$, $R^3$, $R^4$, $R^5$, $R^6$, $R^7$ and $R^8$, independently of one another, each
represent a hydrogen radical
or a linear or branched, saturated or unsaturated, optionally substituted $C_{1-10}$ aliphatic radical;
or
II.)
$R^1$ and $R^3$ together represent a —(CH$_2$)$_p$ group wherein p=3, 4, 5 or 6;
and
$R^2$, $R^4$, $R^5$, $R^6$, $R^7$ and $R^8$, independently of one another, each represent a hydrogen radical
or a linear or branched, saturated or unsaturated, optionally substituted $C_{1-10}$ aliphatic radical;
or
III.)
$R^1$, $R^2$, $R^7$ and $R^8$ each represent a hydrogen radical
and
$R^3$, $R^4$, $R^5$ and $R^6$, independently of one another, each
represent a linear or branched, saturated or unsaturated, optionally substituted $C_{1-10}$ aliphatic radical;
and in each case
$R^9$ represents a hydrogen radical;
a linear or branched, saturated or unsaturated, optionally substituted $C_{1-10}$ aliphatic radical;
an unsaturated or saturated, optionally substituted 3, 4, 5, 6, 7, 8 or 9-membered cycloaliphatic radical which can be condensed with a saturated, unsaturated or aromatic, optionally substituted mono- or polycyclic ring system;
an optionally substituted 5 to 14-membered aryl or heteroaryl radical which can be condensed with a saturated or unsaturated, optionally substituted mono- or polycyclic ring system;
or represents —(CHR$^{19}$)—X$_q$—(CHR$^{20}$)$_r$—Y$_s$—(CHR$^{21}$)$_t$—Z$_u$—R$^{22}$ wherein q=0 or 1, r=0 or 1, s=0 or 1, t=0 or 1 and u=0 or 1, wherein X, Y and Z, independently of one another, each represent O, S, NH, N(CH$_3$), N(C$_2$H$_5$) or N[CH(CH$_3$)$_2$];
$R^{10}$ represents a linear or branched, saturated or unsaturated, optionally substituted $C_{1-10}$ aliphatic radical;
an unsaturated or saturated, optionally substituted 3, 4, 5, 6, 7, 8 or 9-membered cycloaliphatic radical which can be condensed with a saturated, unsaturated or aromatic, optionally substituted mono- or polycyclic ring system and/or bound via a —(CH$_2$), group wherein v=1, 2, 3, 4 or 5;

a phenyl radical which can be substituted with 1, 2, 3, 4 or 5 substituents selected independently of one another from the group consisting of F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-10}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —NH—S(=O)$_2$—C$_{1-5}$ alkylenephenyl, —NH—S(=O)$_2$—C$_{1-5}$ alkylenenaphthyl, —NH—S(=O)$_2$ phenyl, —NH—S(=O)$_2$ naphthyl, cyclohexyl, cyclopentyl, morpholinyl, piperidinyl, piperazinyl, pyrrolidinyl, pyridinyl, pyridazinyl, —(CH$_2$)-benzo[b]furanyl, —O-phenyl, —O-benzyl, phenyl and benzyl, wherein in each case the cyclic portion of the radicals pyridinyl, cyclopentyl, cyclohexyl, morpholinyl, piperidinyl, piperazinyl, pyrrolidinyl, pyridazinyl, —S(=O)$_2$ phenyl, —O-phenyl, —O-benzyl, phenyl, —(CH$_2$)— benzo[b]furanyl, —NH—S(=O)$_2$—C$_{1-5}$ alkylenephenyl, —NH—S(=O)$_2$—C$_{1-5}$ alkylenenaphthyl, —NH—S(=O)$_2$ phenyl, —NH—S(=O)$_2$ naphthyl and benzyl can be substituted with 1, 2, 3, 4 or 5 substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl, on the condition that not one of the meta positions and the para position of this phenyl radical are substituted with substituents which are respectively bound to the phenyl radical via an identical atom selected from the group consisting of oxygen, sulphur and nitrogen;

represents an optionally substituted radical selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl; 2H-benzo[1.4]oxazin-3(4H)-onyl, (3,4)-dihydroquinolin-2(1H)-onyl, [3,4]-dihydro-2H-1,4-benzoxazinyl and benzothiazolyl;

an optionally substituted 5 to 14-membered aryl or heteroaryl radical which can be condensed with a saturated or unsaturated, optionally substituted mono- or polycyclic ring system and/or is bound via a —(CH$_2$)—, —(CH$_2$)$_2$— or —(CH$_2$)$_3$ group;

or represents a —C(=O)—NR$^{13}$R$^{14}$ group;

R$^{11}$ and R$^3$, independently of one another, each represent a linear or branched, saturated or unsaturated, optionally substituted C$_{1-10}$ aliphatic radical;

an unsaturated or saturated, optionally substituted 3, 4, 5, 6, 7, 8 or 9-membered cycloaliphatic radical which can be condensed with a saturated, unsaturated or aromatic, optionally substituted mono- or polycyclic ring system and/or bound via a —(CH$_2$)$_w$ group wherein w=1, 2, 3, 4 or 5;

or an optionally substituted 5 to 14-membered aryl or heteroaryl radical which can be condensed with a saturated or unsaturated, optionally substituted mono- or polycyclic ring system and/or bound via a —(CH$_2$)—, —(CH$_2$)$_2$— or —(CH$_2$)$_3$ group;

R$^{12}$ and R$^{14}$, independently of one another, each represent a hydrogen radical;

a linear or branched, saturated or unsaturated, optionally substituted C$_{1-10}$ aliphatic radical;

an unsaturated or saturated, optionally substituted 3, 4, 5, 6, 7, 8 or 9-membered cycloaliphatic radical which can be condensed with a saturated, unsaturated or aromatic, optionally substituted mono- or polycyclic ring system and/or bound via a —(CH$_2$)$_C$ group wherein w=1, 2, 3, 4 or 5;

represent an optionally substituted 5 to 14-membered aryl or heteroaryl radical which can be condensed with a saturated or unsaturated, optionally substituted mono- or polycyclic ring system and/or bound via a —(CH$_2$) group;

or

R$^{11}$ and R$^{12}$ or R$^{13}$ and R$^{14}$ respectively form together with the nitrogen atom connecting them as ring member a saturated or unsaturated, optionally substituted 4, 6, 7, 8 or 9-membered heterocycloaliphatic radical which can be condensed with a saturated, unsaturated or aromatic, optionally substituted mono- or polycyclic ring system, R$^{15}$, R$^{16}$, R$^{17}$, R$^{19}$, R$^{20}$ and R$^{21}$, independently of one another, each represent a hydrogen radical or a linear or branched, saturated or unsaturated, optionally substituted C$_{1-10}$ aliphatic radical;

and

R$^{18}$ and R$^{22}$, independently of one another, each represent a linear or branched, saturated or unsaturated, optionally substituted C$_{1-10}$ aliphatic radical;

an unsaturated or saturated, optionally substituted 3, 4, 5, 6, 7, 8 or 9-membered cycloaliphatic radical which can be condensed with a saturated, unsaturated or aromatic, optionally substituted mono- or polycyclic ring system;

or an optionally substituted 5 to 14-membered aryl or heteroaryl radical which can be condensed with a saturated or unsaturated, optionally substituted mono- or polycyclic ring system;

wherein the above-mentioned C$_{1-10}$ aliphatic radicals can in each case optionally be substituted with 1, 2, 3, 4, 5, 6, 7, 8 or 9 substituents selected independently of one another from the group consisting of F, Cl, Br, I, —CN, —NO$_2$, —OH, —SH and —NH$_2$;

the above-mentioned cycloaliphatic radicals can in each case optionally be substituted with 1, 2, 3, 4 or 5 substituents selected independently of one another from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-15}$ alkyl, —S(=O)$_2$—NH—C$_{1-5}$ alkyl, cyclohexyl, cyclopentyl, pyridinyl, pyridazinyl, —(CH$_2$)-benzo[b]furanyl, —O-phenyl, —O-benzyl, phenyl and benzyl, wherein in each case the cyclic portion of the radicals pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl can be substituted with 1, 2, 3, 4 or 5 substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl, and the above-mentioned cycloaliphatic radicals can in each case optionally have 1, 2, 3, 4 or 5 heteroatom(s) selected independently of one another from the group consisting of oxygen, nitrogen and sulphur as ring member(s);

the above-mentioned heterocycloaliphatic radicals formed by R$^{11}$ and R$^{12}$ or R$^{13}$ and R$^{14}$ can in each case optionally be substituted with 1, 2, 3, 4 or 5 substituents selected independently of one another from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—NH$_2$, —C(=O)—NH—C$_{1-5}$ alkyl, —C(=O)—N—(C$_{1-5}$ alkyl)$_2$, cyclohexyl, cyclopentyl, pyridinyl, pyridazinyl, pyrimidinyl, [1,2,5]-thiadiazolyl, thiazolyl, —(CH$_2$)-benzo[b]furanyl, —O-phenyl, —O-benzyl, phenyl and benzyl, wherein in each case the cyclic portion of the radicals pyrimidinyl, [1,2,5]-thiadiazolyl, thiazolyl, pyridinyl, cyclopentyl, cyclohexyl, pyridazinyl, —O-phenyl, —O-benzyl, phenyl, —(CH$_2$)— benzo[b]furanyl and benzyl can be substituted with 1, 2, 3, 4 or 5 substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl, and the above-mentioned heterocycloaliphatic radicals formed by R$^{11}$ and R$^{12}$ or R$^{13}$ and R$^{14}$ can in each case optionally have 1, 2 or 3 additional heteroatom(s) independently of one another from the group consisting of oxygen, nitrogen and sulphur as ring member(s);

the rings of the above-mentioned mono- or polycyclic ring systems can in each case optionally be substituted with 1, 2, 3, 4 or 5 substituents selected independently of one another from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —S(=O)$_2$—NH—C$_{1-5}$ alkyl, cyclohexyl, cyclopentyl, pyridinyl, pyridazinyl, —(CH$_2$)— benzo[b]furanyl, —O-phenyl, —O-benzyl, phenyl and benzyl, wherein in each case the cyclic portion of the radicals pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl can be substituted with 1, 2, 3, 4 or 5 substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl, and the rings of the above-mentioned mono- or polycyclic ring systems each have 5, 6 or 7 members and can in each case optionally have 1, 2, 3, 4 or 5 heteroatom(s) as ring member(s) selected independently of one another from the group consisting of oxygen, nitrogen and sulphur;

and, unless otherwise defined, the above-mentioned radicals selected from the group consisting of phenyl, naphthyl (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl; 2H-benzo[1.4]oxazin-3(4H)-onyl, (3,4)-dihydroquinolin-2(1H)-onyl, [3,4]-dihydro-2H-1,4-benzoxazinyl and benzothiazolyl and aryl or heteroaryl radicals can in each case optionally be substituted with 1, 2, 3, 4 or 5 substituents selected independently of one another from the group consisting of F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-10}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —N[S(=O)$_2$]—C$_{1-5}$ alkyl]$_2$, —S(=O)$_2$—NH—C$_{1-5}$ alkyl, cyclohexyl, cyclopentyl, piperidinyl, pyrrolidinyl, morpholinyl, pyridinyl, pyridazinyl, —(CH$_2$)— benzo[b]furanyl, —O-phenyl, —O-benzyl, phenyl and benzyl, wherein in each case the cyclic portion of the radicals pyridinyl, cyclopentyl, cyclohexyl, piperidinyl, pyrrolidinyl, morpholinyl, pyridazinyl, —S(=O)$_2$ phenyl, —O-phenyl, —O-benzyl, phenyl, —(CH$_2$)— benzo[b]furanyl and benzyl can be substituted with 1, 2, 3, 4 or 5 substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl, and the above-mentioned heteroaryl radicals can in each case optionally have 1, 2, 3, 4 or 5 heteroatom(s) selected independently of one another from the group consisting of oxygen, nitrogen and sulphur as ring member(s);

in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

A person skilled in the art will understand that for n is equal to 1, the following general formula Ia is obtained:

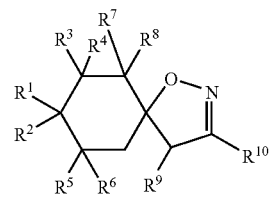

Ia

24

Particularly preferred are substituted spiro compounds of the above-indicated general formula I, wherein n is equal to 1;

I.)

R$^1$ represents a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

represents a radical selected from the group consisting of cyclopropyl, cyclobutyl, cyclopentyl, cyclohexyl and cycloheptyl;

represents a radical selected from the group consisting of phenyl and naphthyl, wherein the radical can in each case optionally be substituted with 1, 2, 3, 4 or 5 substituents selected independently of one another from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$ and —C(=O)—N—(C$_2$H$_5$)$_2$;

represents a —C(=O)—NR$^{11}$R$^{12}$ group;

or represents —(CHR$^{15}$)—R$^{18}$ or —(CHR$^{15}$)—(CHR$^{16}$)—R$^{18}$;

and

R$^2$, R$^3$, R$^4$, R$^5$, R$^6$, R$^7$ and R$^8$, independently of one another, each represent a hydrogen radical or a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

or

II.)

R$^1$ and R$^3$ together represent a —(CH$_2$)$_p$ group wherein p=3 or 4;

and

R$^2$, R$^4$, R$^5$, R$^6$, R$^7$ and R$^8$, independently of one another, each represent a hydrogen radical or a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

or

III.)

R$^1$, R$^2$, R$^7$ and R$^8$ each represent a hydrogen radical and

R$^3$, R$^4$, R$^5$ and R$^6$, independently of one another, each represent a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

and in each case

R$^9$ represents a hydrogen radical;

represents a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

represents a radical selected from the group consisting of phenyl and naphthyl, wherein the radical can in each case optionally be substituted with 1, 2, 3, 4 or 5 substituents selected independently of one another from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$ and —C(=O)—N—(C$_2$H$_5$)$_2$;

or represents —(CHR$^{19}$)—R$^{22}$ or —(CHR$^{19}$)—(CHR$^{20}$)—R$^{22}$;

R$^{10}$ represents a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl;

represents a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl which can be bound via a —(CH$_2$)— or —(CH$_2$)$_2$ group;

represents a radical selected from the group consisting of phenyl, naphthyl, benzyl, phenethyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl and benzothiazolyl, wherein the radical can in each case optionally be substituted with 1, 2, 3, 4 or 5 substituents selected independently of one another from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —NH—S(=O)$_2$ phenyl, —S(=O)$_2$—NH—CH$_3$, —S(=O)$_2$—NH—C$_2$H$_5$, cyclohexyl, cyclopentyl, pyridinyl, pyridazinyl, —(CH$_2$)-benzo[b]furanyl, —O-phenyl, —O-benzyl, phenyl and benzyl, wherein in each case the cyclic portion of the radicals pyridinyl, cyclopentyl, cyclohexyl, pyridazinyl, —S(=O)$_2$ phenyl, —NH—S(=O)$_2$ phenyl, —O-phenyl, —O-benzyl, phenyl, —(CH$_2$)-benzo[b]furanyl and benzyl can be substituted with 1, 2, 3, 4 or 5 substituents selected independently of one another from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl;
on the condition that not one of the meta positions and the para position of this phenyl radical are substituted with substituents which are respectively bound to the phenyl radical via an identical atom selected from the group consisting of oxygen, sulphur and nitrogen;
or represents a —C(=O)—NR$^{13}$R$^{14}$ group;

R$^{11}$ represents a radical selected from the group consisting of phenyl, naphthyl, indolyl, pyridinyl, (1,3)-benzodioxolyl and (1,4)-benzodioxanyl, wherein the radical can in each case optionally be substituted with 1, 2, 3, 4 or 5 substituents selected independently of one another from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$, —NH—C$_2$H$_5$, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, piperidinyl, 4-methylpiperidinyl and phenyl; wherein the phenyl radical can be substituted with 1, 2 or 3 substituents selected from the group consisting of F, Cl and Br; and/or bound via a —(CH$_2$) group or —(CH$_2$)$_2$ group;

R$^{13}$ represents a radical selected from the group consisting of phenyl, naphthyl, (1,3)-benzodioxolyl, (1,4)-benzodioxanyl, pyridinyl, quinazolinyl, quinoxalinyl, quinolinyl, isoquinolinyl, benzimidazolyl, benzotriazolyl, benzoxazolyl, benzisoxazolyl and benzothiazolyl, wherein the radical can in each case optionally be substituted with 1, 2, 3, 4 or 5 substituents selected independently of one another from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —N[S(=O)$_2$—CH$_3$)]$_2$, —N[S(=O)$_2$—C$_2$H$_5$)]$_2$, —S(=O)$_2$—NH—CH$_3$ and —S(=O)$_2$—NH—C$_2$H$_5$ and/or bound via a —(CH$_2$)— or —(CH$_2$)$_2$ group;

R$^{12}$ and R$^{14}$, independently of one another, each represent a hydrogen radical;
or
R$^{11}$ and R$^{12}$ or R$^{13}$ and R$^{14}$ respectively form together with the nitrogen atom connecting them as ring member a radical selected from the group consisting of pyrrolidinyl, piperidinyl, (1,3,4,5)-tetrahydropyrido[4,3-b]indolyl, (3,4)-dihydro-1H-isoquinolinyl, (1,3,4,9)-tetrahydro-[b]-carbolinyl, imidazolidinyl, (1,3)-thiazolidinyl, piperazinyl, morpholinyl, azepanyl, diazepanyl and thiomorpholinyl, wherein the radical can in each case optionally be substituted with 1, 2, 3, 4 or 5 substituents selected independently of one another from the group consisting of oxo (=O), thioxo (=S), F, Cl, Br, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$, pyridinyl, pyridazinyl, pyrimidinyl, [1,2,5]-thiadiazolyl, thiazolyl, phenyl and benzyl, wherein in each case the cyclic portion of the radicals pyrimidinyl, [1,2,5]-thiadiazolyl, thiazolyl, pyridinyl, pyridazinyl, phenyl and benzyl can be substituted with 1, 2, 3, 4 or 5 substituents selected independently of one another from the group consisting of F, Cl, Br, —OH, —CF$_3$, methyl, ethyl, n-propyl, isopropyl, n-butyl, sec-butyl, isobutyl, tert-butyl, —O—CH$_3$, —O—C$_2$H$_5$, —O—CF$_3$ and —S—CF$_3$;

R$^{15}$, R$^{16}$, R$^{19}$ and R$^{20}$, independently of one another, each represent a hydrogen radical;
and
R$^{18}$ and R$^{22}$, independently of one another, each represent a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl,
or represent a radical selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzotriazolyl, benzoxazolyl, benzisoxazolyl and benzothiazolyl.

Most particularly preferred are substituted spiro compounds of the above-indicated general formula I, wherein n is equal to 1, I.)
R$^1$ represents a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
represents a radical selected from the group consisting of cyclopropyl, cyclobutyl, cyclopentyl, cyclohexyl and cycloheptyl;
represents a phenyl radical
or represents a —C(=O)—NR$^{11}$R$^{12}$ group;
R$^2$, R$^7$ and R$^8$ each represent a hydrogen radical;
and
R$^3$, R$^4$, R$^5$, R$^6$, independently of one another, each
represent a hydrogen radical
or a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

II.)
R$^1$ and R$^3$ together represent a —(CH$_2$)$_4$ group;
R$^2$, R$^4$, R$^7$ and R$^8$ each represent a hydrogen radical;
and
R$^5$ and R$^6$, independently of one another, each
represent a hydrogen radical
or a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

or
III.)

$R^1$, $R^2$, $R^7$ and $R^3$ each represent a hydrogen radical
and
$R^3$, $R^4$, $R^5$ and $R^6$, independently of one another, each represent a methyl or ethyl radical;
and in each case
$R^9$ represents a hydrogen radical;
represents a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
or represents a phenyl radical;
$R^{10}$ represents a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
represents a phenyl radical of general formula XX

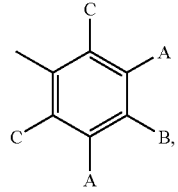

XX wherein the line represents the bond of this phenyl radical to the spiro compound of general formula I;
and A, B and C each represent a substituent selected independently of one another from the group consisting of H, F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, cyclohexyl, cyclopentyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$ and —NH—S(=O)$_2$ phenyl;
on the condition that not one of positions A and position B of this phenyl radical are substituted with substituents which are respectively bound to the phenyl radical via an identical atom selected from the group consisting of oxygen, sulphur and nitrogen;
represents a radical selected from the group consisting of benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl, [3,4]-dihydro-2H-1,4-benzoxazinyl and benzothiazolyl, wherein the respective cyclic portion of the above-mentioned radicals can in each case optionally be substituted with 1, 2, 3, 4 or 5 substituents selected independently of one another from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, pyridinyl, pyridazinyl, —(CH$_2$)-benzo[b]furanyl, —O-phenyl, —O-benzyl, phenyl and benzyl; wherein in each case the cyclic portion of the radicals pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl can be substituted with 1, 2, 3, 4 or 5 substituents selected independently of one another from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl;
or represents a —C(=O)—NR$^{13}$R$^{14}$ group;
$R^{11}$ represents a radical selected from the group consisting of phenyl, indolyl, (1,3)-benzodioxolyl, pyridinyl, (1,4)-benzodioxanyl and naphthyl, wherein the radical can in each case optionally be substituted with 1, 2, 3, 4 or 5 substituents selected independently of one another from the group consisting of F, Cl, Br, —CF$_3$, —SF$_5$, —OH, —O—CH$_3$, —O—C$_2$H$_5$, —O—CF$_3$, phenyl, 3-chloro-4-fluorophenyl, 4-methylpiperidinyl, piperidinyl, methyl, ethyl, n-propyl, isopropyl, n-butyl, sec-butyl, isobutyl, tert-butyl, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$ and/or bound via a —(CH$_2$) group;
$R^{13}$ represents a radical selected from the group consisting of phenyl, naphthyl, (1,3)-benzodioxolyl, (1,4)-benzodioxanyl, pyridinyl, quinolinyl and isoquinolinyl, wherein the radical can in each case optionally be substituted with 1, 2, 3, 4 or 5 substituents selected independently of one another from the group consisting of —SF$_5$, F, Cl, Br, —CF$_3$, —OH, —O—CH$_3$, —O—C$_2$H$_5$, —NH$_2$, methyl, ethyl, n-propyl, isopropyl, n-butyl, sec-butyl, isobutyl, tert-butyl, —N(CH$_3$)$_2$, —N[S(=O)$_2$—CH$_3$)]$_2$, —N[S(=O)$_2$—C$_2$H$_5$)]$_2$, N(C$_2$H$_5$)$_2$, —NH—CH$_3$, —NH—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$ and/or bound via a —(CH$_2$) group;
$R^{12}$ and $R^{14}$, independently of one another, each represent a hydrogen radical;
or
$R^{11}$ and $R^{12}$ or $R^{13}$ and $R^{14}$ respectively form together with the nitrogen atom connecting them as ring member a (3,4)-dihydro-1H-isoquinolinyl radical which can be substituted with 1, 2, 3, 4 or 5 substituents selected independently of one another from the group consisting of —OH, —O—$CH_3$ and —O—$C_2H_5$;

or form together with the nitrogen atom connecting them a radical selected from the group consisting of piperazinyl, 2-methylpiperazinyl, (2,6)-dimethylpiperazinyl and diazepanyl, wherein the radical on a nitrogen atom can be respectively substituted with a substituent selected from the group consisting of pyridinyl, pyridazinyl, pyrimidinyl, [1,2,5]-thiadiazolyl, thiazolyl and phenyl, wherein in each case the cyclic portion of the substituents pyrimidinyl, [1,2,5]-thiadiazolyl, thiazolyl, pyridinyl, pyridazinyl and phenyl can be substituted with 1, 2, 3, 4 or 5 substituents selected independently of one another from the group consisting of F, Cl, Br, —OH, —$CF_3$, methyl, ethyl, n-propyl, isopropyl, n-butyl, sec-butyl, isobutyl and tert-butyl;

in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

Also most particularly preferred are substituted spiro compounds of the above-indicated general formula I, wherein n is equal to 1, I.)
$R^1$ represents a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
represents a radical selected from the group consisting of cyclopropyl, cyclobutyl, cyclopentyl, cyclohexyl and cycloheptyl;
represents a phenyl radical
or represents a —C(=O)—$NR^{11}R^{12}$ group;
$R^2$, $R^7$ and $R^8$ each represent a hydrogen radical;
and
$R^3$, $R^4$, $R^5$, $R^6$, independently of one another, each represent a hydrogen radical
or a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
or
II.)
$R^1$ and $R^3$ together represent a —$(CH_2)_4$ group;
$R^2$, $R^4$, $R^7$ and $R^8$ each represent a hydrogen radical;
and
$R^5$ and $R^6$, independently of one another, each represent a hydrogen radical
or a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
or
III.)
$R^1$, $R^2$, $R^7$ and $R^8$ each represent a hydrogen radical
and
$R^3$, $R^4$, $R^5$ and $R^6$, independently of one another, each represent a methyl or ethyl radical;
and in each case
$R^9$ represents a hydrogen radical;
represents a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
or represents a phenyl radical;
$R^{10}$ represents a radical selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
represents a radical selected from the group consisting of phenyl, 2-methanesulphonamidephenyl, 2-ethanesulphonamidephenyl, 2-trifluoromethylphenyl, 2-trifluoromethylsulphanylphenyl, 2-ethylphenyl, 2-tert-butylphenyl, 2-ethylaminosulphonylphenyl, 2-methylaminosulphonylphenyl, 2-bromophenyl, 2-chlorophenyl, 2-fluorophenyl, 2-methylphenyl, 2-trifluoromethoxyphenyl, 2-methoxyphenyl, 2-ethoxyphenyl, 2-propylphenyl, 2-iodophenyl, 3-chlorophenyl, 3-methylphenyl, 3-tert-butyl phenyl, 3-trifluoromethylsulphanylphenyl, 3-trifluoromethylphenyl, 3-methanesulphonamidephenyl, 3-ethanesulphonamidephenyl, 3-fluorophenyl, 3-propylphenyl, 3-isopropylphenyl, 3-bromophenyl, 3-methoxyphenyl, 3-ethylphenyl, 3-ethylaminosulphonylphenyl, 3-methylaminosulphonylphenyl, 3-ethoxyphenyl, 3-trifluoromethoxyphenyl, 3-iodophenyl, 4-methylaminosulphonylphenyl, 4-ethylaminosulphonylphenyl, 4-methanesulphonamidephenyl, 4-ethanesulphonamidephenyl, 4-bromophenyl, 4-methoxyphenyl, 4-chlorophenyl, 4-fluorophenyl, 4-tert-butylphenyl, 4-trifluoromethylsulphanylphenyl, 4-methylphenyl, 4-isopropylphenyl, 4-trifluoromethylphenyl, 4-propylphenyl, 4-iodophenyl, 4-trifluoromethoxyphenyl, 4-ethylphenyl, 4-ethoxyphenyl, 2-fluoro-3-trifluoromethylphenyl, (2,3)-difluorophenyl, (2,3)-dimethylphenyl, (2,3)-dichlorophenyl, 3-fluoro-2-trifluoromethyl phenyl, (2,4)-dichlorophenyl, (2,4)-difluorophenyl, 4-fluoro-2-trifluoromethylphenyl, (2,4)-dimethoxyphenyl, 2-chloro-4-fluorophenyl, (2,4)-dibromophenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, (3,4)-dichlorophenyl, 4-fluoro-3-trifluoromethylphenyl, 3-fluoro-4-trifluoromethylphenyl, (3,4)-difluorophenyl, 4-chloro-3-trifluoromethylphenyl, 4-bromo-3-methylphenyl, 4-bromo-5-methylphenyl, 3-chloro-4-fluorophenyl, (3,4)-dibromophenyl, 4-chloro-3-methylphenyl, 4-bromo-3-methylphenyl, 4-fluoro-3-methylphenyl, (3,5)-dimethoxyphenyl, (3,5)-bis-trifluoromethylphenyl, (3,5)-difluorophenyl, (3,5)-dichlorophenyl, 3-fluoro-5-trifluoromethyl phenyl, 5-fluoro-3-trifluoromethylphenyl, (3,5)-dibromophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methylphenyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (2,3,4,5)-tetrafluorophenyl, 4-methoxy-2,3,6-trimethylphenyl, 4-methoxy-2,3,6-trimethylphenyl, 4-chloro-2,5-dimethylphenyl, 2-chloro-6-fluoro-3-methylphenyl, 6-chloro-2-fluoro-3-methyl, (2,3,4,5,6)-pentafluorophenyl, 3-fluoro-4-methylsulphonamidophenyl, 3-chloro-4-methylsulphonamidophenyl, 3-bromo-4-methylsulphonamidophenyl, 3-methoxy-4- methylsulphonamidophenyl, 3-hydroxy-4-methylsulphonamidophenyl, 3-trifluoromethyl-4-methylsulphonamidophenyl, 3-trifluoromethoxy-4-methylsulphonamidophenyl, 3-methyl-4-methylsulphonamidophenyl, 3-ethyl-4-methylsulphonamidophenyl, 3-isopropyl-4-methylsulphonamidophenyl, 3-propyl-4-methylsulphonamidophenyl, 3-tert-butyl-4-methylsulphonamidophenyl, 3-fluoro-4-phenylsulphonamidophenyl, 3-chloro-4-phenylsulphonamidophenyl, 3-bromo-4-phenylsulphonamidophenyl, 3-methoxy-4-phenylsulphonamidophenyl, 3-hydroxy-4-phenylsulphonamidophenyl, 3-trifluoromethyl-4-phenylsulphonamidophenyl, 3-trifluoromethoxy-4-phenylsulphonamidophenyl, 3-methyl-4-phenylsulphonamidophenyl, 3-ethyl-4-phenylsulphonamidophenyl, 3-isopropyl-4-phenylsulphonamidophenyl, 3-propyl-4-phenylsulphonamidophenyl, 3-tert-butyl-4-phenylsulphonamidophenyl, 4-fluoro-3-methylsulphonamidophenyl, 4-chloro-3-methylsulphonamidophenyl, 4-bromo-3-methylsulphonamidophenyl, 4-methoxy-3-methylsulphonamidophenyl, 4-hydroxy-3-methylsulphonamidophenyl, 4-trifluoromethyl-3-methylsulphonamidophenyl, 4-trifluoromethoxy-3-methylsulphonamidophenyl, 4-methyl-3-methylsulphonamidophenyl, 4-ethyl-3-methylsulphonamidophenyl, 4-isopropyl-3-methylsulphonamidophenyl, 4-propyl-3-methylsulphonamidophenyl, 4-tert-butyl-3-methylsulphonamidophenyl, 4-fluoro-3-phenylsulphonamidophenyl, 4-chloro-3-phenylsulphonamidophenyl, 4-bromo-3-phenylsulphonamidophenyl, 4-methoxy-3-phenylsulphonamidophenyl, 4-hydroxy-3-phenylsulphonamidophenyl, 4-trifluoromethyl-3-phenylsulphonamidophenyl, 4-trifluoromethoxy-3-phenylsulphonamidophenyl, 4-methyl-3-phenylsulphonamidophenyl, 4-ethyl-3-phenylsulphonamidophenyl, 4-isopropyl-3-phenylsulphonamidophenyl, 4-propyl-3-phenylsulphonamidophenyl, and 4-tert-butyl-3-phenylsulphonamidophenyl;

represents a radical selected from the group consisting of benzyl, phenethyl, thiazolyl, naphthyl, (1,3)-benzodioxolyl, (1,4)-benzodioxanyl and pyridinyl, wherein the cyclic portion of the above-mentioned radicals can optionally be substituted with 1, 2, 3, 4 or 5 substituents selected independently of one another from the group consisting of F, Cl, Br, I, —CF$_3$, —OH, —O—CH$_3$, —O—C$_2$H$_5$, methyl, ethyl, n-propyl, isopropyl, n-butyl, sec-butyl, isobutyl and tert-butyl;

or represents a —C(=O)—NR$^{13}$R$^{14}$ group;

R$^{11}$ represents a radical selected from the group consisting of phenyl, indolyl, pyridinyl, (1,3)-benzodioxolyl, (1,4)-benzodioxanyl and naphthyl, wherein the radical can in each case optionally be substituted with 1, 2, 3, 4 or 5 substituents selected independently of one another from the group consisting of F, Cl, Br, —CF$_3$, —SF$_5$, —OH, —O—CH$_3$, —O—C$_2$H$_5$, —O—CF$_3$, piperidinyl, 4-methylpiperidinyl, 3-chloro-4-fluorophenyl, methyl, ethyl, n-propyl, isopropyl, n-butyl, sec-butyl, isobutyl, tert-butyl, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$ and/or bound via a —(CH$_2$) group;

R$^{13}$ represents a radical selected from the group consisting of phenyl, naphthyl, (1,3)-benzodioxolyl, (1,4)-benzodioxanyl, pyridinyl, quinolinyl and isoquinolinyl, wherein the radical can in each case optionally be substituted with 1, 2, 3, 4 or 5 substituents selected independently of one another from the group consisting of —SF$_5$, F, Cl, Br, —CF$_3$, —OH, —O—CH$_3$, —O—C$_2$H$_5$, —NH$_2$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$, —NH—C$_2$H$_5$, —NH—S(=O)$_2$—CH$_3$, —NH—S(=O)$_2$—C$_2$H$_5$, —N[S(=O)$_2$—CH$_3$)]$_2$, —N[S(=O)$_2$—C$_2$H$_5$)]$_2$, —S(=O)$_2$—NH—CH$_3$ and —S(=O)$_2$—NH—C$_2$H$_5$ and/or bound via a —(CH$_2$) group;

R$^{12}$ and R$^{14}$, independently of one another, each represent a hydrogen radical;

or

R$^{11}$ and R$^{12}$ or R$^{13}$ and R$^{14}$ respectively form together with the nitrogen atom connecting them as ring member a (3,4)-dihydro-1H-isoquinolinyl radical which can be substituted with 1, 2, 3, 4 or 5 substituents selected independently of one another from the group consisting of —OH, —O—CH$_3$ and —O—C$_2$H$_5$;

or form together with the nitrogen atom connecting them a radical selected from the group consisting of piperazinyl, 2-methylpiperazinyl, (2,6)-dimethylpiperazinyl and diazepanyl, wherein the radical on a nitrogen atom can be respectively substituted with a substituent selected from the group consisting of pyridinyl, pyridazinyl, pyrimidinyl, [1,2,5]-thiadiazolyl, thiazolyl and phenyl, wherein in each case the cyclic portion of the substituents pyrimidinyl, [1,2,5]-thiadiazolyl, thiazolyl, pyridinyl, pyridazinyl and phenyl can be substituted with 1, 2, 3, 4 or 5 substituents selected independently of one another from the group consisting of F, Cl, Br, —OH, —CF$_3$, methyl, ethyl, n-propyl, isopropyl, n-butyl, sec-butyl, isobutyl and tert-butyl;

in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

Still more preferred are spiro compounds of general formula I selected from the group consisting of

[1] 8-tert-butyl-1-oxa-2-azaspiro[4.5]dec-2-ene-3-carboxylic acid-4-aminobenzylamide

[2] trans-8-tert-butyl-1-oxa-2-azaspiro[4.5]dec-2-ene-3-carboxylic acid-4-methanesulphonylaminobenzylamide

[3] cis-8-tert-butyl-1-oxa-2-azaspiro[4.5]dec-2-ene-3-carboxylic acid-4-methanesulphonylaminobenzylamide

[4] 8-tert-butyl-1-oxa-2-azaspiro[4.5]dec-2-ene-3-carboxylic acid isoquinolin-5-ylamide

[5] trans-(8-tert-butyl-1-oxa-2-azaspiro[4.5]dec-2-en-3-yl)-(4-thiazol-2-ylpiperazin-1-yl)methanone

[6] cis-(8-tert-butyl-1-oxa-2-azaspiro[4.5]dec-2-en-3-yl)-(4-thiazol-2-ylpiperazin-1-yl)methanone

[7] cis-8-tert-butyl-1-oxa-2-azaspiro[4.5]dec-2-ene-3-carboxylic acid-3-fluoro-4-methanesulphonylaminobenzylamide

[8] trans-(8-tert-butyl-1-oxa-2-azaspiro[4.5]dec-2-en-3-yl)-[4-(3-trifluoromethylpyridin-2-yl)piperazin-1-yl]methanone

[9] cis-(8-tert-butyl-1-oxa-2-azaspiro[4.5]dec-2-en-3-yl)-[4-(3-trifluoromethylpyridin-2-yl)piperazin-1-yl]methanone

[10] trans-(8-tert-butyl-1-oxa-2-azaspiro[4.5]dec-2-en-3-yl)-[4-(4-hydroxyphenyl)piperazin-1-yl]methanone

[11] cis-(8-tert-butyl-1-oxa-2-azaspiro[4.5]dec-2-en-3-yl)-[4-(4-hydroxyphenyl)piperazin-1-yl]methanone

[12] (8-tert-butyl-1-oxa-2-azaspiro[4.5]dec-2-en-3-yl)-(6,7-dihydroxy-3,4-dihydro-1H-isoquinolin-2-yl)methanone
[13] cis-(8-tert-butyl-1-oxa-2-azaspiro[4.5]dec-2-en-3-yl)-[4-(6-methylpyridazin-3-yl)piperazin-1-yl]methanone
[14] trans-(8-tert-butyl-1-oxa-2-azaspiro[4.5]dec-2-en-3-yl)-[4-(6-methylpyridazin-3-yl)piperazin-1-yl]methanone
[15] cis-(8-tert-butyl-1-oxa-2-azaspiro[4.5]dec-2-en-3-yl)-(4-pyrimidin-2-ylpiperazin-1-yl)methanone
[16] trans-(8-tert-butyl-1-oxa-2-azaspiro[4.5]dec-2-en-3-yl)-(4-pyrimidin-2-ylpiperazin-1-yl)methanone
[17] cis-(8-tert-butyl-1-oxa-2-azaspiro[4.5]dec-2-en-3-yl)-[4-(4-chloro-[1,2,5]thiadiazol-3-yl)piperazin-1-yl]methanone
[18] trans-(8-tert-butyl-1-oxa-2-azaspiro[4.5]dec-2-en-3-yl)-(6,7-dimethoxy-3,4-dihydro-1H-isoquinolin-2-yl)methanone
[19] cis-(8-tert-butyl-1-oxa-2-azaspiro[4.5]dec-2-en-3-yl)-(6,7-dimethoxy-3,4-dihydro-1H-isoquinolin-2-yl)methanone
[20] trans-(8-tert-butyl-1-oxa-2-azaspiro[4.5]dec-2-en-3-yl)-[4-(4-chloro-[1,2,5]thiadiazol-3-yl)piperazin-1-yl]methanone
[21] trans-(8-tert-butyl-1-oxa-2-azaspiro[4.5]dec-2-en-3-yl)-[4-(3-chloropyridin-2-yl)-[1,4]diazepan-1-yl]methanone
[22] cis-(8-tert-butyl-1-oxa-2-azaspiro[4.5]dec-2-en-3-yl)-[4-(3-chloropyridin-2-yl)-[1,4]diazepan-1-yl]methanone
[23] trans-8-tert-butyl-1-oxa-2-azaspiro[4.5]dec-2-ene-3-carboxylic acid (pyridin-4-ylmethyl)amide
[24] cis-8-tert-butyl-1-oxa-2-azaspiro[4.5]dec-2-ene-3-carboxylic acid (pyridin-4-ylmethyl)amide
[25] trans-8-tert-butyl-1-oxa-2-azaspiro[4.5]dec-2-ene-3-carboxylic acid-3-fluoro-4-methanesulphonylaminobenzylamide
[26] trans-8-tert-butyl-1-oxa-2-azaspiro[4.5]dec-2-ene-3-carboxylic acid-4-hydroxy-3-methoxybenzylamide
[27] cis-8-tert-butyl-1-oxa-2-azaspiro[4.5]dec-2-ene-3-carboxylic acid-4-hydroxy-3-methoxybenzylamide
[28] trans-(8-tert-butyl-1-oxa-2-azaspiro[4.5]dec-2-en-3-yl)-[4-(3-chloropyridin-2-yl)piperazin-1-yl]methanone
[29] cis-(8-tert-butyl-1-oxa-2-azaspiro[4.5]dec-2-en-3-yl)-[4-(3-chloropyridin-2-yl)piperazin-1-yl]methanone
[30] 3',4',4a',5',6',7',8',8a'-octahydro-1'H,4H-spiro[isoxazol-5,2'-naphthalene]-3-carboxylic acid-(4-tert-butylphenyl)amide
[31] 3',4',4a',5',6',7',8',8a'-octahydro-1'H,4H-spiro[isoxazol-5,2'-naphthalene]-3-carboxylic acid-(4-tert-butylbenzyl)amide
[32] 3',4',4a',5',6',7',8',8a'-octahydro-1'H,4H-spiro[isoxazol-5,2'-naphthalene]-3-carboxylic acid-3-fluoro-4-methanesulphonylaminobenzylamide
[33] 3-methyl-1-oxa-2-azaspiro[4.5]dec-2-ene-8-carboxylic acid-(4-tert-butylphenyl)amide
[34] 3-phenyl-3',4',4a',5',6',7',8',8a'-octahydro-1'H,4H-spiro[isoxazol-5,2'-naphthalene]
[35] 3,8-diphenyl-1-oxa-2-azaspiro[4.5]dec-2-ene
[36] 8 phenyl-3-p-tolyl-1-oxa-2-azaspiro[4.5]dec-2-ene
[37] 8 phenyl-3-(4-trifluormethylphenyl)-1-oxa-2-azaspiro[4.5]dec-2-ene
[38] 7,7,9,9-tetramethyl-3-phenyl-1-oxa-2-azaspiro[4.5]dec-2-ene
[39] 3-(4-tert-butylphenyl)-8 phenyl-1-oxa-2-azaspiro[4.5]dec-2-ene
[40] 4-tert-butyl-3-phenyl-3',4',4a',5',6',7',8',8a'-octahydro-1'H,4H-spiro[isoxazol-5,2'-naphthalene]
[41] 3-(4-tert-butylphenyl)-7,7,9,9-tetramethyl-1-oxa-2-azaspiro[4.5]dec-2-ene
[42] 8 phenyl-3-pyridin-2-yl-1-oxa-2-azaspiro[4.5]dec-2-ene
[43] 8-(1,1-dimethylpropyl)-3-pyridin-2-yl-1-oxa-2-azaspiro[4.5]dec-2-ene
[44] 3-(4-tert-butylphenyl)-8-(1,1-dimethylpropyl)-1-oxa-2-azaspiro[4.5]dec-2-ene
[45] 3-(4-tert-butylphenyl)-8-ethyl-1-oxa-2-azaspiro[4.5]dec-2-ene
[46] cis-[3-(4-tert-butylphenyl)-1-oxa-2-azaspiro[4.5]dec-2-en-8-yl]-[4-(3-chloropyridin-2-yl)piperazin-1-yl]methanone
[47] trans-[3-(4-tert-butylphenyl)-1-oxa-2-azaspiro[4.5]dec-2-en-8-yl]-[4-(3-chloropyridin-2-yl)piperazin-1-yl]methanone
[48] cis-[4-(3-chloropyridin-2-yl)piperazin-1-yl]-(3-phenyl-1-oxa-2-azaspiro[4.5]dec-2-en-8-yl)methanone
[49] trans-[4-(3-chloropyridin-2-yl)piperazin-1-yl]-(3-phenyl-1-oxa-2-azaspiro[4.5]dec-2-en-8-yl)methanone
[50] 3-phenyl-1-oxa-2-azaspiro[4.5]dec-2-ene-8-carboxylic acid-(4-tert-butylphenyl)amide
[51] 3-phenyl-1-oxa-2-azaspiro[4.5]dec-2-ene-8-carboxylic acid-cis-(4-tert-butylphenyl)amide
[52] 3-phenyl-1-oxa-2-azaspiro[4.5]dec-2-ene-8-carboxylic acid-cis-3-fluoro-4-methanesulphonylaminobenzylamide
[53] 3-phenyl-1-oxa-2-azaspiro[4.5]dec-2-ene-8-carboxylic acid-trans-3-fluoro-4-methanesulphonylaminobenzylamide
[54] 8-tert-butyl-1-oxa-2-azaspiro[4.5]dec-2-ene-3-carboxylic acid-(4-tert-butyl-phenyl)amide
[55] 3-phenyl-1-oxa-2-azaspiro[4.5]dec-2-ene-8-carboxylic acid-trans-(4-tert-butylphenyl)amide
[56] 8-tert-butyl-N-(4-(methylsulphonamido)benzyl)-1-oxa-2-azaspiro[4.5]dec-2-ene-3-carboxamide
[57] N-(4-tert-butylphenyl)-3-methyl-1-oxa-2-azaspiro[4.5]dec-2-ene-8-carboxamide hydrochloride
[58] ((5R,8R)-8-tert-butyl-1-oxa-2-azaspiro[4.5]dec-2-en-3-yl)(4-(3-chloropyridin-2-yl)-2,6-dimethylpiperazin-1-yl)methanone
[59] ((5S,8S)-8-tert-butyl-1-oxa-2-azaspiro[4.5]dec-2-en-3-yl)(4-(3-chloropyridin-2-yl)-2,6-dimethylpiperazin-1-yl)methanone
[60] ((5R,8R)-8-tert-butyl-1-oxa-2-azaspiro[4.5]dec-2-en-3-yl)(4-(3-chloropyridin-2-yl)-2-methylpiperazin-1-yl)methanone
[61] ((5S,8S)-8-tert-butyl-1-oxa-2-azaspiro[4.5]dec-2-en-3-yl)(4-(3-chloropyridin-2-yl)-2-methylpiperazin-1-yl)methanone
[62] (4-(3-chloropyridin-2-yl)piperazin-1-yl)(3-(3-methoxyphenyl)-1-oxa-2-azaspiro[4.5]dec-2-en-8-yl)methanone
[63] 3-(3-methoxyphenyl)-N-(4-(trifluoromethoxy)benzyl)-1-oxa-2-azaspiro[4.5]dec-2-ene-8-carboxamide
[64] N-(1H-indol-5-yl)-3-(3-methoxyphenyl)-1-oxa-2-azaspiro[4.5]dec-2-ene-8-carboxamide
[65] N-(3-fluoro-4-(methylsulphonamido)benzyl)-3-(3-methoxyphenyl)-1-oxa-2-azaspiro[4.5]dec-2-ene-8-carboxamide
[66] N-(4-tert-butylphenyl)-3-(3-methoxyphenyl)-1-oxa-2-azaspiro[4.5]dec-2-ene-8-carboxamide
[67] N-(2,3-dihydrobenzo[b][1,4]dioxin-6-yl)-3-(3-methoxyphenyl)-1-oxa-2-azaspiro[4.5]dec-2-ene-8-carboxamide
[68] N-(4-tert-butylphenyl)-3-(4-fluorophenyl)-1-oxa-2-azaspiro[4.5]dec-2-ene-8-carboxamide
[69] (5R,8R)-3-phenyl-N-((2-(piperidin-1-yl)-6-(trifluormethyl)pyridin-3-yl)methyl)-1-oxa-2-azaspiro[4.5]dec-2-ene-8-carboxamide

[70] (5R,8R)—N-((2-(4-methylpiperidin-1-yl)-6-(trifluoromethyl)pyridin-3-yl)methyl)-3-phenyl-1-oxa-2-azaspiro[4.5]dec-2-ene-8-carboxamide
[71] (5S,8S)—N-((2-(3-chloro-4-fluorophenyl)-6-(trifluoromethyl)pyridin-3-yl)methyl)-3-phenyl-1-oxa-2-azaspiro[4.5]dec-2-ene-8-carboxamide
[72] (5S,8S)—N-((2-(4-methylpiperidin-1-yl)-6-(trifluoromethyl)pyridin-3-yl)methyl)-3-phenyl-1-oxa-2-azaspiro[4.5]dec-2-ene-8-carboxamide
[73] (5S,8S)-3-phenyl-N-((2-(piperidin-1-yl)-6-(trifluoromethyl)pyridin-3-yl)methyl)-1-oxa-2-azaspiro[4.5]dec-2-ene-8-carboxamide
[74] (5R,8R)—N-(2,3-dihydrobenzo[b][1,4]dioxin-6-yl)-3-phenyl-1-oxa-2-azaspiro[4.5]dec-2-ene-8-carboxamide
[75] (5S,8S)—N-(2,3-dihydrobenzo[b][1,4]dioxin-6-yl)-3-phenyl-1-oxa-2-azaspiro[4.5]dec-2-ene-8-carboxamide
[79] 8-tert-butyl-N-(2,3-dihydrobenzo[b][1,4]dioxin-5-yl)-1-oxa-2-azaspiro[4.5]dec-2-ene-3-carboxamide
[80] N-(3-fluoro-4-(methylsulphonamido)benzyl)-8-tert-pentyl-1-oxa-2-azaspiro[4.5]dec-2-ene-3-carboxamide
[81] N-(2,3-dihydrobenzo[b][1,4]dioxin-5-yl)-8-tert-pentyl-1-oxa-2-azaspiro[4.5]dec-2-ene-3-carboxamide
[82] 8-cyclohexyl-N-(3-fluoro-4-(methylsulphonamido)benzyl)-1-oxa-2-azaspiro[4.5]dec-2-ene-3-carboxamide
[83] 8-tert-butyl-N-(7-hydroxynaphthalen-1-yl)-1-oxa-2-azaspiro[4.5]dec-2-ene-3-carboxamide
[84] N-(4-tert-butylphenyl)-3-(4-(3-chloropyridin-2-yl)piperazin-1-carbonyl)-1-oxa-2-azaspiro[4.5]dec-2-ene-8-carboxamide
[85] N-(4-tert-butylbenzyl)-3-(4-(3-chloropyridin-2-yl)piperazin-1-carbonyl)-1-oxa-2-azaspiro[4.5]dec-2-ene-8-carboxamide
[86] 8-tert-butyl-N-(5-hydroxynaphthalen-1-yl)-1-oxa-2-azaspiro[4.5]dec-2-ene-3-carboxamide
[87] 8-tert-butyl-N-(2-fluoro-5-(methylsulphonamido)phenyl)-1-oxa-2-azaspiro[4.5]dec-2-ene-3-carboxamide
[88] 8-tert-butyl-N-(2-fluoro-5-(N-(methylsulphonyl)methylsulphonamido)phenyl)-1-oxa-2-azaspiro[4.5]dec-2-ene-3-carboxamide
[89] 8-tert-butyl-N-(4-fluoro-3-(methylsulphonamido)phenyl)-1-oxa-2-azaspiro[4.5]dec-2-ene-3-carboxamide
[90] 8-tert-butyl-N-(3-fluoro-4-(methylsulphonamido)phenyl)-1-oxa-2-azaspiro[4.5]dec-2-ene-3-carboxamide
[91] 8-tert-butyl-N-(3-fluoro-4-(N-(methylsulphonyl)methylsulphonamido)phenyl)-1-oxa-2-azaspiro[4.5]dec-2-ene-3-carboxamide
[92] 8-tert-butyl-1-oxa-2-azaspiro[4.5]dec-2-ene-3-carboxylic acid-4-pentafluorosulphanylbenzylamide
and
[93] 3-(3-methoxyphenyl)-1-oxa-2-azaspiro[4.5]dec-2-ene-8-carboxylic acid-(4-pentafluorosulphanylphenyl)amide;
in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

Preference may also be given to substituted Spiro compounds according to the invention which in a FLIPR assay in a concentration of 10 µM display inhibition of the $Ca^{2+}$ ion inflow in dorsal root ganglia of rats of at least 10%, preferably of at least 30%, particularly preferably of at least 50%, most particularly preferably of at least 70%, even more preferably of at least 90%, compared to the maximum achievable inhibition of the $Ca^{2+}$ ion inflow with capsaicin in a concentration of 10 µM.

In the FLIPR assay, the $Ca^{2+}$ inflow is quantified using a $Ca^{2+}$-sensitive dye (type Fluo-4, Molecular Probes Europe BV, Leiden, Netherlands) in a fluorescent imaging plate reader (FLIPR, Molecular Devices, Sunnyvale, USA), as described hereinafter.

The present invention further relates to a process for preparing compounds according to the invention of the above-indicated general formula I in which at least one compound of general formula II,

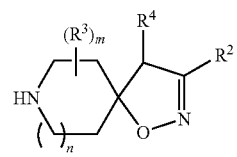

wherein n and $R^2$ to $R^9$ are as defined above and $R^1$ is as defined above except for a —C(=O)—$NR^{11}R^{12}$ group or represents —C(=O)—OR; wherein R represents a linear or branched $C_{1-6}$ alkyl radical; is reacted in a reaction medium in the presence of at least one base, preferably at least one organic base, with at least one compound of general formula III,

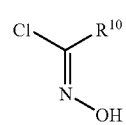

wherein $R^{10}$ is as defined above except for a —C(=O)—$NR^{13}R^{14}$ group or represents —C(=O)—OR; wherein R represents a linear or branched $C_{1-6}$ alkyl radical; to form at least one compound of general formula IV,

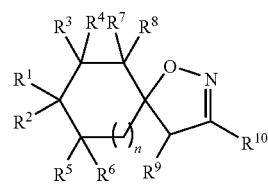

wherein n and $R^2$ to $R^9$ are as defined above, $R^1$ is as defined above except for a —C(=O)—$NR^{11}R^{12}$ group or represents —C(=O)—OR, and $R^{10}$ is as defined above except for a —C(=O)—$NR^{13}R^{14}$ group or represents —C(=O)—OR; wherein R independently of one another respectively represents a linear or branched $C_{1-6}$ alkyl radical; and the at least one compound of general formula IV is optionally purified and/or isolated;

and optionally at least one compound of general formula IV, wherein n and $R^2$ to $R^9$ are as defined above, $R^1$ represents —C(=O)—OR; wherein R is as defined above and $R^{10}$ is as defined above except for a —C(=O)—$NR^{13}R^{14}$ group; in a reaction medium in the presence of at least one base, preferably in the presence of at least one alkali metal hydroxide salt, particularly preferably in the presence of lithium hydroxide, to form at least one compound of general formula V,

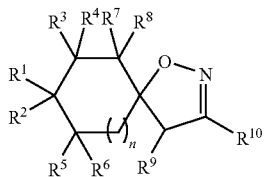

wherein n and $R^2$ to $R^9$ are as defined above, $R^1$ represents —C(=O)—OH and $R^{10}$ is as defined above except for a —C(=O)—$NR^{13}R^{14}$ group; is reacted and the at least one compound of general formula V is optionally purified and/or isolated;

and at least one compound of general formula V is reacted in a reaction medium in the presence of at least one coupling reagent, optionally in the presence of at least one base, with a compound of general formula $HNR^{11}R^{12}$, wherein $R^{11}$ and $R^{12}$ are as defined above, to form at least one compound of general formula I, wherein n and $R^2$ to $R^9$ are as defined above, $R^1$ represents a —C(=O)—$NR^{11}R^{12}$ group; wherein $R^{11}$ and $R^{12}$ are as defined above and $R^{10}$ is as defined above except for a —C(=O)—$NR^{13}R^{14}$ group; and the at least one compound of general formula I is optionally purified and/or isolated; or optionally at least one compound of general formula IV, wherein n and $R^2$ to $R^9$ are as defined above, $R^1$ is as defined above except for a —C(=O)—$NR^{11}R^{12}$ group and $R^{10}$ represents a —C(=O)—OR group; wherein R represents a linear or branched $C_{1-6}$ alkyl radical; is reacted in a reaction medium in the presence of at least one base, preferably in the presence of at least one alkali metal hydroxide salt, particularly preferably in the presence of lithium hydroxide, to form at least one compound of general formula VI,

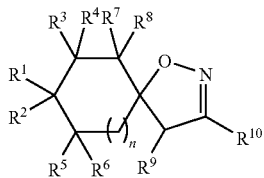

wherein n and $R^2$ to $R^9$ are as defined above, $R^1$ is as defined above except for a —C(=O)—$NR^{11}R^{12}$ group and $R^{10}$ represents —C(=O)—OH; and the at least one compound of general formula VI is optionally purified and/or isolated;

and at least one compound of general formula VI is reacted in a reaction medium in the presence of at least one coupling reagent, optionally in the presence of at least one base, with a compound of general formula $HNR^{13}R^{14}$, wherein $R^{13}$ and $R^{14}$ are as defined above, to form at least one compound of general formula I, wherein n and $R^2$ to $R^9$ are as defined above, $R^1$ is as defined above except for a —C(=O)—$NR^{11}R^{12}$ group and $R^1$ represents a —C(=O)—$NR^{13}R^{14}$ group; wherein $R^{13}$ and $R^{14}$ are as defined above; and the at least one compound of general formula I is optionally purified and/or isolated.

The processes according to the invention for preparing substituted spiro compounds of the above-indicated general formula I are also represented in the following Diagrams 1, 2 and 3.

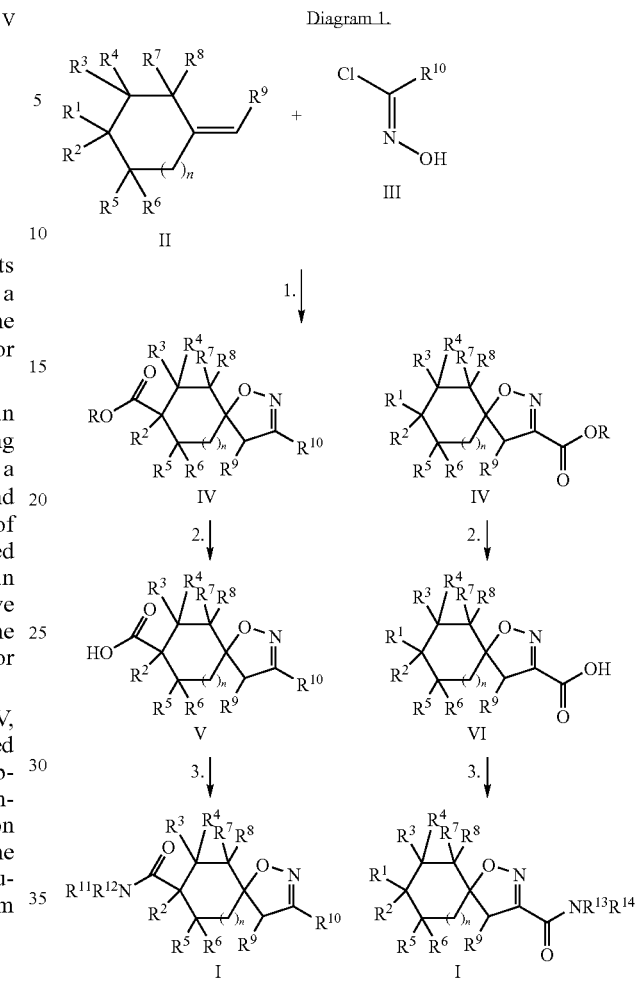

Diagram 1.

In step 1, compounds of general formula II are reacted in a reaction medium, preferably in a reaction medium selected from the group consisting of methanol, tetrahydrofuran, dichloromethane and corresponding mixtures, in the presence of at least one base, preferably in the presence of at least one base selected from the group consisting of sodium hydrogen carbonate, lithium hydroxide, triethylamine or N-diisopropylethylamine, with compounds of general formula III at temperatures between 0° C. and 100° C., to form compounds of general formula IV.

In step 2, compounds of general formula IV, wherein $R^1$ or $R^{10}$ represents —C(=O)—R, are reacted in a reaction medium, preferably in a reaction medium selected from the group consisting of methanol, ethanol, water, isopropanol and corresponding mixtures, in the presence of at least one base, preferably in the presence of lithium hydroxide monohydrate, at temperatures between 0° C. and 50° C. to form compounds of general formula II.

In step 3, compounds of the above-indicated general formula V are reacted with amines of general formula $HNR^{11}R^{12}$ or compounds of the above-indicated formula VI are reacted with amines of general formula $HNR^{13}R^{14}$ in a reaction medium, preferably selected from the group consisting of diethyl ether, tetrahydrofuran, acetonitrile, methanol, ethanol, dimethylformamide, dichloromethane and corresponding mixtures, optionally in the presence of at least one coupling reagent, preferably selected from the group consisting of 1-benzotriazolyloxy-tris-(dimethylamino)phosphonium hexafluorophosphate (BOP), dicyclohexylcarbodiimide (DCC), N,N'-carbonyldiimidazole, N,N'-diisopropylcarbodiimide, N'-(3-dimethylaminopropyl)-N-ethylcarbodiimide (EDCI), N-[(dimethylamino)-1H-1,2,3-triazolo[4,5-b]pyridin-1-ylmethylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-hydroxybenzotriazole (HOBt) and 1-hydroxy-7-azabenzotriazole (HOAt), optionally in the presence of at least one inorganic base, preferably selected from the group consisting of potassium carbonate and caesium carbonate, or an organic base, preferably selected from the group consisting of triethylamine, 4-methylmorpholine, pyridine, N,N-dimethylaminopyridine and diisopropylethylamine, preferably at temperatures of −70° C. to 100° C., to form compounds of general formula I, wherein $R^1$ represents —C(═O)—$NHR^{11}R^{12}$ or $R^{10}$ represents —C(═O)—$NHR^{13}R^{14}$.

The compounds of general formula II may be obtained as illustrated in Diagram 2.

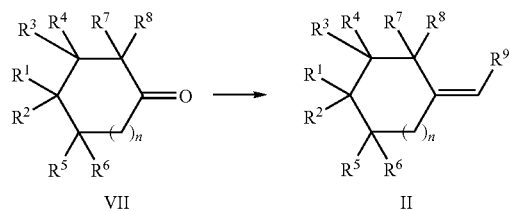

Diagram 2.

Compounds of general formula VII, wherein n and $R^1$ to $R^8$ are as defined above, are reacted in a reaction medium, preferably in a reaction medium selected from the group consisting of tetrahydrofuran, toluene, diethyl ether and corresponding mixtures, with a reagent for converting carbonyl groups into double bonds, preferably with a Wittig reagent of general formula $R_3P(CH_2)R^9X$; wherein R represents an aryl radical, X represents a halogen atom and $R^9$ is as defined above; or a Wittig-Horner reagent of general formula $(RO)_2$—P(═O)—$(CH_2)$—$R^9$, wherein R represents an aryl radical and $R^9$ is as defined above, particularly preferably with methyltriphenylphosphonium bromide, at temperatures between 0° C. and 30° C. in the presence of a base, preferably in the presence of an alkali metal alcoholate salt, particularly preferably in the presence of potassium tert-butylate, to form compounds of general formula II.

The compounds of general formula III may be obtained as illustrated in Diagram 3.

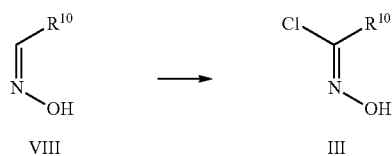

Diagram 3.

Compounds of general formula VIII, wherein $R^{10}$ is as defined above or represents —C(═O)—OR, are reacted in a reaction medium, preferably in a reaction medium selected from the group consisting of tetrahydrofuran, dimethylformamide, dichloromethane, toluene, diethyl ether and corresponding mixtures, with N-chlorosuccinimide at temperatures between 0 and 50° C. to form compounds of general formula III.

The compounds of the above-indicated formulae $R_3P(CH_2)R^9X$, $(RO)_2$—P(═O)—$(CH_2)$—$R^9$, $HNR^{11}R^{12}$, $HNR^{13}R^{14}$, VII and VIII are each commercially available and can also be prepared using conventional processes known to a person skilled in the art.

The above-described reactions can each be carried out under the conventional conditions with which a person skilled in the art is familiar, for example with regard to pressure or the order in which the components are added. If appropriate, a person skilled in the art can determine by simple preliminary tests the procedure which is optimal under the respective conditions. The intermediate and end products obtained as a result of the above-described reactions can each, if it is desirable and/or necessary, be purified and/or isolated using conventional methods known to a person skilled in the art. Suitable purification processes include, for example, extraction processes and chromatographic processes such as column chromatography or preparative chromatography. All of the above-described process steps and in each case also the purification and/or isolation of intermediate or end products can be carried out partly or completely under an inert gas atmosphere, preferably under a nitrogen atmosphere.

The substituted spiro compounds according to the invention of the above-mentioned general formula I and Ia, referred to hereinafter simply as spiro compounds of general formula I, and corresponding stereoisomers can be isolated both in the form of their free bases, their free acids and also in the form of corresponding salts, in particular physiologically compatible salts. The free bases of the respective substituted spiro compounds according to the invention of the above-mentioned general formula I and of corresponding stereoisomers can, for example, be converted by reaction with an inorganic or organic acid, preferably with hydrochloric acid, hydrobromic acid, sulphuric acid, phosphoric acid, methanesulphonic acid, p-toluenesulphonic acid, carbonic acid, formic acid, acetic acid, oxalic acid, succinic acid, tartaric acid, mandelic acid, fumaric acid, lactic acid, citric acid, glutamic acid or aspartic acid, into the corresponding salts, preferably physiologically compatible salts. The free bases of the respective substituted spiro compounds of the above-mentioned general formula I and of corresponding stereoisomers can also be converted with the free acid or a salt of a sugar substitute, such as, for example, saccharin, cyclamate or acesulfame, into the corresponding physiologically compatible salts. Accordingly, the free acids of the substituted spiro compounds of the above-mentioned general formula I and of corresponding stereoisomers can be converted by reaction with a suitable base into the corresponding physiologically compatible salts. Examples include the alkali metal salts, alkaline-earth metal salts or ammonium salts $[NH_xR_{4-x}]^+$, wherein x=0, 1, 2, 3 or 4 and R represents a linear or branched $C_{1-4}$ alkyl radical.

The substituted spiro compounds according to the invention of the above-mentioned general formula I and of corresponding stereoisomers can optionally also be obtained, like the corresponding acids, the corresponding bases or salts of these compounds, using conventional methods known to a person skilled in the art in the form of their solvates, preferably in the form of their hydrates.

If the substituted spiro compounds according to the invention of the above-mentioned general formula I are obtained after preparation thereof in the form of a mixture of their stereoisomers, preferably in the form of their racemates or other mixtures of their various enantiomers and/or diastereomers which can be separated and optionally isolated using conventional methods known to a person skilled in the art. Examples include chromatographic separation processes, in particular liquid chromatography processes under normal pressure or under elevated pressure, preferably MPLC and HPLC processes, and fractionated crystallisation processes. These allow, in particular, the separation from one another of individual enantiomers of diastereomeric salts formed, for example, by means of HPLC on a chiral stationary phase or by means of crystallisation with chiral acids, for example (+)-tartaric acid, (−)-tartaric acid or (+)-10-camphorsulphonic acid.

The substituted spiro compounds according to the invention of the above-mentioned general formula I and corresponding stereoisomers and in each case the corresponding acids, bases, salts and solvates are toxicologically safe and are therefore suitable as pharmaceutical active ingredients in medicaments.

The present invention therefore further relates to a medicament comprising at least one spiro compound according to the invention of the above-indicated general formula I, in each case optionally in the form of one of its pure stereoisomers, in particular enantiomers or diastereomers, its racemates or in the form of a mixture of stereoisomers, in particular of enantiomers and/or diastereomers, in any desired mixing ratio, or respectively in the form of a corresponding salt, or respectively in the form of a corresponding solvate, and optionally one or more pharmaceutically compatible adjuvants.

These medicaments according to the invention are suitable, in particular, for vanilloid receptor 1 (VR1/TRPV1) regulation, preferably for vanilloid receptor 1 (VR1/TRPV1) inhibition and/or for vanilloid receptor 1 (VR1/TRPV1) stimulation.

Also preferably, the medicaments according to the invention are suitable for the prophylaxis and/or treatment of disturbances or diseases transmitted, at least in some cases, by vanilloid receptors 1.

Preferably, the medicament according to the invention is suitable for the treatment and/or prophylaxis of one or more diseases selected from the group consisting of pain, preferably of pain selected from the group consisting of acute pain, chronic pain, neuropathic pain and visceral pain; arthralgia; migraine; depression; neuropathy; nerve injuries; neurodegenerative diseases, preferably selected from the group consisting of multiple sclerosis, Alzheimer's disease, Parkinson's disease and Huntington's disease; cognitive dysfunctions, preferably cognitive deficiencies, particularly preferably paramnesia; epilepsy; respiratory diseases, preferably selected from the group consisting of asthma and pneumonia; coughing; urinary incontinence; OAB (overactive bladder); stomach ulcers; irritable bowel syndrome; strokes; irritations of the eyes; irritations of the skin; neurotic skin diseases; inflammatory diseases, preferably intestinal inflammations; diarrhea; pruritus; eating disorders, preferably selected from the group consisting of bulimia, cachexia, anorexia and obesity; medication dependency; medication abuse; withdrawal symptoms in medication dependency; development of tolerance to medication, preferably to natural or synthetic opioids; drug addiction; drug abuse; withdrawal symptoms in drug addiction; alcohol addiction; alcohol abuse and withdrawal symptoms in alcohol addiction; for diuresis; for antinatriuresis; for influencing the cardiovascular system; for increasing vigilance; for increasing libido; for modulating motor activity; for anxiolysis; for local anaesthetics and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Particularly preferably, the medicament according to the invention is suitable for the treatment and/or prophylaxis of one or more diseases selected from the group consisting of pain, preferably of pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiencies, particularly preferably paramnesia; urinary incontinence; OAB (overactive bladder); medication dependency; medication abuse; withdrawal symptoms in medication dependency; development of tolerance to medication, preferably development of tolerance to natural or synthetic opioids; drug addiction; drug abuse; withdrawal symptoms in drug addiction; alcohol addiction; alcohol abuse and withdrawal symptoms in alcohol addiction.

Most particularly Preferably, the medicament according to the invention is suitable for the treatment and/or prophylaxis of pain, preferably of pain selected from the group consisting of acute pain, chronic pain, neuropathic pain and visceral pain, and/or urinary incontinence.

The present invention further relates to the use of at least one substituted spiro compound according to the invention, including the compounds excluded hereinbefore, and optionally of one or more pharmaceutically compatible adjuvants for producing a medicament for vanilloid receptor 1 (VR1/TRPV1) regulation, preferably for vanilloid receptor 1 (VR1/TRPV1) inhibition and/or for vanilloid receptor 1 (VR1/TRPV1) stimulation.

Preferred is the use of at least one substituted spiro compound according to the invention, including the compounds excluded hereinbefore, and optionally of one or more pharmaceutically compatible adjuvants for producing a medicament for the prophylaxis and/or treatment of disturbances or diseases transmitted, at least in some cases, by vanilloid receptors 1.

Particularly preferred is the use of at least one substituted spiro compound according to the invention, including the compounds excluded hereinbefore, and optionally of one or more pharmaceutically compatible adjuvants for producing a medicament for the treatment and/or prophylaxis of one or more diseases selected from the group consisting of pain, preferably of pain selected from the group consisting of acute pain, chronic pain, neuropathic pain and visceral pain; arthralgia; migraine; depression; neuropathy; nerve injuries; neurodegenerative diseases, preferably selected from the group consisting of multiple sclerosis, Alzheimer's disease, Parkinson's disease and Huntington's disease; cognitive dysfunctions, preferably cognitive deficiencies, particularly preferably paramnesia; epilepsy; urinary incontinence; OAB (overactive bladder); stomach ulcers; irritable bowel syndrome; strokes; diarrhea; pruritus; eating disorders, preferably selected from the group consisting of bulimia, cachexia, anorexia and obesity; medication dependency; medication abuse; withdrawal symptoms in medication dependency; development of tolerance to medication, preferably to natural or synthetic opioids; drug addiction; drug abuse; withdrawal symptoms in drug addiction; alcohol addiction; alcohol abuse and withdrawal symptoms in alcohol addiction; for diuresis; for antinatriuresis; for influencing the cardiovascular system;

for increasing vigilance; for increasing libido; for modulating motor activity; for anxiolysis; for local anaesthetics and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Also particularly preferred is the use of at least one substituted spiro compound according to the invention and optionally of one or more pharmaceutically compatible adjuvants for producing a medicament for the treatment and/or prophylaxis of one or more diseases selected from the group consisting of respiratory diseases, preferably selected from the group consisting of asthma and pneumonia; coughing; irritations of the eyes; irritations of the skin; neurotic skin diseases; and inflammatory diseases, preferably intestinal inflammations.

Most particularly preferred is the use of at least one substituted spiro compound according to the invention, including the compounds excluded hereinbefore, and optionally of one or more pharmaceutically compatible adjuvants for producing a medicament for the treatment and/or prophylaxis of one or more diseases selected from the group consisting of pain, preferably of pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiencies, particularly preferably paramnesia; urinary incontinence; OAB (overactive bladder); medication dependency; medication abuse; withdrawal symptoms in medication dependency; development of tolerance to medication, preferably development of tolerance to natural or synthetic opioids; drug addiction; drug abuse; withdrawal symptoms in drug addiction; alcohol addiction; alcohol abuse and withdrawal symptoms in alcohol addiction.

Still more preferred is the use of at least one substituted spiro compound according to the invention, including the compounds excluded hereinbefore, and optionally of one or more pharmaceutically compatible adjuvants for producing a medicament for the treatment and/or prophylaxis of pain, preferably selected from the group consisting of acute pain, chronic pain, neuropathic pain and visceral pain, and/or urinary incontinence.

The medicament according to the invention is suitable for administration to adults and children, including toddlers and babies.

The medicament according to the invention can be provided as a liquid, semisolid or solid pharmaceutical dosage form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, optionally compressed to form tablets, introduced into capsules or suspended in a liquid, and also be administered as such.

In addition to at least one substituted spiro compound of the above-indicated general formula I, optionally in the form of one of its pure stereoisomers, in particular enantiomers or diastereomers, its racemate or in the form of mixtures of stereoisomers, in particular of enantiomers or diastereomers, in any desired mixing ratio, or optionally in the form of a corresponding salt or respectively in the form of a corresponding solvate, the medicament according to the invention conventionally comprises further physiologically compatible pharmaceutical adjuvants which can be selected, for example, from the group consisting of excipients, fillers, solvents, diluting agents, surface-active substances, dyes, preservatives, disintegrants, slip additives, lubricants, aroma substances and binding agents.

The selection of the physiologically compatible adjuvants and the amounts thereof to be used are dependent on whether the medicament is to be administered orally, subcutaneously, parenterally, intravenously, intraperitoneally, intradermally, intramuscularly, intranasally, buccally, rectally or locally, for example to infections on the skin which mucous membranes and on the eyes. Preferably suitable for oral administration are preparations in the form of tablets, dragées, capsules, granules, pellets, drops, juices and syrups, for parenteral, solutions to be administered topically and by inhalation, suspensions, easily reconstitutable dry preparations and sprays.

The substituted spiro compounds according to the invention used in the medicament according to the invention in a repository in dissolved form or in a plaster, optionally with the addition of means promoting skin penetration, are suitable percutaneous administration preparations. Preparation forms to be administered orally or percutaneously can also release the respective substituted spiro compound according to the invention in a delayed manner.

The medicaments according to the invention are prepared using conventional means, devices, methods and processes known in the art such as are described, for example, in "Remington's Pharmaceutical Sciences", A. R. Gennaro (Editor), 17th edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted spiro compounds according to the invention of the above-indicated general formula I may vary and is, for example, dependent on the patient's weight or age and on the type of administration, indication and the severity of the disease. Conventionally, 0.001 to 100 mg/kg, preferably 0.05 to 75 mg/kg, particularly preferably 0.05 to 50 mg/kg of the patient's body weight of at least one compound of this type according to the invention are administered.

Pharmacological Methods:
I. Functional Testing Carried Out on the Vanilloid Receptor 1 (VR1/TRPV1 Receptor)

The agonistic or antagonistic effect of the substances to be tested can be determined on the rat-species vanilloid receptor 1 (VR1/TRPV1) using the following assay. According to this assay, the $Ca^{2+}$ inflow is quantified through the receptor channel using a $Ca^{2+}$-sensitive dye (type Fluo-4, Molecular Probes Europe BV, Leiden, Netherlands) in a fluorescent imaging plate reader (FLIPR, Molecular Devices, Sunnyvale, USA).
Method:
Complete medium: 50 mL HAMS F12 nutrient mixture (Gibco Invitrogen GmbH, Karlsruhe, Germany) with
10% by volume of FCS (foetal calf serum, Gibco Invitrogen GmbH, Karlsruhe, Germany, heat-activated);
2 mM L-glutamine (Sigma, Munich, Germany);
1% by weight of AA solution (antibiotic/antimyotic solution, PAA, Pasching, Austria) and 25 ng/ml NGF medium (2.5 S, Gibco Invitrogen GmbH, Karlsruhe, Germany)

Cell culture plate: Poly-D-lysine-coated, black 96 well plates having a clear base (96 well black/clear plate, BD Biosciences, Heidelberg, Germany) were additionally coated with laminin (Gibco Invitrogen GmbH, Karlsruhe, Germany), the laminin being diluted with PBS (Ca—Mg-free PBS, Gibco Invitrogen GmbH, Karlsruhe, Germany) to a concentration of 100 µg/mL. Aliquots having a laminin concentration of 100 µg/mL were removed and stored at −20° C. The aliquots were diluted with PBS in a ratio of 1:10 to 10 µg/mL laminin and in each case 50 µL of the solution were pipetted into a recess in the cell culture plate. The cell culture plates were incubated for at least two hours at 37° C., the excess solution was removed by suction-filtration and the recesses were each washed twice with PBS. The coated cell culture plates were stored with excess PBS which was not removed until just before the feeding of the cells.

Preparation of the Cells:

The vertebral column was removed from decapitated rats and placed immediately into cold HBSS buffer (Hank's buffered saline solution, Gibco Invitrogen GmbH, Karlsruhe, Germany), i.e. buffer located in an ice bath, mixed with 1% by volume (percent by volume) of an AA solution (antibiotic/antimyotic solution, PAA, Pasching, Austria). The vertebral column was cut longitudinally and removed together with fasciae from the vertebral canal. Subsequently, the dorsal root ganglia (DRG) were removed and again stored in cold HBSS buffer mixed with 1% by volume of an AA solution. The DRG, from which all blood remnants and spinal nerves had been removed, were transferred in each case to 500 µL of cold type 2 collagenase (PAA, Pasching, Austria) and incubated for 35 minutes at 37° C. After the addition of 2.5% by volume of trypsin (PAA, Pasching, Austria), incubation was continued for 10 minutes at 37° C. After complete incubation, the enzyme solution was carefully pipetted off and 500 µL of complete medium were added to each of the remaining DRG. The DRG were in each case suspended several times, drawn through cannulae No. 1, No. 12 and No. 16 using a syringe and transferred to a 50 mL Falcon tube which was filled up to 15 mL with complete medium. The contents of each Falcon tube was in each case filtered through a 70 µm Falcon filter element and centrifuged for 10 minutes at 1,200 rpm and room temperature. The resulting pellet was in each case taken up in 250 µL of complete medium and the number of cells determined.

The number of cells in the suspension was set to $3\times10^5$ per mL and 150 µL of this suspension were in each case introduced into a recess in the cell culture plates coated as described hereinbefore. In the incubator the plates were left for two to three days at 37° C., 5% by volume of $CO_2$ and 95% relative humidity.

Subsequently, the cells were loaded with 2 µM of Fluo-4 and 0.01% by volume of Pluronic F127 (Molecular Probes Europe BV, Leiden, Netherlands) in HBSS buffer (Hank's buffered saline solution, Gibco Invitrogen GmbH, Karlsruhe, Germany) for 30 min at 37° C., washed 3 times with HBSS buffer and after further incubation for 15 minutes at room temperature used for $Ca^{2+}$ measurement in a FLIPR assay. The $Ca^{2+}$-dependent fluorescence was measured before and after the addition of substances ($\lambda ex=488$ nm, $\lambda em=540$ nm). Quantification was carried out by measuring the highest fluorescence intensity (FC, Fluorescence Counts) over time.

FLIPR Assay:

The FLIPR protocol consists of 2 substance additions. First the compounds to be tested (10 µM) were pipetted onto the cells and the $Ca^{2+}$ inflow was compared with the control (capsaicin 10 µM). This provides the result in % activation based on the $Ca^{2+}$ signal after the addition of 10 µM capsaicin (CP). After 5 minutes' incubation, 100 nM of capsaicin were administered and the $Ca^{2+}$ inflow was also determined.

Desensitising agonists and antagonists led to suppression of the $Ca^{2+}$ inflow. The % inhibition was calculated compared to the maximum achievable inhibition with 10 µM of capsaicin.

Triple analyses (n=3) were carried out and repeated in at least 3 independent experiments (N=4).

II. Functional Testing Carried Out on the Vanilloid Receptor (VR1)

The agonistic or antagonistic effect of the substances to be tested can also be determined on the vanilloid receptor (VR1) using the following assay. According to this assay, the $Ca^{2+}$ inflow is quantified through the channel using a $Ca^{2+}$-sensitive dye (type Fluo-4, Molecular Probes Europe BV, Leiden, Netherlands) in a fluorescent imaging plate reader (FLIPR, Molecular Devices, Sunnyvale, USA).

Method:

Chinese hamster ovary cells (CHO K1 cells, European Collection of Cell Cultures (ECACC) United Kingdom) were stably transfected with the VR1 gene. For functional testing, these cells were plated out on poly-D-lysine-coated black 96 well plates having a clear base (BD Biosciences, Heidelberg, Germany) at a density of 25,000 cells/well. The cells were incubated overnight at 37° C. and 5% $CO_2$ in a culture medium (Ham's F12 nutrient mixture, 10% by volume of FCS (foetal calf serum), 18 µg/ml L-proline). The next day the cells were incubated with Fluo-4 (Fluo-4 2 µM, 0.01% by volume of Pluronic F127, Molecular Probes in HBSS (Hank's buffered saline solution), Gibco Invitrogen GmbH, Karlsruhe, Germany) for 30 minutes at 37° C. Subsequently, the plates were washed three times with HBSS buffer and after further incubation for 15 minutes at room temperature used for $Ca^{2+}$ measurement in a FLIPR assay. The $Ca^{2+}$-dependent fluorescence was measured before and after addition of the substances to be tested ($\lambda ex$ wavelength=488 nm, $\lambda em=540$ nm). Quantification was carried out by measuring the highest fluorescence intensity (FC, Fluorescence Counts) over time.

FLIPR Assay:

The FLIPR protocol consists of 2 substance additions. First the compounds to be tested (10 µM) were pipetted onto the cells and the $Ca^{2+}$ inflow was compared with the control (capsaicin 10 µM) (% activation based on the $Ca^{2+}$ signal after the addition of 10 µM capsaicin). After 5 minutes' incubation, 100 nM of capsaicin were administered and the $Ca^{2+}$ inflow was also determined.

Desensitising agonists and antagonists led to suppression of the $Ca^{2+}$ inflow. The % inhibition was calculated compared to the maximum achievable inhibition with 10 µM of capsaicin.

III. Formalin Test Carried Out on Mice

In the formalin test, the testing to determine the antinociceptive effect of the compounds according to the invention was carried out on male mice (NMRI, 20 to 30 g body weight, Iffa, Credo, Belgium).

In the formalin test as described by D. Dubuisson et al., Pain 1977, 4, 161-174, a distinction is drawn between the first (early) phase (0 to 15 minutes after the injection of formalin) and the second (late) phase (15 to 60 minutes after the injection of formalin). The early phase, as an immediate reaction to the injection of formalin, is a model of acute pain, whereas the late phase is regarded as a model of persistent (chronic) pain (T. J. Coderre et al., Pain 1993, 52, 259-285). The corresponding descriptions in the literature are introduced herewith by way of reference and form part of the disclosure.

The compounds according to the invention were tested in the second phase of the formalin test to obtain information about the effects of substances on chronic/inflammatory pain.

The moment at which the compounds according to the invention were administered before the injection of formalin was selected as a function of the type of administration. 10 mg of the test substances/kg of body weight were administered intravenously 5 minutes before the injection of formalin which was carried out by a single subcutaneous injection of formalin (20 μL, 1% aqueous solution) into the dorsal side of the right hind paw, thus inducing in free moving test animals a nociceptive reaction which manifests itself in marked licking and biting of the respective paw.

Subsequently, the nociceptive behaviour was continuously detected by observing the animals over a test period of three minutes in the second (late) phase of the formalin test (21 to 24 minutes after the injection of formalin). The pain behaviour was quantified by adding up the seconds over which the animals displayed licking and biting of the respective paw during the test period.

The comparison was carried out in each case with control animals which were given vehicles (0.9% aqueous sodium chloride solution) instead of the compounds according to the invention before the administration of formalin. Based on the quantification of the pain behaviour, the effect of the substance was determined in the formalin test as a percentage change relative to the corresponding control.

After the injection of substances having an antinociceptive effect in the formalin test, the described behaviour of the animals, i.e. licking and biting, was reduced or eliminated.

IV. Testing of Analgesic Efficacy in the Writhing Test

The testing of analgesic efficacy in the compounds according to the invention of general formula I was carried out by phenylquinone-induced writhing in mice (modified in accordance with I. C. Hendershot and J. Forsaith (1959), J. Pharmacol. Exp. Ther. 125, 237-240). The corresponding description in the literature is introduced herewith by way of reference and forms part of the disclosure.

Male NMRI mice weighing from 25 to 30 g were used for this purpose. 10 minutes after intravenous administration of the compounds to be tested, groups of 10 animals per compound dose received 0.3 ml/mouse of a 0.02% aqueous solution of phenylquinone (phenylbenzoquinone, Sigma, Deisenhofen, Germany; solution prepared by adding 5% by weight of ethanol and stored in a water bath at 45° C.) administered intraperitoneally. The animals were placed individually into observation cages. A pushbutton counter was used to record the number of pain-induced stretching movements (what are known as writhing reactions=straightening of the torso with stretching of the rear extremities) for 5 to 20 minutes after phenylquinone administration. The control was provided by animals which had received only physiological saline solution. All of the compounds were tested at the standard dosage of 10 mg/kg.

The invention will be described hereinafter with reference to a few examples. This description is intended merely by way of example and does not limit the general idea of the invention.

EXAMPLES

The yields of the compounds prepared are not optimised. All temperatures are uncorrected.

ABBREVIATIONS abs. absolute
aq. aqueous
eq. equivalent amount of substance
CDI N,N'-carbonyldiimidazole
DCM dichloromethane
DMF dimethylformamide
EtOAc ethyl acetate
EtOH ethanol
sat. saturated
MeOH methanol
RT room temperature
THF tetrahydrofuran The chemicals and solvents used were purchased from the conventional suppliers (Acros, Avocado, Aldrich, Bachem, Fluka, Lancaster, Maybridge, Merck, Sigma, TCI, etc.) or synthesised using the methods known to a person skilled in the art.

The stationary phase used for the column chromatography was silica gel 60 (0.040-0.063 mm) from E. Merck, Darmstadt.

The thin-layer chromatographic tests were carried out using HPTLC precoated plates, silica gel 60 F 254, from E. Merck, Darmstadt.

The mixing ratios of solvents, mobile solvents or for chromatographic tests are in each case specified in volume/volume.

The analysis was carried out by mass spectroscopy and NMR.

1.a. Synthesis of
1-tert-butyl-4-methylenecyclohexane

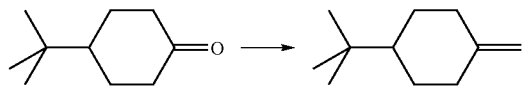

Methyltriphenylphosphonium bromide (17.4 g, 48.6 mmol) was placed in abs. diethyl ether (106 ml) under a nitrogen atmosphere. Potassium tert-butylate (5.0 g, 45.4 mmol) was slowly added at 0° C. After 30 min, 4-tert-butylcyclohexanone (5.0 g, 32.4 mmol) as a solution in diethyl ether (10 ml) was slowly added dropwise, again at 0° C. The reaction mixture was stirred overnight at RT. For working up, the reaction mixture was cooled in an ice bath and mixed with sat. aq. NH₄Cl solution. The phases were separated and the aqueous phase was shaken out several times with diethyl ether. The combined organic phases were dried over magnesium sulphate and the solvent was removed under vacuum. After column chromatography (silica gel, hexane/EtOAc 2:1), the desired compound 1-tert-butyl-4-methylenecyclohexane was obtained as a colourless liquid (3.93 g, 80% of the theoretical amount).

1.b. Synthesis of
1-(1,1-dimethylpropyl)-4-methylenecyclohexane

A solution of potassium tert-butylate (4.2 g, 37.6 mmol) in abs. THF (40 ml) was added dropwise to a suspension of methyltriphenylphosphonium bromide (15 g, 42 mmol) in abs. THF (40 ml) at 0° C. under argon within 30 min. There formed a yellow mixture which was stirred for 30 min at 0° C. Within 20 min, the ketone 4-(1,1-dimethylpropyl)cyclohexanone (5.04 g, 30 mmol), dissolved in abs. THF (20 ml) was subsequently added at 0° C. The mixture was stirred for 30 min while being cooled with ice, the ice bath removed and the mixture stirred for 1.5 h at RT. For working up the mixture, the solvent was removed under vacuum and the remaining yellow crystal mass taken up in a mixture of sat. aq. NH₄Cl solution (150 ml) and EtOAc (180 ml). The phases were separated and the aqueous phase was extracted with EtOAc (2×150 ml). The combined organic phases were dried and concentrated. The residue was washed with cyclohexane (3×60 ml) and the undissolved triphenylphosphin oxides were separated off by filtration. After concentration of the filtrate, the crude product remained as a colourless oil. After chromatographic purification of the crude product [silica gel 60 (100 g); cyclohexane (1 l)], the olefin 1-(1,1-dimethylpropyl)-4-methylenecyclohexane was isolated as a colourless oil in a yield of 99% (4.9 g).

1.c. Synthesis of 4-methylenebicyclohexyl

A solution of potassium tert-butylate (3.45 g, 31 mmol) in abs. THF (40 ml) was added dropwise to a suspension of methyltriphenylphosphonium bromide (12.0 g, 34 mmol) in abs. THF (70 ml) at 0° C. under argon within 30 min. There formed a yellow mixture which was stirred for 30 min at 0° C. 4-Cyclohexylcyclohexanone (4.32 g, 24 mmol), dissolved in abs. THF (30 ml) was subsequently added within 20 min at 0° C. The mixture was stirred for 30 min while being cooled with ice and for 1.5 h at RT. For working up the mixture, the solvent was removed under vacuum and the remaining yellow crystal mass taken up in a mixture of sat. aq. $NH_4Cl$ solution (50 ml) and EtOAc (60 ml). Between the phases there remained undissolved a portion of the triphenylphosphin oxide formed which was separated off by filtration. The phases were separated from the filtrate and the aqueous phase was extracted with EtOAc (2×60 ml). The combined organic phases were dried and concentrated. The residue was washed with cyclohexane (3×80 ml) and the undissolved triphenylphosphin oxide separated off by filtration. After concentration of the filtrate, the crude product of the olefin 4-methylenebicyclohexyl remained as a colourless oil. After chromatographic purification of the crude product [silica gel 60 (70 g); cyclohexane (400 ml)], the olefin 4-methylenebicyclohexyl was isolated as a colourless oil in a yield of 92% (3.94 g).

2.a. Synthesis of 8-tert-butyl-1-oxa-2-azaspiro[4.5]dec-2-ene-3-carboxylic acid ethyl ester A solution of 2-chloro-2-hydroxyiminoacetic acid ethyl ester (2.2 g, 14.6 mmol) in DCM (20 ml) was slowly added dropwise at 0° C. to a solution of 1-tert-butyl-4-methylenecyclohexane (740 mg, 4.86 mmol) in DCM (20 ml). Subsequently, a solution of triethylamine (1.5 ml) in DCM (10 ml) was slowly added dropwise at 0° C. and the resulting mixture was stirred overnight at RT. The reaction mixture was diluted with water. The aqueous phase was extracted several times with DMC. The combined organic phases were dried and the solvent was removed under vacuum. After purification of the residue (silica gel, hexane/ether 2:1) by column chromatography, the desired product 8-tert-butyl-1-oxa-2-azaspiro[4.5]dec-2-ene-3-carboxylic acid ethyl ester was obtained as a yellowish liquid (1.21 g, 93% of the theoretical amount).

2.b. 8-(1,1-dimethylpropyl)-1-oxa-2-azaspiro[4.5]dec-2-ene-3-carboxylic acid ethyl ester A solution of the olefin 1-(1,1-dimethylpropyl)-4-methylenecyclohexane (4.9 g, 30 mmol) in abs. DCM (140 ml) was mixed with 2-chloro-2-hydroxyiminoacetic acid ethyl ester (22.74 g, 150 mmol) under argon and while being cooled with ice. The solution was subsequently cooled down to −5° C. Within 1 h, a solution of triethylamine (20.9 ml, 15.2 g, 150 mmol) in abs. DCM (70 ml) was added dropwise in such a way that the internal temperature did not exceed 0° C. Subsequently, the mixture was stirred for 3 d at RT. Triethylamine hydrochloride was gradually precipitated. For working up, the reaction mixture was washed with 10% aq. citric acid solution (3×70 ml) and with sat. aq. $NaHCO_3$ solution (70 ml). The organic phase was dried and concentrated. There was obtained a yellow oil (19.9 g) which was separated by column chromatography [silica gel 60 (300 g); EtOAc/cyclohexane (1:7, 2.5 l)]. The ester 8-(1,1-dimethylpropyl)-1-oxa-2-azaspiro[4.5]dec-2-ene-3-carboxylic acid ethyl ester was isolated as a colourless solid in a yield of 36% (3.0 g) having a melting point of 82-87° C.

2c. Synthesis of 8-cyclohexyl-1-oxa-2-azaspiro[4.5]dec-2-ene-3-carboxylic acid ethyl ester A solution of the olefin 4-methylenebicyclohexyl (3.9 g, 21.9 mmol) in abs. DCM (100 ml) was mixed with 2-chloro-2-hydroxyiminoacetic acid ethyl ester (16.52 g, 109 mmol) under argon and while being cooled with ice. The solution was subsequently cooled down to −5° C. Within 1 h, a solution of triethylamine (15.2 ml, 109 mmol) in abs. DCM (45 ml) was added dropwise in such a way that the internal temperature did not exceed 0° C. Subsequently, the mixture was stirred for 20 h at RT. Triethylamine hydrochloride gradually precipitated. For working up, the reaction mixture was washed with 10% aq. citric acid solution (3×100 ml) and with sat. aq. NaCl solution (70 ml). The organic phase was dried and concentrated. There was obtained a yellow oil (17.8 g) which was separated by column chromatography [silica gel 60 (200 g); cyclohexane/EtOAc/7:1 (1 l)]. The ester 8-cyclohexyl-1-oxa-2-azaspiro[4.5]dec-2-ene-3-carboxylic acid ethyl ester was isolated as a colourless solid in a yield of 39% (2.5 g) having a melting point of 64-71° C.

3.a. Synthesis of 8-tert-butyl-1-oxa-2-azaspiro[4.5]dec-2-ene-3-carboxylic acid

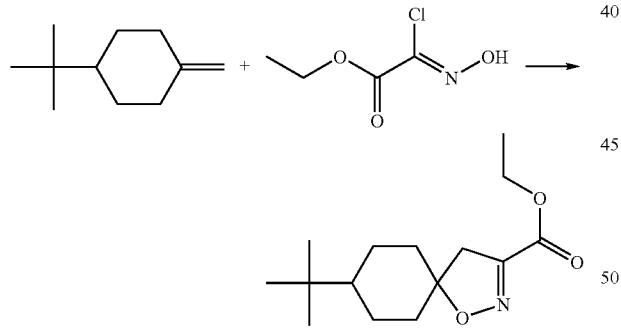

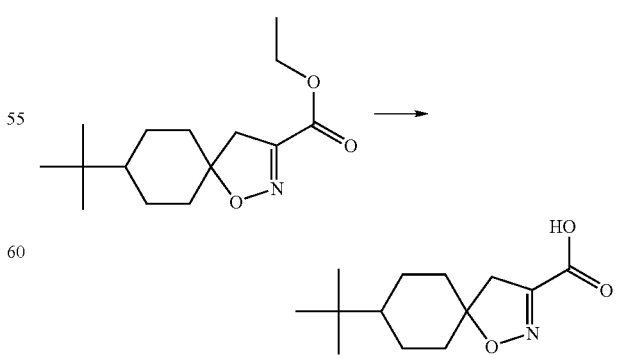

A mixture of 8-tert-butyl-1-oxa-2-azaspiro[4.5]dec-2-ene-3-carboxylic acid ethyl ester (2.4 g, 9 mmol) in MeOH (50 ml) and lithium hydroxide monohydrate (1 g, 13.5 mmol) in H$_2$O (8 ml) was stirred overnight at RT. After removal of the solvent under vacuum, the residue was taken up in 10% aq. citric acid solution and EtOAc and the phases were separated. The aqueous phase was extracted several times with EtOAc, dried over magnesium sulphate and desolventised under vacuum. 2.17 g (100% of the theoretical amount) of the free acid 8-tert-butyl-1-oxa-2-azaspiro[4.5]dec-2-ene-3-carboxylic acid was obtained in the form of a colourless solid.

3.b. Synthesis of 8-(1,1-dimethylpropyl)-1-oxa-2-azaspiro[4.5]dec-2-ene-3-carboxylic acid The ester 8-(1,1-dimethylpropyl)-1-oxa-2-azaspiro[4.5]dec-2-ene-3-carboxylic acid ethyl ester (2.8 g, 10 mmol) was dissolved in MeOH (50 ml), mixed with lithium hydroxide (357 mg, 15 mmol) in water (8 ml) and stirred for 23 h at RT. For working up the mixture, MeOH was removed under vacuum and water (25 ml) added. After the addition of 10% aq. citric acid solution (20 ml), there formed at a pH of 4 the acid 8-(1,1-dimethylpropyl)-1-oxa-2-azaspiro[4.5]dec-2-ene-3-carboxylic acid. The mixture was stirred for a further 1 h at RT, removed by suction-filtration and washed with water (3×25 ml). The acid was isolated as a colourless solid in a yield of 99% (2.55 g).

3.c. Synthesis of 8-cyclohexyl-1-oxa-2-azaspiro[4.5]dec-2-ene-3-carboxylic acid The ester 8-cyclohexyl-1-oxa-2-azaspiro[4.5]dec-2-ene-3-carboxylic acid ethyl ester (2.5 g, 8.5 mmol) was dissolved in MeOH (80 ml) while being heated, mixed with lithium hydroxide (306 mg, 13 mmol) in water (8 ml) and stirred for 60 h at RT. For working up the mixture, MeOH was removed under vacuum and water (25 ml) added. After the addition of 10% aq. citric acid solution (20 ml), there formed at a pH of 4 the acid 8-cyclohexyl-1-oxa-2-azaspiro[4.5]dec-2-ene-3-carboxylic acid. The mixture was stirred for a further 1 h at RT, removed by suction-filtration and washed with water (3×25 ml). The acid 8-cyclohexyl-1-oxa-2-azaspiro[4.5]dec-2-ene-3-carboxylic acid was isolated as a colourless solid in a yield of 82% (1.84 g) having a melting point of 139-142° C.

4. General directions for reacting 8-tert-butyl-1-oxa-2-azaspiro[4.5]dec-2-ene-3-carboxylic acid or 3',4',4a',5',6',7',8',8a'-octahydro-1'H,4H-spiro[isoxazol-5,2'-naphthalene]-3-carboxylic acid with amines of general formula HNR$^{13}$R$^{14}$ The compound 8-tert-butyl-1-oxa-2-azaspiro[4.5]dec-2-ene-3-carboxylic acid or 3',4',4a',5',6',7',8',8a'-octahydro-1'H,4H-spiro[isoxazol-5,2'-naphthalene]-3-carboxylic acid (in each case 1 eq.), the amine of general formula HNR$^{13}$R$^{14}$ (1 eq.), 4-methylmorpholine (3 eq.) and O-(benzotriazol-1-yl)-N,N,N',N'-tetramethyluronium hexafluorophosphate (3 eq.) (HBTU) were dissolved in DMF and stirred overnight under a nitrogen atmosphere at RT. The solvent was removed under vacuum, the residue taken up in EtOAc and sat. aq. NaHCO$_3$ solution and the phases were separated. The aqueous phase was extracted several times with EtOAc and the combined organic phases were dried over magnesium sulphate and the solvent was removed under vacuum. After purification by column chromatography, the desired product was obtained as a diastereomer mixture.

4a. Synthesis of Exemplary Compound 54

8-tert-butyl-1-oxa-2-azaspiro[4.5]dec-2-ene-3-carboxylic acid-(4-tert-butylphenyl)amide

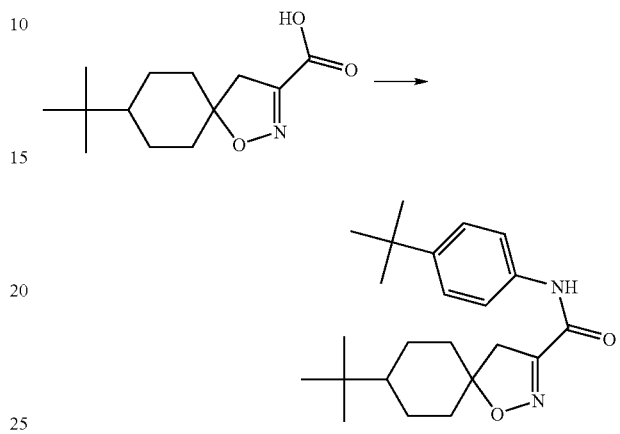

The compound 8-tert-butyl-1-oxa-2-azaspiro[4.5]dec-2-ene-3-carboxylic acid (220 mg, 0.91 mmol), 4-tert-butylaniline (137 mg, 0.91 mmol), 4-methylmorpholine (279 mg, 2.76 mmol) and O-(benzotriazol-1-yl)-N,N,N',N'-tetramethyluronium hexafluorophosphate (528 mg, 1.20 mmol) (HBTU) were dissolved in DMF (10 ml) and stirred overnight under a nitrogen atmosphere at RT. The solvent was removed under vacuum, the residue taken up in EtOAc and sat. aq. NaHCO$_3$ solution and the phases were separated. The aqueous phase was extracted several times with EtOAc and the combined organic phases were dried over magnesium sulphate and the solvent was removed under vacuum. After purification by column chromatography (silica gel, ether/hexane 2:1), the desired product 8-tert-butyl-1-oxa-2-azaspiro[4.5]dec-2-ene-3-carboxylic acid-(4-tert-butylphenyl)amide was obtained as a diastereomer mixture in a yield of 80 mg (24% of the theoretical amount).

4b. Synthesis of Exemplary Compounds 7 and 25 cis-8-tert-butyl-1-oxa-2-azaspiro[4.5]dec-2-ene-3-carboxylic acid-3-fluoro-4-methanesulphonylaminobenzylamide and trans-8-tert-butyl-1-oxa-2-azaspiro[4.5]dec-2-ene-3-carboxylic acid-3-fluoro-4-methanesulphonylaminobenzylamide

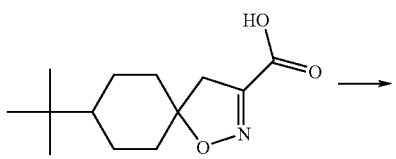

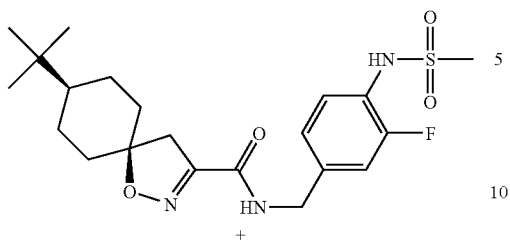

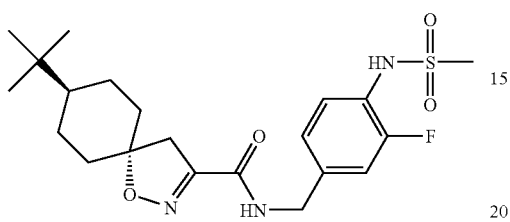

The compound 8-tert-butyl-1-oxa-2-azaspiro[4.5]dec-2-ene-3-carboxylic acid (120 mg, 0.51 mmol), N-(4-aminomethyl-2-fluorophenyl)methanesulphonamide (110 mg, 0.51 mmol), 4-methylmorpholine (101 mg, 1.02 mmol) and O-(benzotriazol-1-yl)-N,N,N',N'-tetramethyluronium hexafluorophosphate (288 mg, 0.65 mmol) (HBTU) were dissolved in DMF (10 ml) and stirred overnight under a nitrogen atmosphere at RT. The solvent was removed under vacuum, the residue taken up in EtOAc and sat. aq. NaHCO₃ solution and the phases were separated. The aqueous phase was extracted several times with EtOAc and the combined organic phases were dried over magnesium sulphate and the solvent was removed under vacuum. After purification by column chromatography (silica gel, hexane/EtOAc 2:1), the desired product 8-tert-butyl-1-oxa-2-azaspiro[4.5]dec-2-ene-3-carboxylic acid-(4-tert-butylphenyl)amide was obtained as a trans isomer (30 mg, 13% of the theoretical amount) and cis isomer (100 mg, 45% of the theoretical amount).

4c. Synthesis of Exemplary Compounds 5 and 6 trans-(8-tert-butyl-1-oxa-2-azaspiro[4.5]dec-2-en-3-yl)-(4-thiazol-2-ylpiperazin-1-yl)methanone and cis-(8-tert-butyl-1-oxa-2-azaspiro[4.5]dec-2-en-3-yl)-(4-thiazol-2-ylpiperazin-1-yl)methanone

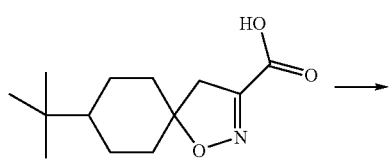

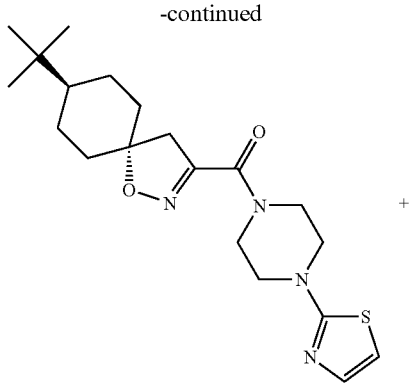

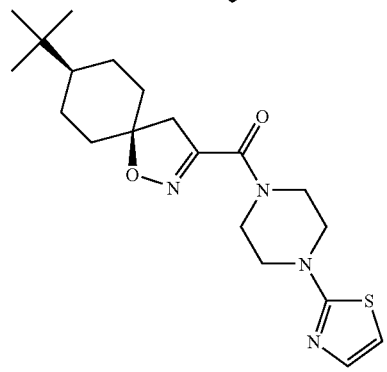

The compound 8-tert-butyl-1-oxa-2-azaspiro[4.5]dec-2-ene-3-carboxylic acid (120 mg, 0.51 mmol), 1-thiazol-2-ylpiperazine (110 mg, 0.51 mmol), 4-methylmorpholine (101 mg, 1.02 mmol) and O-(benzotriazol-1-yl)-N,N,N',N'-tetramethyluronium hexafluorophosphate (288 mg, 0.65 mmol) (HBTU) were dissolved in DMF (10 ml) and stirred overnight under a nitrogen atmosphere at RT. The solvent was removed under vacuum, the residue taken up in EtOAc and sat. aq. NaHCO₃ solution and the phases were separated. The aqueous phase was extracted several times with EtOAc and the combined organic phases were washed with sat. aq. NaCl solution, dried over magnesium sulphate and the solvent was removed under vacuum. After purification by column chromatography (silica gel, hexane/EtOAc 3:1), the desired product (8-tert-butyl-1-oxa-2-azaspiro[4.5]dec-2-en-3-yl)-(4-thiazol-2-ylpiperazin-1-yl)methanone was obtained as a trans isomer (50 mg, 26% of the theoretical amount) and as a cis isomer (100 mg, 51% of the theoretical amount).

4d. Synthesis of Exemplary Compounds 28 and 29 trans-(8-tert-butyl-1-oxa-2-za-spiro[4.5]dec-2-en-3-yl)-[4-(3-chloropyridin-2-yl)piperazin-1-yl]methanone and cis-(8-tert-butyl-1-oxa-2-azaspiro[4.5]dec-2-en-3-yl)-[4-(3-chloropyridin-2-yl)piperazin-1-yl]methanone

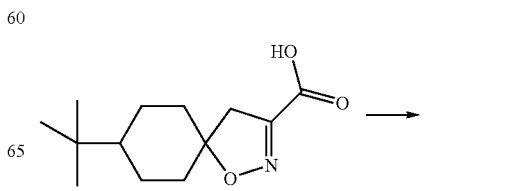

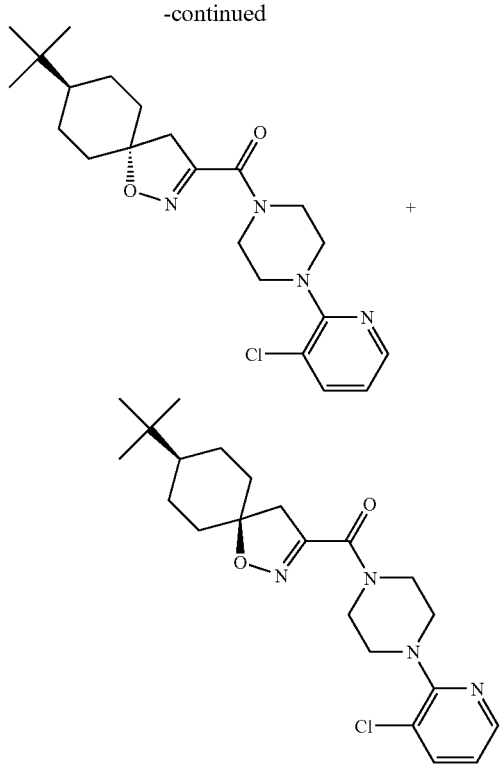

The compound 8-tert-butyl-1-oxa-2-azaspiro[4.5]dec-2-ene-3-carboxylic acid (150 mg, 0.63 mmol), 1-(3-chloropyridin-2-yl)piperazine (361 mg, 0.82 mmol), 4-methylmorpholine (190 mg, 1.88 mmol) and O-(benzotriazol-1-yl)-N,N,N',N'-tetramethyluronium hexafluorophosphate (361 mg, 0.81 mmol) (HBTU) were dissolved in DMF (10 ml) and stirred overnight under a nitrogen atmosphere at RT. The solvent was removed under vacuum, the residue taken up in EtOAc and sat. aq. NaHCO₃ solution and the phases were separated. The aqueous phase was extracted several times with EtOAc and the combined organic phases were washed with sat. aq. NaCl solution, dried over magnesium sulphate and the solvent was removed under vacuum. After purification by column chromatography (silica gel, ether/hexane 2:1), the desired product (8-tert-butyl-1-oxa-2-za-spiro[4.5]dec-2-en-3-yl)-[4-(3-chloropyridin-2-yl)piperazin-1-yl]methanone was obtained as a cis isomer (100 mg, 38% of the theoretical amount) and as a trans isomer (90 mg, 34% of the theoretical amount).

4e. Synthesis of Exemplary Compound 90

8-tert-butyl-1-oxa-2-azaspiro[4.5]dec-2-ene-3-carboxylic acid-(3-fluoro-4-methanesulphonylaminophenyl)amide The acid 8-tert-butyl-1-oxa-2-azaspiro[4.5]dec-2-ene-3-carboxylic acid (359 mg, 1.5 mmol) was dissolved in THF (15 ml). N,N'-carbonyldiimidazole (243.5 mg, 1.5 mmol) was added while stirring. For activation, the mixture was stirred for 1 h at RT. The N-(4-amino-2-fluorophenyl)methanesulphonamide (326.8 mg, 1.60 mmol) was then added as a solid. The course of the reaction was controlled by DC. After 3 d only small amounts of starting products could still be seen in the DC. For working up, THF was removed by distillation. The residue was dissolved in 0.5 N aq. HCl (10 ml) and EtOAc (40 ml). The phases were separated. The organic phase was washed successively with 0.5 N aq. HCl (2×8 ml), with water (1×10 ml), with 1.1 M aq. NaHCO₃ solution (3×7 ml) and water (3×10 ml). The organic phase was dried with Na₂SO₄. The solvent was removed by distillation. The light brown residue was stirred out with diethyl ether (3×2 ml). The solvent was in each case removed by suction-filtration. The light pink residue was the mixture of the diastereoisomers of 8-tert-butyl-1-oxa-2-azaspiro[4.5]dec-2-ene-3-carboxylic acid-(3-fluoro-4-methanesulphonylaminophenyl)amide (353 mg, mp 104-107° C. and 228-232° C., 55%).

4f. Synthesis of Exemplary Compound 91

8-tert-butyl-1-oxa-2-azaspiro[4.5]dec-2-ene-3-carboxylic acid-[3-fluoro-4-(bismethanesulphonyl)aminophenyl]amide The acid 8-tert-butyl-1-oxa-2-azaspiro[4.5]dec-2-ene-3-carboxylic acid (292.8 mg, 1.22 mmol) was dissolved in THF (12 ml). N,N'-carbonyldiimidazole (198 mg, 1.22 mmol) was added while stirring. For activation, the mixture was stirred for 1 h at RT. The amine N-(4-amino-2-fluorophenyl)bismethanesulphonamide (380 mg, 1.34 mmol) was then added as a solid. The course of the reaction was controlled by DC. After 4 d, a plurality of new products could be seen in the DC in addition to the starting products. For working up, THF was removed by distillation. The residue was dissolved in 0.5 N aq. HCl (7 ml) and EtOAc (30 ml). The phases were separated. The organic phase was washed successively with 0.5 N aq. HCl (2×7 ml), with water (1×10 ml), with 1.1 M aq. NaHCO₃ solution (3×5 ml) and water (1×5 ml). The organic phase was dried with Na₂SO₄. The solvent was removed by distillation. The beige residue (502 mg) was very difficult to dissolve in cyclohexane/EtOAc (2:1). The insoluble content was removed by suction-filtration. The clear filtrate was highly concentrated. The product mixture was purified by flash chromatography [silica gel 60 (30 g); eluent: cyclohexane/EtOAc (4:1; 500 ml), cyclohexane/EtOAc (3:1; 400 ml) and cyclohexane/EtOAc (1:1; 300 ml)]. The mixture of the diastereoisomers 8-tert-butyl-1-oxa-2-azaspiro[4.5]dec-2-ene-3-carboxylic acid-[3-fluoro-4-(bismethanesulphonyl)aminophenyl]amide (89 mg, mp 98-104° C. and 124-126° C., 14%) was thus isolated as a beige solid.

4g. Synthesis of Exemplary Compound 89

8-tert-butyl-1-oxa-2-azaspiro[4.5]dec-2-ene-3-carboxylic acid-(4-fluoro-3-methanesulphonylaminophenyl)amide The acid 8-tert-butyl-1-oxa-2-azaspiro[4.5]dec-2-ene-3-carboxylic acid (359 mg, 1.5 mmol) was dissolved in THF (15 ml). N,N'-carbonyldiimidazole (243.5 mg, 1.5 mmol) was added while stirring. For activation, the mixture was stirred for 1 h at RT. The amine N-(5-amino-2-fluorophenyl)methanesulphonamide (337 mg, 1.65 mmol) was then added as a solid. The course of the reaction was controlled by DC. After 3 d only small amounts of starting products could still be seen in the DC. For working up, THF was removed by distillation. The viscous residue was dissolved in 0.5 N aq. HCl (10 ml) and EtOAc (10 ml). The phases were separated. The organic phase was washed successively with 0.5 N aq. HCl (2×5 ml), with 1.1 M aq. NaHCO₃ (3×5 ml) and water (2×5 ml). The organic phase was dried with Na₂SO₄. The solvent was removed by distillation. The beige residue was the mixture of the diastereoisomers of 8-tert-butyl-1-oxa-2-azaspiro[4.5]

dec-2-ene-3-carboxylic acid-(4-fluoro-3-methanesulphonylaminophenyl)amide (381.5 mg, mp 180-183° C. and 200-204° C., 73%).

4h. Synthesis of Exemplary Compound 87

8-tert-butyl-1-oxa-2-azaspiro[4.5]dec-2-ene-3-carboxylic acid-(2-fluoro-5-methanesulphonylaminophenyl)amide The acid 8-tert-butyl-1-oxa-2-azaspiro[4.5]dec-2-ene-3-carboxylic acid (240 mg, 1 mmol) dissolved was in THF (5 ml). N,N'-carbonyldiimidazole (163 mg, 1 mmol) was added while stirring. For activation, the mixture was stirred for 1 h at RT. The amine N-(3-amino-4-fluorophenyl)methanesulphonamide (306 mg, 1.5 mmol), dissolved in THF (5 ml), was then added dropwise. The course of the reaction was controlled by DC. Even after 5 d, starting products could still be seen in the DC. The reaction mixture was dark brown in colour and contained little precipitate. For working up, THF was removed by distillation. The residue was dissolved in 0.5 N aq. HCl (7 ml), water (5 ml) and EtOAc (35 ml). The phases were separated. The organic phase was washed successively with 0.5 N aq. HCl (2×7 ml), with 1.1 M aq. NaHCO$_3$ solution (3×10 ml) and water (2×5 ml). The organic phase was dried with Na$_2$SO$_4$. The solvent was removed by distillation. The residue was purified by flash chromatography [silica gel 60 (30 g); eluent: cyclohexane/EtOAc (3:1; 300 ml), cyclohexane/EtOAc (1:1; 700 ml)]. The mixture of the diastereoisomers of 8-tert-butyl-1-oxa-2-azaspiro[4.5]dec-2-ene-3-carboxylic acid-(2-fluoro-5-methanesulphonylaminophenyl) amide (46 mg, mp 155-165° C., 11%) was a beige solid.

4i. Synthesis of Exemplary Compound 88

8-tert-butyl-1-oxa-2-azaspiro[4.5]dec-2-ene-3-carboxylic acid-[2-fluoro-5-(bis-methanesulphonyl) aminophenyl]amide The acid 8-tert-butyl-1-oxa-2-azaspiro[4.5]dec-2-ene-3-carboxylic acid (240 mg, 1 mmol) was dissolved in THF (10 ml). N,N'-carbonyldiimidazole (163 mg, 1 mmol) was added while stirring. For activation, the mixture was stirred for 1 h at RT. The amine N-(3-aminofluorophenyl)bismethanesulphonamide (310 mg, 1.1 mmol) was then added as a solid. The course of the reaction was controlled by DC. After 24 h, a product spot was still clearly visible in the DC. The reaction mixture was a suspension. For working up, THF was removed by distillation. The residue was mixed with 0.5 N aq. HCl (7 ml), water (15 ml) and EtOAc (40 ml). The organic phase contained a solid. The solid was removed by suction-filtration, washed, dried and analysed (74 mg, light yellow, no product). The phases were separated. The organic phase was washed with 1.1 M aq. NaHCO$_3$ solution (1×15 ml) and water (2×20 ml). The organic phase was dried with Na$_2$SO$_4$. The solvent was removed by distillation. The residue was purified by flash chromatography [silica gel 60 (30 g); eluent: cyclohexane/EtOAc (4:1; 200 ml), cyclohexane/EtOAc (3:1; 300 ml)]. The mixture of the diastereoisomers 8-tert-butyl-1-oxa-2-azaspiro[4.5]dec-2-ene-3-carboxylic acid-[2-fluoro-5-(bismethanesulphonyl)aminophenyl]amide (54 mg, mp 94-97° C., 11%) was a light beige solid.

4j. Synthesis of Exemplary Compound 4

8-tert-butyl-1-oxa-2-azaspiro[4.5]dec-2-ene-3-carboxylic acid isoquinolin-5-ylamide Pyridine (5 drops) and oxalyl chloride (0.151 ml, 1.75 mmol) were added to a solution of the acid 8-tert-butyl-1-oxa-2-azaspiro[4.5]dec-2-ene-3-carboxylic acid (300 mg, 1.25 mmol) in dry toluene (40 ml). The mixture was stirred for 45 min at RT. Subsequently, the reaction mixture was stirred for 30 min at 30-40° C. and then for 1 h at RT. The solvent and excess oxalyl chloride were removed under vacuum. The acid chloride formed was used for further reaction immediately and without purification.

5-Aminoisoquinoline (0.36 g, 2.5 mmol) was placed in abs. toluene (20 ml). Subsequently, the acid chloride, dissolved in abs. toluene (20 ml), was slowly added dropwise to this solution. The mixture was stirred for 1 h at RT. For working up the mixture, the toluene was removed under vacuum and the residue mixed with DCM (70 ml). The organic solution was washed with water (2×50 ml), 2 N aq. HCl (30 ml), sat. aq. NaHCO$_3$ solution (50 ml) and sat. aq. NaCl solution (50 ml), dried over NaSO$_4$ and concentrated. The crude product thus obtained (oil, 680 mg) was purified by means of column chromatography [silica gel 60 (50 g); EtOAc/EtOH (15:1; 500 ml)]. The amide 8-tert-butyl-1-oxa-2-azaspiro[4.5]dec-2-ene-3-carboxylic acid isoquinolin-5-ylamide was isolated as a light yellow solid having a melting point of 99-119° C. as a diastereoisomer mixture in a yield of 57% (266 mg).

4k. Synthesis of Exemplary Compound 83

8-tert-butyl-1-oxa-2-azaspiro[4.5]dec-2-ene-3-carboxylic acid-(7-hydroxynaphthalen-1-yl)amide Oxalyl chloride (0.13 ml, 1.5 mmol) was added to a solution of the acid 8-tert-butyl-1-oxa-2-azaspiro[4.5]dec-2-ene-3-carboxylic acid (239 mg, 1 mmol) in dry toluene (20 ml) at RT. The mixture was stirred for 18 h at RT. To remove the excess oxalyl chloride, the solvent was concentrated under vacuum to approx. 10 ml. The solution formed of the acid chloride was used for further reaction immediately and without purification. 8-Amino-2-naphthol (159 mg, 1 mmol) was placed in abs. methylene chloride (40 ml), mixed with triethylamine (0.4 ml, 2.9 mmol) and stirred for 10 min at RT. Subsequently, the solution of the acid chloride was added dropwise within 10 min. Although hardly any amines were left after stirring for 1 h (DC, cyclohexane/EtOAc 1:1), the mixture was stirred for a further 20 h at RT. For working up, the mixture was mixed with 1 N aq. HCl (20 ml). The organic phase was separated off, the aqueous phase was extracted with DCM (2×20 ml). The combined organic phases were washed with water (2×10 ml), dried over Na$_2$SO$_4$ and subsequently concentrated. The residue obtained was purified by column chromatography [mobile solvent: cyclohexane/EtOAc (7:3)]. The residue obtained was recrystallised from cyclohexane (30 ml). There was obtained a reddish solid (60 mg, 15% yield, mp: 168-191° C.) which consisted of the diastereomers of 8-tert-butyl-1-oxa-2-azaspiro[4.5]dec-2-ene-3-carboxylic acid-(7-hydroxynaphthalen-1-yl)amide.

4l. Synthesis of Exemplary Compound 79

8-tert-butyl-1-oxa-2-azaspiro[4.5]dec-2-ene-3-carboxylic acid-(2,3-dihydrobenzo[1,4]dioxin-5-yl) amide Pyridine (2 drops) and oxalyl chloride (0.151 ml, 1.75 mmol) were added to a solution of the acid 8-tert-butyl-1-oxa-2-azaspiro[4.5]dec-2-ene-3-carboxylic acid (300 mg, 1.25 mmol) in dry toluene (40 ml). The mixture was stirred for 45 min at RT. Subsequently, the reaction mixture was stirred for 30 min at 30-40° C. and then 1 h at RT. The solvent and excess oxalyl chloride were drawn off under vacuum. The acid chloride formed was used for further reaction immediately and without purification. 5-Amino-1,4-benzodioxane (0.37 g, 2.5 mmol) was placed in abs. toluene (20 ml). Subsequently, the acid chloride, dissolved in abs. toluene (20 ml), was added dropwise to this solution within 20 min. The mixture was stirred for 1 h at RT. For working up the mixture, the toluene was removed under vacuum and the residue taken up in DCM (70 ml). Subsequently, the organic phase was washed with water (2×50 ml), 2 N aq. HCl (30 ml), sat. aq. NaHCO$_3$ solution (50 ml) and sat. aq. NaCl solution (50 ml), dried over Na$_2$SO$_4$ and concentrated. The amide 8-tert-butyl-1-oxa-2-azaspiro[4.5]dec-2-ene-3-carboxylic acid-(2,3-dihydrobenzo[1,4]dioxin-5-yl)amide was thus isolated as a light yellow solid having a melting point of 120-126° C. as a diastereoisomer mixture in a yield of 98% (500 mg).

4m. Synthesis of Exemplary Compound 86

8-tert-butyl-1-oxa-2-azaspiro[4.5]dec-2-ene-3-carboxylic acid-(5-hydroxynaphthalen-1-yl)amide N,N'-carbonyldiimidazole (765 mg, 4.72 mmol) was added to a solution of the acid 8-tert-butyl-1-oxa-2-azaspiro[4.5]dec-2-ene-3-carboxylic acid (1.03 g, 4.29 mmol) in abs. THF (50 ml). The mixture was stirred for 3 h at RT. After the addition of the amine 5-aminonaphthalen-1-ol (683 mg, 4.29 mmol) in abs. THF (20 ml), the solution was stirred for 3 days at RT. For working up, THF was removed by distillation. The brown oily residue was mixed with water (20 ml) and EtOAc (40 ml) and brought to pH 3 using 1 N aq. HCl. The phases were separated. The organic phase was washed with sat. aq. NaHCO$_3$ solution (2×20 ml) and sat. aq. NaCl solution (2×20 ml). After drying, the solvent was removed by distillation. Recrystallisation of the residue [cyclohexane (10 ml)] yielded a solid (melting point from 188° C., yield 245 mg, 15%) which is the diastereoisomer mixture of 8-tert-butyl-1-oxa-2-azaspiro[4.5]dec-2-ene-3-carboxylic acid-(5-hydroxynaphthalen-1-yl)amide.

4n. Synthesis of Exemplary Compound 80

N-(3-fluoro-4-(methylsulphonamido)benzyl)-8-tert-pentyl-1-oxa-2-azaspiro[4.5]dec-2-ene-3-carboxamide A solution of the acid 8-(1,1-dimethylpropyl)-1-oxa-2-azaspiro[4.5]dec-2-ene-3-carboxylic acid (253 mg, 1 mmol) in dry THF (15 ml) was mixed with CDI (178 mg, 1.1 mmol) and stirred for 1.5 h at RT. A solution consisting of the amine N-(4-aminomethyl-2-fluorophenyl)methanesulphonamide (240 mg, 1.1 mmol) and THF (10 ml) was then added. The mixture was stirred for 20 h at RT. The colourless clear solution was concentrated. The oily residue was stirred with EtOAc (40 ml) and 10% aq. citric acid solution (20 ml) for 10 min. The phases were then separated and the organic phase was washed with sat. aq. NaHCO$_3$ solution (2×15 ml) and with sat. aq. NaCl solution (1×15 ml). The organic phase was dried and concentrated. The residue was purified by column chromatography [silica gel 60 (70 g); cyclohexane/EtOAc (5:1; 500 ml); EtOAc (500 ml)]. The compound N-(3-fluoro-4-(methylsulphonamido)benzyl)-8-tert-pentyl-1-oxa-2-azaspiro[4.5]dec-2-ene-3-carboxamide was obtained as a colourless oil in a yield of 25% (112 mg).

4.o. Synthesis of Exemplary Compound 82

8-cyclohexyl-1-oxa-2-azaspiro[4.5]dec-2-ene-3-carboxylic acid-3-fluoro-4-methanesulphonylaminobenzylamide A solution of the acid 8-cyclohexyl-1-oxa-2-azaspiro[4.5]dec-2-ene-3-carboxylic acid (531 mg, 2 mmol) in dry THF (30 ml) was mixed with CDI (357 mg, 2.2 mmol) and stirred for 1.5 h at RT. A solution consisting of the amine N-(4-aminomethyl-2-fluorophenyl)methanesulphonamide (480 mg, 2.2 mmol) and THF (10 ml) was then added. The mixture was stirred for 20 h at RT. The colourless clear solution was concentrated. The oily residue was stirred with EtOAc (50 ml) and 10% aq. citric acid solution (25 ml) for 10 min. The phases were then separated and the organic phase was washed with sat. aq. NaHCO$_3$ solution (2×20 ml) and with sat. aq. NaCl solution (1×20 ml). The organic phase was dried and concentrated to approx. 5 ml, wherein a colourless solid formed. The mixture was stored for 18 h in a refrigerator and the solid removed by suction-filtration. The compound 8-cyclohexyl-1-oxa-2-azaspiro[4.5]dec-2-ene-3-carboxylic acid-3-fluoro-4-methanesulphonylaminobenzylamide was obtained as a colourless solid (99 mg, 7%) having a melting point of 225-228° C.

4.p. Synthesis of Exemplary Compound 81

8-(1,1-dimethylpropyl)-1-oxa-2-azaspiro[4.5]dec-2-ene-3-carboxylic acid-(2,3-dihydrobenzo[1,4]dioxin-5-yl)amide Oxalyl chloride (0.13 ml, 1.5 mmol) was added to a solution of the acid 8-(1,1-dimethylpropyl)-1-oxa-2-azaspiro[4.5]dec-2-ene-3-carboxylic acid (253 mg, 1 mmol) in dry toluene (20 ml) at RT. The mixture was stirred for 18 h at RT. To remove the excess oxalyl chloride, the solvent was concentrated under vacuum to approx. 10 ml. The solution formed of the acid chloride was used for further reaction immediately and without purification. 2,3-Dihydrobenzo[1,4]dioxin-5-ylamine (151 mg, 1 mmol) was placed in abs. toluene (20 ml) and mixed with triethylamine (0.2 ml, 1.45 mmol). Subsequently, the solution of the acid chloride was added dropwise within 20 min at RT. Although hardly any amines were left after stirring for 1 h [DC, cyclohexane/EtOAc 3:1)], the mixture was stirred for a further 14 h at RT. For working up the mixture, the mixture was mixed with 1 N aq. NaOH solution (10 ml) and shaken out. The organic phase was separated off, the aqueous phase was washed with EtOAc (3×20 ml). The combined organic phases were washed with 1 N aq. HCl (10 ml), dried over Na$_2$SO$_4$ and concentrated under vacuum. The residue obtained was purified by chromatography [mobile solvent: cyclohexane/EtOAc (9:1)]. The desired amide 8-(1,1-dimethylpropyl)-1-oxa-2-azaspiro[4.5]dec-2-ene-3-carboxylic acid-(2,3-dihydrobenzo[1,4]dioxin-5-yl)amide was thus obtained in a yield of 223 mg (58%, glass-like solid, mp from 45° C.) as an isomer mixture.

The exemplary compounds 58 ((5R,8R)-8-tert-butyl-1-oxa-2-azaspiro[4.5]dec-2-en-3-yl)(4-(3-chloropyridin-2-yl)-2,6-dimethylpiperazin-1-yl)methanone and 59 ((5S,8S)-8-tert-butyl-1-oxa-2-azaspiro[4.5]dec-2-en-3-yl)(4-(3-chloropyridin-2-yl)-2,6-dimethylpiperazin-1-yl)methanone were synthesised as described hereinbefore and have the following structures:

Beispielverbindung 58

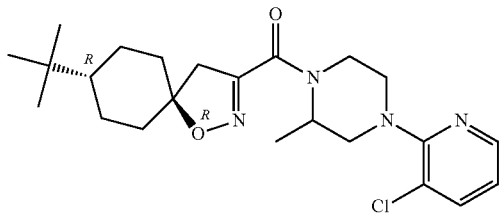

Beispielverbindung 59

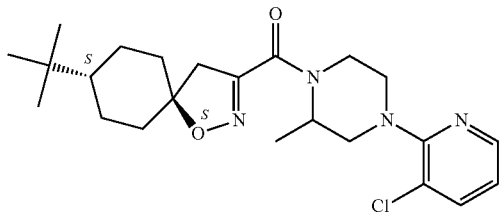

Beispielverbindung = Exemplary compound

The following substituted spiro compounds according to the invention were prepared as described under 4.

5. Synthesis of 4-methylenecyclohexanecarboxylic acid ethyl ester

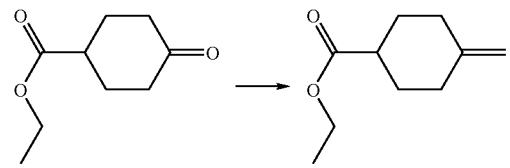

Methyltriphenylphosphonium bromide (34.1 g, 95.5 mmol) was placed in abs. diethyl ether (420 ml) under a nitrogen atmosphere. At 0° C., potassium tert-butylate (13.1 g, 113.1 mmol) was slowly added. After 30 min, again at 0° C., ethyl-4-oxocyclohexanecarboxylate (10.7 g, 62.9 mmol) was slowly added dropwise as a solution in diethyl ether (80 ml). The reaction mixture was stirred overnight at RT. For working up, the reaction mixture was cooled in an ice bath and mixed with sat. aq. NH$_4$Cl solution (250 ml). The phases were separated and the aqueous phase was shaken out several times with EtOAc (3×200 ml). The combined organic phases were dried over magnesium sulphate and the solvent was removed under vacuum. The precipitate thus formed was removed by suction-filtration and dried overnight using a pump. The mother liquor was placed onto a glass frit filled with silica gel and flushed with ether/hexane (400 ml). The

| | Name | [M + H] |
|---|---|---|
| 1 | 8-tert-butyl-1-oxa-2-azaspiro[4.5]dec-2-ene-3-carboxylic acid-4-aminobenzylamide | 344.5 |
| 2 | trans-8-tert-butyl-1-oxa-2-azaspiro[4.5]dec-2-ene-3-carboxylic acid-4-methanesulphonylaminobenzylamide | 422.6 |
| 3 | cis-8-tert-butyl-1-oxa-2-azaspiro[4.5]dec-2-ene-3-carboxylic acid-4-methanesulphonylaminobenzylamide | 422.6 |
| 5 | trans-(8-tert-butyl-1-oxa-2-azaspiro[4.5]dec-2-en-3-yl)-(4-thiazol-2-ylpiperazin-1-yl)methanone | 391.5 |
| 6 | cis-(8-tert-butyl-1-oxa-2-azaspiro[4.5]dec-2-en-3-yl)-(4-thiazol-2-ylpiperazin-1-yl)methanone | 391.5 |
| 7 | cis-8-tert-butyl-1-oxa-2-azaspiro[4.5]dec-2-ene-3-carboxylic acid-3-fluoro-4-methanesulphonylaminobenzylamide | 440.5 |
| 8 | trans-(8-tert-butyl-1-oxa-2-azaspiro[4.5]dec-2-en-3-yl)-[4-(3-trifluoromethylpyridin-2-yl)piperazin-1-yl]methanone | 453.5 |
| 9 | cis-(8-tert-butyl-1-oxa-2-azaspiro[4.5]dec-2-en-3-yl)-[4-(3-trifluoromethylpyridin-2-yl)piperazin-1-yl]methanone | 453.5 |
| 10 | trans-(8-tert-butyl-1-oxa-2-azaspiro[4.5]dec-2-en-3-yl)-[4-(4-hydroxyphenyl)piperazin-1-yl]methanone | 400.5 |
| 11 | cis-(8-tert-butyl-1-oxa-2-azaspiro[4.5]dec-2-en-3-yl)-[4-(4-hydroxyphenyl)piperazin-1-yl]methanone | 400.5 |
| 12 | (8-tert-butyl-1-oxa-2-azaspiro[4.5]dec-2-en-3-yl)-(6,7-dihydroxy-3,4-dihydro-1H-isoquinolin-2-yl)methanone | 387.5 |
| 13 | cis-(8-tert-butyl-1-oxa-2-azaspiro[4.5]dec-2-en-3-yl)-[4-(6-methylpyridazin-3-yl)piperazin-1-yl]methanone | 400.5 |
| 14 | trans-(8-tert-butyl-1-oxa-2-azaspiro[4.5]dec-2-en-3-yl)-[4-(6-methylpyridazin-3-yl)piperazin-1-yl]methanone | 400.5 |
| 15 | cis-(8-tert-butyl-1-oxa-2-azaspiro[4.5]dec-2-en-3-yl)-(4-pyrimidin-2-ylpiperazin-1-yl)methanone | 386.5 |
| 16 | trans-(8-tert-butyl-1-oxa-2-azaspiro[4.5]dec-2-en-3-yl)-(4-pyrimidin-2-ylpiperazin-1-yl)methanone | 386.5 |
| 17 | cis-(8-tert-butyl-1-oxa-2-azaspiro[4.5]dec-2-en-3-yl)-[4-(4-chloro-[1,2,5]thiadiazol-3-yl)piperazin-1-yl]methanone | 427.0 |
| 18 | trans-(8-tert-butyl-1-oxa-2-azaspiro[4.5]dec-2-en-3-yl)-(6,7-dimethoxy-3,4-dihydro-1H-isoquinolin-2-yl)methanone | 415.5 |
| 19 | cis-(8-tert-butyl-1-oxa-2-azaspiro[4.5]dec-2-en-3-yl)-(6,7-dimethoxy-3,4-dihydro-1H-isoquinolin-2-yl)methanone | 415.5 |
| 20 | trans-(8-tert-butyl-1-oxa-2-azaspiro[4.5]dec-2-en-3-yl)-[4-(4-chloro-[1,2,5]thiadiazol-3-yl)piperazin-1-yl]methanone | 427.0 |
| 21 | trans-(8-tert-butyl-1-oxa-2-azaspiro[4.5]dec-2-en-3-yl)-[4-(3-chloropyridin-2-yl)-[1,4]diazepan-1-yl]methanone | 434.0 |
| 22 | cis-(8-tert-butyl-1-oxa-2-azaspiro[4.5]dec-2-en-3-yl)-[4-(3-chloropyridin-2-yl)-[1,4]diazepan-1-yl]methanone | 434.0 |
| 23 | trans-8-tert-butyl-1-oxa-2-azaspiro[4.5]dec-2-ene-3-carboxylic acid (pyridin-4-ylmethyl)amide | 330.4 |
| 24 | cis-8-tert-butyl-1-oxa-2-azaspiro[4.5]dec-2-ene-3-carboxylic acid (pyridin-4-ylmethyl)amide | 330.4 |
| 25 | trans-8-tert-butyl-1-oxa-2-azaspiro[4.5]dec-2-ene-3-carboxylic acid-3-fluoro-4-methanesulphonylaminobenzylamide | 440.5 |
| 26 | trans-8-tert-butyl-1-oxa-2-azaspiro[4.5]dec-2-ene-3-carboxylic acid-4-hydroxy-3-methoxybenzylamide | 375.5 |
| 27 | cis-8-tert-butyl-1-oxa-2-azaspiro[4.5]dec-2-ene-3-carboxylic acid-4-hydroxy-3-methoxybenzylamide | 375.5 |
| 28 | trans-(8-tert-butyl-1-oxa-2-azaspiro[4.5]dec-2-en-3-yl)-[4-(3-chloropyridin-2-yl)piperazin-1-yl]methanone | 420.0 |
| 29 | cis-(8-tert-butyl-1-oxa-2-azaspiro[4.5]dec-2-en-3-yl)-[4-(3-chloropyridin-2-yl)piperazin-1-yl]methanone | 420.0 |
| 30 | 3',4',4a',5',6',7',8',8a'-octahydro-1'H,4H-spiro[isoxazol-5,2'-naphthalene]-3-carboxylic acid-(4-tert-butylphenyl)amide | 369.5 |
| 31 | 3',4',4a',5',6',7',8',8a'-octahydro-1'H,4H-spiro[isoxazol-5,2'-naphthalene]-3-carboxylic acid-(4-tert-butylbenzyl)amide | 383.5 |
| 32 | 3',4',4a',5',6',7',8',8a'-octahydro-1'H,4H-spiro[isoxazol-5,2'-naphthalene]-3-carboxylic acid-3-fluoro-4-methanesulphonylaminobenzylamide | 438.5 |
| 92 | 8-tert-butyl-1-oxa-2-azaspiro[4.5]dec-2-ene-3-carboxylic acid-4-pentafluorosulphanylbenzylamide | |
| 55 | 3-phenyl-1-oxa-2-azaspiro[4.5]dec-2-ene-8-carboxylic acid-trans-(4-tert-butylphenyl)amide | |
| 56 | 8-tert-butyl-N-(4-(methylsulphonamido)benzyl)-1-oxa-2-azaspiro[4.5]dec-2-ene-3-carboxamide | |
| 60 | ((5R,8R)-8-tert-butyl-1-oxa-2-azaspiro[4.5]dec-2-en-3-yl)(4-(3-chloropyridin-2-yl)-2-methylpiperazin-1-yl)methanone | |
| 61 | ((5S,8S)-8-tert-butyl-1-oxa-2-azaspiro[4.5]dec-2-en-3-yl)(4-(3-chloropyridin-2-yl)-2-methylpiperazin-1-yl)methanone | |
| 84 | N-(4-tert-butylphenyl)-3-(4-(3-chloropyridin-2-yl)piperazin-1-carbonyl)-1-oxa-2-azaspiro[4.5]dec-2-ene-8-carboxamide | |
| 85 | N-(4-tert-butylbenzyl)-3-(4-(3-chloropyridin-2-yl)piperazin-1-carbonyl)-1-oxa-2-azaspiro[4.5]dec-2-ene-8-carboxamide | | filtrate was concentrated and the residue not dried any further. 7.1 g (66% of the theoretical amount) of the desired product 4-methylenecyclohexane carboxylic acid ethyl ester were obtained.

6.a. Synthesis of 1-chloro-1-hydroxyiminomethylbenzene

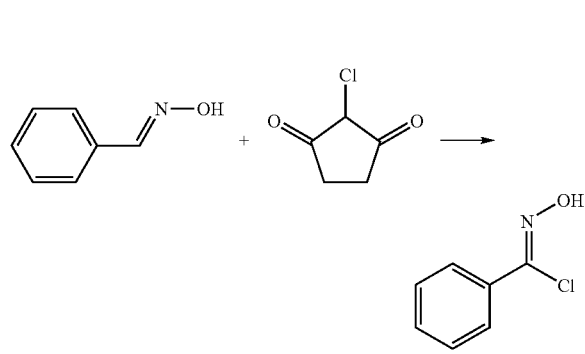

N-chlorosuccinimide (4.63 g, 34.7 mmol) was added to a solution of benzaldehyde oxime (3.5 g, 28.9 mmol) in DMF (30 ml) at RT, causing the temperature to rise briefly to 50° C. The reaction mixture was cooled in an ice bath, stirred for 3 h at RT, mixed with water (100 ml) while being pooled with ice and extracted with ether (3×100 ml). The combined organic phases were washed with water (150 ml) and sat. aq. NaCl solution (150 ml), dried and the solvent was removed under vacuum. The desired product 1-chloro-1-hydroxyiminomethylbenzene was obtained as a yellowish solid (4.28 g).

6.b. Synthesis of 1-chloro-1-hydroxyiminomethyl-3-methoxybenzene

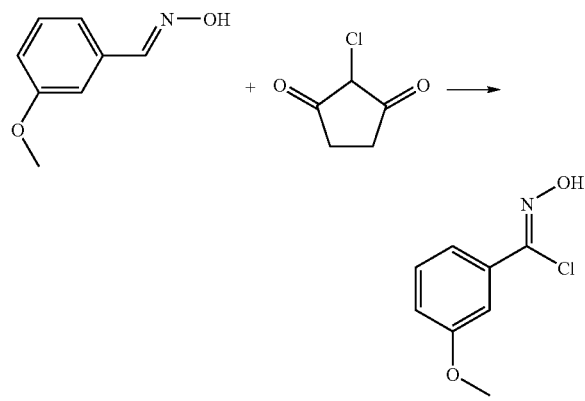

N-chlorosuccinimide (32.2 g, 241 mmol) was added to a solution of 3-methoxybenzaldehyde oxime (30.4 g, 201 mmol) in DMF (200 ml) at RT, causing the temperature to rise briefly to 50° C. The reaction mixture was cooled in an ice bath, stirred overnight at RT, mixed with water (250 ml) while being cooled with ice and the precipitate formed was removed by suction-filtration. The filtrate was extracted with ether (3×400 ml) and the combined organic phases were washed with water (300 ml) and sat. aq. NaCl solution (300 ml), dried and the solvent was removed under vacuum. The desired product 1-chloro-1-hydroxyiminomethyl-3-methoxybenzene was obtained as a yellowish solid (32.86 g).

6.c. Synthesis of 1-chloro-1-hydroxyiminoethane

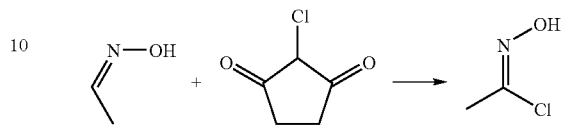

N-chlorosuccinimide (20.3 g, 152 mmol) was added to a solution of acetaldehyde oxime (8 g, 127 mmol) in DMF (100 ml) at RT, causing the temperature to rise briefly to 50° C. The reaction mixture was cooled in an ice bath, stirred overnight at RT and mixed with water (250 ml) while being cooled with ice. The mixture was extracted with ether (200 ml) and the combined organic phases were washed with water (100 ml) and sat. aq. NaCl solution (100 ml), dried and the solvent was removed under vacuum. The desired product 1-chloro-1-hydroxyiminoethane was obtained as a colourless oil (10.84 g).

7.a. Synthesis of 3-phenyl-1-oxa-2-azaspiro[4.5]dec-2-ene-8-carboxylic acid ethyl ester

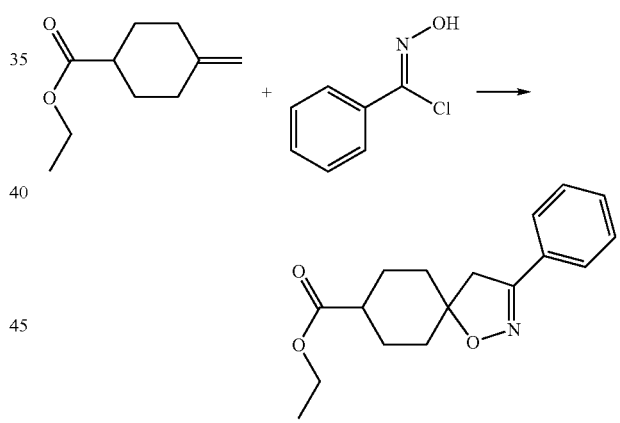

A solution of 1-chloro-1-hydroxyiminomethylbenzene (1.26 g, 8.1 mmol) in DCM (20 ml) was slowly added dropwise to a solution of 4-methylenecyclohexanecarboxylic acid ethyl ester (454 mg, 2.70 mmol) in DCM (15 ml) at 0° C. Subsequently, a solution of triethylamine (656 µl) in DCM (15 ml) was slowly added dropwise at 0° C. and the resulting mixture was stirred overnight at RT.

The reaction mixture was diluted with DCM and with water. The combined organic phases were washed with 10%. aq. citric acid solution and sat. aq. NaCl solution, dried over sodium sulphate and the solvent was removed under vacuum. After purification of the residue (silica gel, hexane/ether 5:1) by column chromatography and crystallisation from ether and hexane, the desired product 3-phenyl-1-oxa-2-azaspiro[4.5]dec-2-ene-8-carboxylic acid ethyl ester was obtained as a white solid (190 mg, 25% of the theoretical amount).

7.b. Synthesis of 3-(3-methoxyphenyl)-1-oxa-2-aza-spiro[4.5]dec-2-ene-8-carboxylic acid ethyl ester

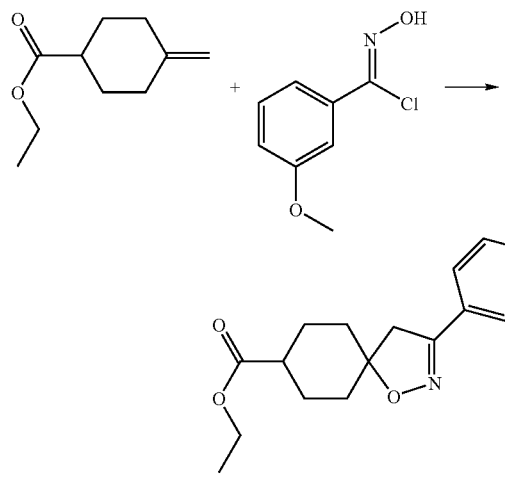

A solution of 1-chloro-1-hydroxyiminomethyl-3-methoxybenzene (31 g, 167 mmol) in DCM (50 ml) was slowly added dropwise to a solution of 4-methylenecyclohexanecarboxylic acid ethyl ester (28 g, 167 mmol) in DCM (950 ml) at 0° C. Subsequently, a solution of triethylamine (50 ml) in DCM (50 ml) was slowly added dropwise at 0° C. and the resulting mixture was stirred overnight at RT. The reaction mixture was diluted with water (500 ml). The combined organic phases were washed with 10% aq. citric acid solution (800 ml) and sat. aq. NaCl solution (500 ml), dried over sodium sulphate and the solvent was removed under vacuum. The desired product 3-(3-methoxyphenyl)-1-oxa-2-azaspiro[4.5]dec-2-ene-8-carboxylic acid ethyl ester (51 g) was reacted without further purification.

7.c. Synthesis of 3-methyl-1-oxa-2-azaspiro[4.5]dec-2-ene-8-carboxylic acid ethyl ester

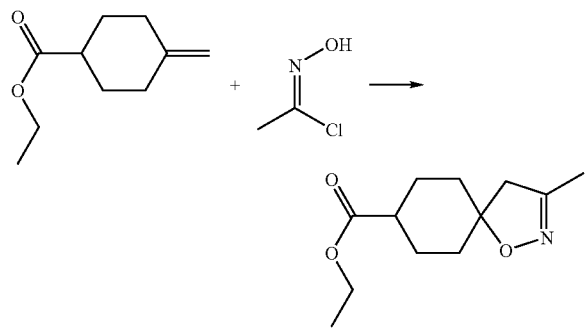

A solution of 1-chloro-1-hydroxyiminoethane (1.5 g, 16 mmol) in DCM (10 ml) was slowly added dropwise to a solution of 4-methylenecyclohexanecarboxylic acid ethyl ester (1.68 g, 10 mmol) in DCM (10 ml) at 0° C. Subsequently, a solution of triethylamine (3 ml) in DCM (10 ml) was slowly added dropwise at 0° C. and the resulting mixture was stirred overnight at RT.

The reaction mixture was diluted with water (50 ml) and DCM. The combined organic phases were washed with 10% aq. citric acid solution (80 ml) and sat. aq. NaCl solution (50 ml), dried over sodium sulphate and the solvent was removed under vacuum. The desired product 3-methyl-1-oxa-2-azaspiro[4.5]dec-2-ene-8-carboxylic acid ethyl ester (2 g) was obtained after purification by column chromatography (SiO$_2$, hexane/EtOAc 1:1).

8.a. Synthesis of 3-phenyl-1-oxa-2-azaspiro[4.5]dec-2-ene-8-carboxylic acid

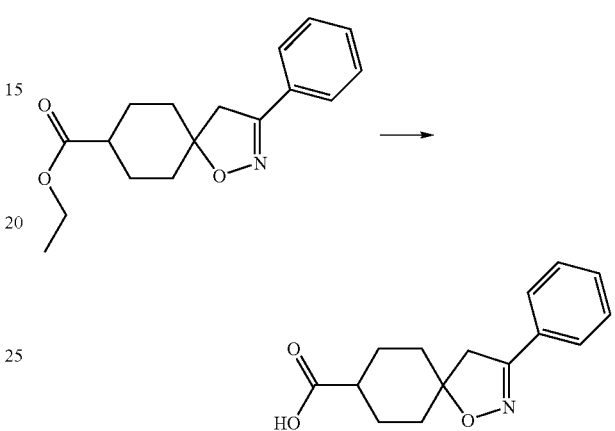

A mixture of 3-phenyl-1-oxa-2-azaspiro[4.5]dec-2-ene-8-carboxylic acid ethyl ester (190 mg, 0.67 mmol) in MeOH (5 ml) and lithium hydroxide monohydrate (74 mg, 1.0 mmol) in H$_2$O (1 ml) was stirred overnight at RT. After removal of the solvent under vacuum, the residue was taken up in 10% aq. citric acid solution and EtOAc and the phases were separated. The aqueous phase was extracted several times with EtOAc, dried over magnesium sulphate and desolventised under vacuum. 150 g (87% of the theoretical amount) of the free acid 3-phenyl-1-oxa-2-azaspiro[4.5]dec-2-ene-8-carboxylic acid was obtained in the form of a colourless solid.

8.b. Synthesis of 3-methoxyphenyl-1-oxa-2-azaspiro[4.5]dec-2-ene-8-carboxylic acid

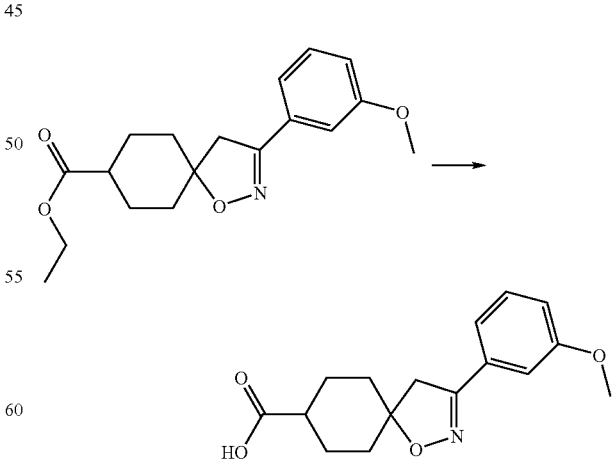

A mixture of 3-(3-methoxyphenyl)-1-oxa-2-azaspiro[4.5]dec-2-ene-8-carboxylic acid ethyl ester (51 g, 161 mmol) in MeOH (1000 ml) and lithium hydroxide monohydrate (18 g, 241 mmol) in H$_2$O (145 ml) was stirred overnight at RT.

The precipitate was removed by suction-filtration and washed with a small amount of ether. The mother liquor was concentrated, taken up in water (200 ml) and the mixture was extracted with EtOAc (3×300 ml). The combined organic phases were adjusted to pH 1 using aq. HCl (25%) and reextracted with EtOAc (3×300 ml). The combined organic phases were washed with activated carbon and dried over magnesium sulphate.

After removal of the solvent under vacuum, 24 g of the free acid 3-methoxyphenyl-1-oxa-2-azaspiro[4.5]dec-2-ene-8-carboxylic acid were obtained in the form of a viscous oil.

8.c. Synthesis of 3-methyl-1-oxa-2-azaspiro[4.5]dec-2-ene-8-carboxylic acid

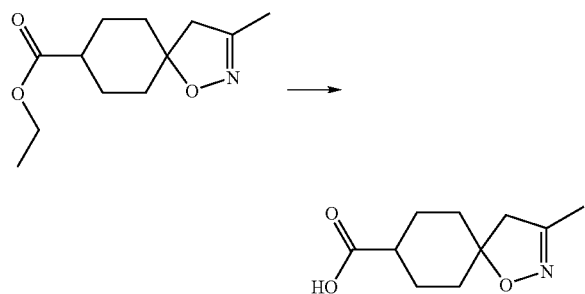

A mixture of 3-methyl-1-oxa-2-azaspiro[4.5]dec-2-ene-8-carboxylic acid ethyl ester (570 mg, 2.5 mmol) in MeOH (15 ml) and lithium hydroxide monohydrate (284 mg, 3.8 mmol) in H$_2$O (3 ml) was stirred overnight at RT.

After removal of the solvent under vacuum, the residue was taken up in 10% aq. citric acid solution and EtOAc and the phases were separated. The aqueous phase was extracted several times with EtOAc, dried over magnesium sulphate and desolventised under vacuum. After removal of the solvent under vacuum, the free acid 3-methyl-1-oxa-2-azaspiro[4.5]dec-2-ene-8-carboxylic acid was obtained.

9. General Directions for Reacting 3-phenyl-1-oxa-2-azaspiro[4.5]dec-2-ene-8-carboxylic Acid with Amines of General Formula HNR$^{11}$R$^{12}$ 3-Phenyl-1-oxa-2-azaspiro[4.5]dec-2-ene-8-carboxylic acid (1 eq.) was slowly added to a solution of N-ethyldiisopropylamine (3 eq.), 1-hydroxybenzotriazole hydrate (1 eq.), O-(benzotriazol-1-yl)-N,N,N',N'-tetramethyluronium tetrafluoroborate (1 eq.) and an amine of general formula HNR$^{11}$R$^{12}$ (1 eq.) in abs. THF. The reaction mixture was stirred overnight and the solvent removed under vacuum. The residue was taken up in EtOAc. The organic phase was washed successively with sat. aq. NaCl solution, sat. aq. NaHCO$_3$ solution, sat. aq. ammonium sulphate solution and sat. aq. NaCl solution, dried over magnesium sulphate and the solvent removed under vacuum. The desired product was obtained as a diastereomer mixture.

9a. Synthesis of Exemplary Compound 50

3-phenyl-1-oxa-2-azaspiro[4.5]dec-2-ene-8-carboxylic acid-(4-tert-butylphenyl)amide

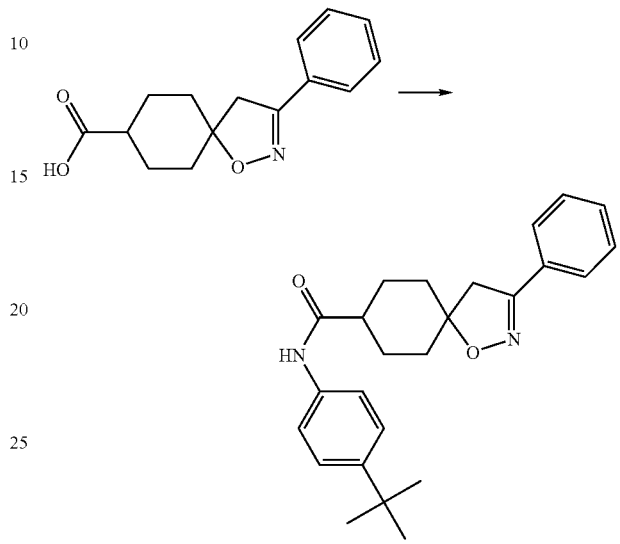

3-Phenyl-1-oxa-2-azaspiro[4.5]dec-2-ene-8-carboxylic acid (400 mg, 1.5 mmol) was slowly added to a solution of N-ethyldiisopropylamine (662 mg, 4.6 mmol), 1-hydroxybenzotriazole hydrate (206 mg, 1.5 mmol), O-(benzotriazol-1-yl)-N,N,N',N'-tetramethyluronium tetrafluoroborate (496 mg, 1.5 mmol) and 4-tert-butylaniline (230 mg, 1.5 mmol) in abs. THF (11 ml). The reaction mixture was stirred overnight and the solvent removed under vacuum. The residue was taken up in EtOAc (75 ml). The organic phase was washed successively with sat. aq. NaCl solution, sat. aq. NaHCO$_3$ solution, sat. aq. ammonium sulphate solution and sat. aq. NaCl solution, dried over magnesium sulphate and the solvent removed under vacuum. The desired product 3-phenyl-1-oxa-2-azaspiro[4.5]dec-2-ene-8-carboxylic acid-(4-tert-butylphenyl)amide was obtained as a diastereomer mixture in a yield of 220 mg (37% of the theoretical amount).

9b. Synthesis of Exemplary Compounds 48 and 49 cis-[4-(3-chloropyridin-2-yl)piperazin-1-yl]-(3-phenyl-1-oxa-2-azaspiro[4.5]dec-2-en-8-yl)methanone and trans-[4-(3-chloropyridin-2-yl)piperazin-1-yl]-(3-phenyl-1-oxa-2-azaspiro[4.5]dec-2-en-8-yl)methanone

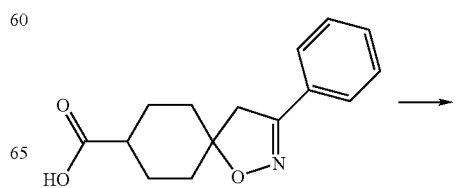

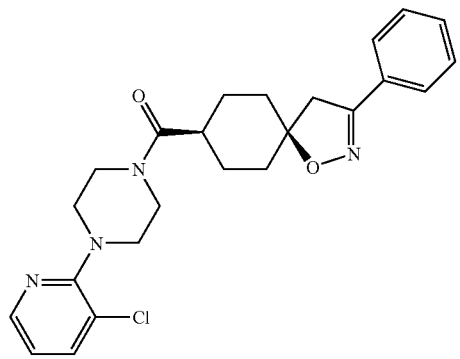

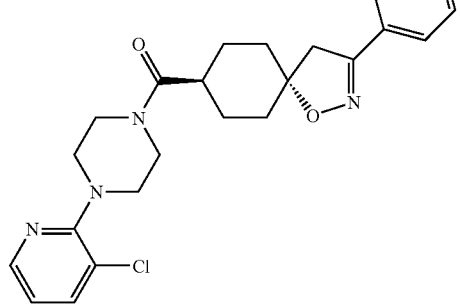

3-Phenyl-1-oxa-2-azaspiro[4.5]dec-2-ene-8-carboxylic acid (750 mg, 2.9 mmol) was slowly added to a solution of N-ethyldiisopropylamine (1.02 g, 7.1 mmol), 1-hydroxybenzotriazole hydrate (320 mg, 2.4 mmol), O-(benzotriazol-1-yl)-N,N,N',N'-tetramethyluronium tetrafluoroborate (758 mg, 2.4 mmol) and 1-(3-chloropyridin-2-yl)piperazine (467 mg, 2.4 mmol) in abs. THF (17 ml). The reaction mixture was stirred overnight and the solvent removed under vacuum. The residue was taken up in EtOAc (100 ml). The precipitate formed was removed by suction-filtration. The organic phase was washed successively with sat. aq. NaCl solution, sat. aq. NaHCO₃ solution, sat. aq. ammonium sulphate solution and sat. aq. NaCl solution, dried over magnesium sulphate and the solvent removed under vacuum. The precipitate and the residue were purified by column chromatography (silica gel, hexane/EtOAc 1:1). The desired product [4-(3-chloropyridin-2-yl)piperazin-1-yl]-(3-phenyl-1-oxa-2-azaspiro[4.5]dec-2-en-8-yl)methanone was obtained as a cis isomer (294 mg, 24% of the theoretical amount) and trans isomer (192 mg, 15% of the theoretical amount).

9c. Synthesis of Exemplary Compounds 52 and 53

3-phenyl-1-oxa-2-azaspiro[4.5]dec-2-ene-8-carboxylic acid-cis-3-fluoro-4-methanesulphonylaminobenzylamide and 3-phenyl-1-oxa-2-azaspiro[4.5]dec-2-ene-8-carboxylic acid-trans-3-fluoro-4-methanesulphonylaminobenzylamide

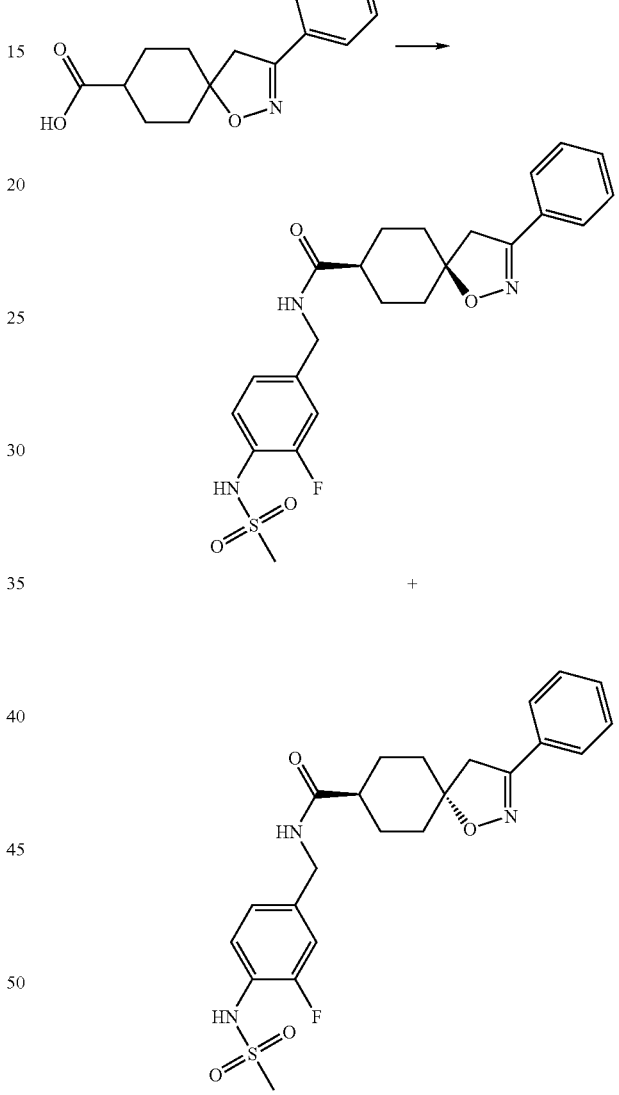

3-Phenyl-1-oxa-2-azaspiro[4.5]dec-2-ene-8-carboxylic acid (400 mg, 1.54 mmol) was slowly added to a solution of N-ethyldiisopropylamine (662 g, 4.6 mmol), 1-hydroxybenzotriazole hydrate (206 mg, 1.54 mmol), O-(benzotriazol-1-yl)-N,N,N',N'-tetramethyluronium tetrafluoroborate (496 mg, 1.54 mmol) and N-(4-aminomethyl-2-fluorophenyl)methanesulphonamide (336 mg, 1.54 mmol) in abs. THF (11 ml). The reaction mixture was stirred overnight and the solvent removed under vacuum. The residue was taken up in EtOAc (75 ml). The precipitate formed was removed by suction-filtration, washed with a small amount of ether and dried. The desired product 3-phenyl-1-oxa-2-azaspiro[4.5]dec-2-ene-8-carboxylic acid-3-fluoro-4-methanesulphonylaminobenzylamide was obtained as a cis isomer (89 mg, 13% of the theoretical amount). The organic phase was washed successively with sat. aq. NaCl solution, sat. aq. NaHCO₃ solution, sat. aq. ammonium sulphate solution and sat. aq. NaCl solution, dried over magnesium sulphate and the solvent removed under vacuum. The residue was boiled up in EtOAc (2.5 ml) and DCM (1 ml). The precipitate formed was removed by suction-filtration and washed with a small amount of ether. The desired product 3-phenyl-1-oxa-2-azaspiro[4.5]dec-2-ene-8-carboxylic acid-3-fluoro-4-methanesulphonylaminobenzylamide was obtained as a trans isomer (138 mg, 19% of the theoretical amount).

9d. Synthesis of Exemplary Compound 57

N-(4-tert-butylphenyl)-3-methyl-1-oxa-2-azaspiro[4.5]dec-2-ene-8-carboxamide

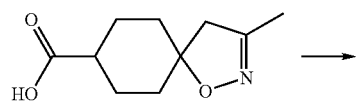 

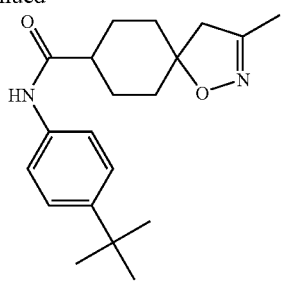

N,N'-diisopropylcarbodiimide (96 mg, 0.76 mmol) was added to a solution of 3-methyl-1-oxa-2-azaspiro[4.5]dec-2-ene-8-carboxylic acid (150 mg, 0.76 mmol) in DCM (40 ml). The reaction mixture was mixed after 30 minutes with 1-hydroxybenzotriazole hydrate (HOBt, 101 mg, 0.76 mmol) and tert-butylaniline (113 mg, 0.76 mmol), stirred overnight and the solvent removed under vacuum. The residue was taken up in EtOAc. The organic phase was washed successively with diluted aq. citric acid solution and sat. aq. NaCl solution, dried over magnesium sulphate and the solvent removed under vacuum. The desired product N-(4-tert-butylphenyl)-3-methyl-1-oxa-2-azaspiro[4.5]dec-2-ene-8-carboxamide was obtained after purification by column chromatography (SiO₂, hexane/EtOAc 1:1) as a diastereomer mixture in a yield of 66 mg.

The following substituted spiro compounds according to the invention were prepared as described under 4.

| | Name | [M + H] |
|---|---|---|
| 33 | 3-methyl-1-oxa-2-azaspiro[4.5]dec-2-ene-8-carboxylic acid-(4-tert-butylphenyl)amide | 365.9 |
| 46 | cis-[3-(4-tert-butylphenyl)-1-oxa-2-azaspiro[4.5]dec-2-en-8-yl]-[4-(3-chloropyridin-2-yl)piperazin-1-yl]methanone | 496.1 |
| 47 | trans-[3-(4-tert-butylphenyl)-1-oxa-2-azaspiro[4.5]dec-2-en-8-yl]-[4-(3-chloropyridin-2-yl)piperazin-1-yl]methanone | 496.1 |
| 48 | cis-[4-(3-chloropyridin-2-yl)piperazin-1-yl]-(3-phenyl-1-oxa-2-azaspiro[4.5]dec-2-en-8-yl)methanone | 440.0 |
| 49 | trans-[4-(3-chloropyridin-2-yl)piperazin-1-yl]-(3-phenyl-1-oxa-2-azaspiro[4.5]dec-2-en-8-yl)methanone | 440.0 |
| 50 | 3-phenyl-1-oxa-2-azaspiro[4.5]dec-2-ene-8-carboxylic acid-(4-tert-butylphenyl)amide | 391.5 |
| 51 | 3-phenyl-1-oxa-2-azaspiro[4.5]dec-2-ene-8-carboxylic acid cis-(4-tert-butylphenyl)amide | 391.5 |
| 52 | 3-phenyl-1-oxa-2-azaspiro[4.5]dec-2-ene-8-carboxylic acid cis-3-fluoro-4-methanesulphonylaminobenzylamide | 460.5 |
| 53 | 3-phenyl-1-oxa-2-azaspiro[4.5]dec-2-ene-8-carboxylic acid trans-3-fluoro-4-methanesulphonylaminobenzylamide | 460.5 |
| 93 | 3-(3-methoxyphenyl)-1-oxa-2-azaspiro[4.5]dec-2-ene-8-carboxylic acid-(4-pentafluorosulphanylphenyl)amide | |
| 62 | (4-(3-chloropyridin-2-yl)piperazin-1-yl)(3-(3-methoxyphenyl)-1-oxa-2-azaspiro[4.5]dec-2-en-8-yl)methanone | |
| 63 | 3-(3-methoxyphenyl)-N-(4-(trifluormethoxy)benzyl)-1-oxa-2-azaspiro[4.5]dec-2-ene-8-carboxamide | |
| 64 | N-(1H-indol-5-yl)-3-(3-methoxyphenyl)-1-oxa-2-azaspiro[4.5]dec-2-ene-8-carboxamide | |
| 65 | N-(3-fluoro-4-(methylsulphonamido)benzyl)-3-(3-methoxyphenyl)-1-oxa-2-azaspiro[4.5]dec-2-ene-8-carboxamide | |
| 66 | N-(4-tert-butylphenyl)-3-(3-methoxyphenyl)-1-oxa-2-azaspiro[4.5]dec-2-ene-8-carboxamide | |
| 67 | N-(2,3-dihydrobenzo[b][1,4]dioxin-6-yl)-3-(3-methoxyphenyl)-1-oxa-2-azaspiro[4.5]dec-2-ene-8-carboxamide | |
| 68 | N-(4-tert-butylphenyl)-3-(4-fluorophenyl)-1-oxa-2-azaspiro[4.5]dec-2-ene-8-carboxamide | |
| 69 | (5R,8R)-3-phenyl-N-((2-(piperidin-1-yl)-6-(trifluormethyl)pyridin-3-yl)methyl)-1-oxa-2-azaspiro[4.5]dec-2-ene-8-carboxamide | |
| 70 | (5R,8R)-N-((2-(4-methylpiperidin-1-yl)-6-(trifluormethyl)pyridin-3-yl)methyl)-3-phenyl-1-oxa-2-azaspiro[4.5]dec-2-ene-8-carboxamide | |

| Name | [M + H] |
|---|---|
| 71 (5S,8S)-N-((2-(3-chloro-4-fluorophenyl)-6-(trifluormethyl)pyridin-3-yl)methyl)-3-phenyl-1-oxa-2-azaspiro[4.5]dec-2-ene-8-carboxamide | |
| 72 (5S,8S)-N-((2-(4-methylpiperidin-1-yl)-6-(trifluormethyl)pyridin-3-yl)methyl)-3-phenyl-1-oxa-2-azaspiro[4.5]dec-2-ene-8-carboxamide | |
| 73 (5S,8S)-3-phenyl-N-((2-(piperidin-1-yl)-6-(trifluormethyl)pyridin-3-yl)methyl)-1-oxa-2-azaspiro[4.5]dec-2-ene-8-carboxamide | |
| 74 (5R,8R)-N-(2,3-dihydrobenzo[b][1,4]dioxin-6-yl)-3-phenyl-1-oxa-2-azaspiro[4.5]dec-2-ene-8-carboxamide | |
| 75 (5S,8S)-N-(2,3-dihydrobenzo[b][1,4]dioxin-6-yl)-3-phenyl-1-oxa-2-azaspiro[4.5]dec-2-ene-8-carboxamide | |

10. Synthesis of 2-methylenedecahydronaphthalene

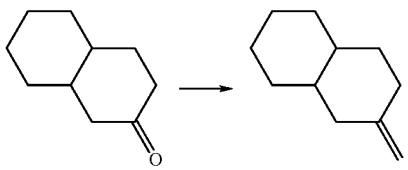

Methyltriphenylphosphonium bromide (89.2 g, 249 mmol) was placed in abs. diethyl ether (800 ml) under a nitrogen atmosphere. At 0° C. potassium tert-butylate (34 g, 295 mmol) was slowly added. After 30 min octahydronaphthalen-2-one (25 g, 164 mmol) as a solution in diethyl ether (500 ml) was slowly added dropwise, again at 0° C. The reaction mixture was stirred overnight at RT. For working up, the reaction mixture was cooled in an ice bath and mixed with sat. aq. $NH_4Cl$ solution. The phases were separated and the aqueous phase was shaken out several times with EtOAc. The combined organic phases were dried over magnesium sulphate and the solvent was removed under vacuum. The residue was taken up in hexane/ether 1:1, removed by suction-filtration and the residue washed with hexane/ether 1:1. The filtrate was concentrated and the residue also removed by suction-filtration. The desired compound 2-methylene-decahydronaphthalene was obtained as a solid (16.3 g, 66% of the theoretical amount).

11. Synthesis of 4-tert-butylbenzaldehyde oxime

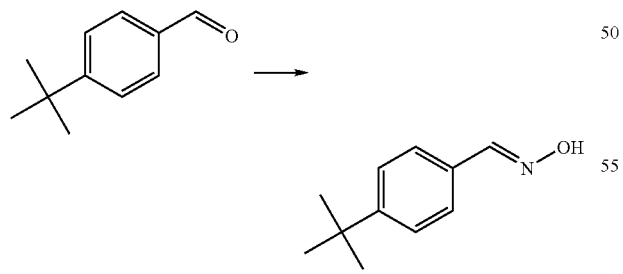

Hydroxylamine hydrochloride (4.65 g, 67.4 mmol) was slowly added to a solution of 4-tert-butylbenzaldehyde (10 g, 61.6 mmol) in water (34 ml) and EtOH (7 ml). An aqueous solution of sodium hydroxide (3.6 g, 153 mmol) was slowly added dropwise, so the temperature of the reaction mixture did not exceed 25° C. The reaction mixture was stirred overnight at RT and mixed with diethyl ether. The aqueous phase was neutralised with 0.5 M aq. hydrochloric acid solution and extracted several times with ether. The combined organic phases were dried over magnesium sulphate and the solvent was removed under vacuum. The desired product 4-tert-butylbenzaldehyde oxime was obtained in a yield of 84% of the theoretical amount (9.1 g)

12. Synthesis of 1-chloro-1-hydroxyiminomethyl-4-tert-butylbenzene

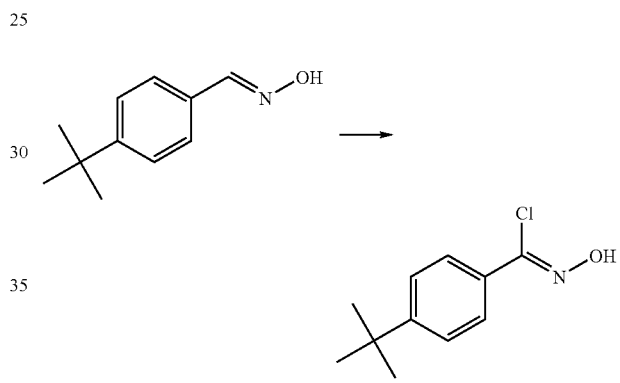

N-chlorosuccinimide (8.1 g, 61 mmol) was added to a solution of 4-tert-butylbenzaldehyde oxime (9 g, 50.1 mmol) in DMF (50 ml) at RT, causing the temperature to rise briefly to 50° C. The reaction mixture was cooled in an ice bath, stirred for 3 h at RT, mixed with water (100 ml) while being cooled with ice and extracted with ether (3×100 ml). The combined organic phases were washed with water (150 ml) and sat. aq. NaCl solution (150 ml), dried and the solvent was removed under vacuum. The desired product 1-chloro-1-hydroxyiminomethyl-4-tert-butylbenzene was obtained as a yellowish solid (10.7 g).

13. Synthesis of Exemplary Compound 40

4-tert-butyl-3-phenyl-3',4',4a',5',6',7',8',8a'-octahydro-1'H,4H-spiro[isoxazol-5,2'-naphthalene]

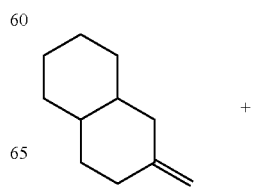 +

-continued

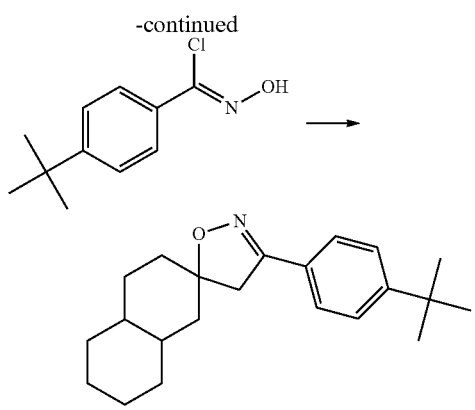

A solution of 1-chloro-1-hydroxyiminomethyl-4-tert-butylbenzene (272 mg, 1.3 mmol) in DCM (5 ml) was slowly added dropwise to a solution of 2-methylenedecahydronaphthalene (150 mg, 1 mmol) in DCM (5 ml) at 0° C. Subsequently, a solution of triethylamine (312 mg) in DCM (5 ml) was slowly added dropwise at 0° C. and the resulting mixture was stirred overnight at RT.

The reaction mixture was diluted with DCM and with water. The combined organic phases were washed with 10% aq. citric acid solution and sat. aq. NaCl solution, dried over sodium sulphate and the solvent was removed under vacuum. The desired product 4-tert-butyl-3-phenyl-3',4',4a',5',6',7',8',8a'-octahydro-1'H,4H-spiro[isoxazol-5,2'-naphthalene] was obtained in an amount of 212 mg.

Examples 34 to 39 and 41 to 45 were synthesised similarly to the synthesis of Example 40, as is described under 10. to 13.

| | Name | [M + H] |
|---|---|---|
| 34 | 3-phenyl-3',4',4a',5',6',7',8',8a'-octahydro-1'H,4H-spiro[isoxazol-5,2'-naphthalene] | 270.4 |
| 35 | 3,8-diphenyl-1-oxa-2-azaspiro[4.5]dec-2-ene | 292.4 |
| 36 | 8 phenyl-3-p-tolyl-1-oxa-2-azaspiro[4.5]dec-2-ene | 306.4 |
| 37 | 8 phenyl-3-(4-trifluormethylphenyl)-1-oxa-2-azaspiro[4.5]dec-2-ene | 360.4 |
| 38 | 7,7,9,9-tetramethyl-3-phenyl-1-oxa-2-azaspiro[4.5]dec-2-ene | 272.4 |
| 39 | 3-(4-tert-butylphenyl)-8 phenyl-1-oxa-2-azaspiro[4.5]dec-2-ene | 348.5 |
| 40 | 4-tert-butyl-3-phenyl-3',4',4a',5',6',7',8',8a'-octahydro-1'H,4H-spiro[isoxazol-5,2'-naphthalene] | 326.5 |
| 41 | 3-(4-tert-butylphenyl)-7,7,9,9-tetramethyl-1-oxa-2-azaspiro[4.5]dec-2-ene | 328.5 |
| 42 | 8 phenyl-3-pyridin-2-yl-1-oxa-2-azaspiro[4.5]dec-2-ene | 293.4 |
| 43 | 8-(1,1-dimethylpropyl)-3-pyridin-2-yl-1-oxa-2-azaspiro[4.5]dec-2-ene | 287.4 |
| 44 | 3-(4-tert-butylphenyl)-8-(1,1-dimethylpropyl)-1-oxa-2-azaspiro[4.5]dec-2-ene | 342.5 |
| 45 | 3-(4-tert-butylphenyl)-8-ethyl-1-oxa-2-azaspiro[4.5]dec-2-ene | 300.5 |

Pharmacological Data

The affinity of the Spiro compounds according to the invention for the vanilloid receptor 1 (VR1/TRPV1 receptor) was determined as described hereinbefore.

| Compound according to the example | VR1 (human) (% stimulation compared to 10 μM CP) | VR1 (human) (% inhibition compared to 10 μM CP) | VR1 (rat) (% stimulation compared to 10 μM CP) | VR1 (rat) (% inhibition compared to 10 μM CP) |
|---|---|---|---|---|
| 1 | 20.67 | 23.56 | 44.72 | 71.32 |
| 2 | −0.32 | 58.09 | −15.97 | 100.87 |
| 3 | −1.29 | 80.10 | 0.10 | 102.62 |
| 4 | −0.33 | 76.33 | −0.54 | 73.69 |
| 7 | −0.05 | 92.79 | 0.23 | 105.33 |
| 8 | 0.22 | 20.73 | 0.57 | 97.15 |
| 9 | 0.41 | 61.74 | 1.05 | 91.46 |
| 10 | 2.84 | 17.54 | 8.77 | 22.95 |
| 11 | −0.05 | 28.56 | −0.37 | 62.42 |
| 12 | 100.98 | 79.89 | 112.30 | 94.31 |
| 17 | −0.05 | 14.95 | 0.33 | 58.92 |
| 18 | 24.24 | 22.05 | 84.04 | 97.62 |
| 19 | 13.41 | 22.55 | 70.81 | 95.49 |
| 21 | −0.05 | 6.75 | 0.37 | 52.32 |
| 22 | 0.13 | 0.14 | −0.37 | 16.63 |
| 23 | 23.79 | 54.21 | 55.21 | 69.46 |
| 24 | 91.72 | 83.01 | 87.96 | 97.79 |
| 25 | 0.16 | 56.47 | 1.04 | 98.31 |
| 50 | 15 | 64 | 60 | 97 |
| 51 | 17 | 25 | 73 | 91 |
| 58 | 27 | 67 | 46 | 107 |
| 66 | 53 | 54 | 87 | 101 |
| 80 | 35 | 42 | 48 | 103 |
| 84 | 33 | 31 | 61 | 103 |
| 90 | 36 | 34 | 43 | 100 |

| Compound according to the example | $K_i$ CAP rat [μM] | $K_i$ CAP human [μM] | $IC_{50}$ CAP rat [μM] | $IC_{50}$ CAP human [μM] |
|---|---|---|---|---|
| 7 | 0.0797 | 1.989 | 0.126 | 1.24 |
| 9 | 0.894 | 4.861 | 1.55 | 3.34 |
| 50 | 0.0637 | | 0.545 | |
| 80 | 0.341 | 2.05 | 1.22 | 2.87 |

The invention claimed is:
1. A substituted spiro compound corresponding to formula I

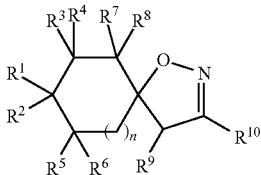

wherein
n is 0, 1 or 2; and
I.)
$R^1$ denotes:
- a linear or branched, saturated or unsaturated, unsubstituted or mono- or polysubstituted aliphatic group optionally containing one or more heteroatoms as chain members; or
- an unsubstituted or mono- or polysubstituted, unsaturated or saturated cycloaliphatic group which optionally contains one or more heteroatoms as ring members, and which optionally may be bound via a linear or branched, unsubstituted or mono- or polysubstituted alkylene, alkenylene or alkinylene group optionally containing one or more heteroatoms as chain members, and which optionally may be condensed with an unsubstituted or mono- or polysubstituted mono- or polycyclic ring system, wherein the cycloaliphatic group is optionally substituted with one or more substituents independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —S(=O)$_2$—NH—C$_{1-5}$ alkyl, cyclohexyl, cyclopentyl, pyridinyl, pyridazinyl, —(CH$_2$)-benzo[b]furanyl, —O-phenyl, —O-benzyl, phenyl and benzyl, wherein the cyclic portion of pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl is optionally substituted with 1, 2, 3, 4 or 5 substituents selected independently of one another from the group consisting of F, Cl, Br, —OH, —CF$_3$, —CN, —NO$_2$, —C$_{1-5}$ alkyl, —O—C$_{1-5}$ alkyl, —O—CF$_3$—S—CF$_3$, phenyl and —O-benzyl; or
- an unsubstituted or mono- or polysubstituted aryl or heteroaryl group which optionally may be bound via a linear or branched, unsubstituted or mono- or polysubstituted alkylene, alkenylene or alkinylene group optionally containing one or more heteroatoms as chain members, and which optionally may be condensed with an unsubstituted or mono- or polysubstituted mono- or polycyclic ring system; or
- a —C(=O)—NR$^{11}$R$^{12}$ group;
and
$R^2$, $R^3$, $R^4$, $R^5$, $R^6$, $R^7$ and $R^8$ each independently denote hydrogen, or
  - a linear or branched, saturated or unsaturated, unsubstituted or mono- or polysubstituted aliphatic group optionally containing one or more heteroatoms as chain members;
or
II.)
$R^1$ and $R^3$ together denote a —(CH$_2$)$_p$— group, wherein p is 3, 4, 5 or 6;
and
$R^2$, $R^4$, $R^5$, $R^6$, $R^7$ and $R^8$ each independently denote hydrogen, or
  - a linear or branched, saturated or unsaturated, unsubstituted or mono- or polysubstituted aliphatic group optionally containing one or more heteroatoms as chain members;
or
$R^1$, $R^2$, $R^7$ and $R^8$ each denote hydrogen, and
$R^3$, $R^4$, $R^5$ and $R^6$ each independently denote a linear or branched, saturated or unsaturated, unsubstituted or mono- or polysubstituted aliphatic group optionally containing one or more heteroatoms as chain members;
and
$R^9$ denotes hydrogen, or
- a linear or branched, saturated or unsaturated, unsubstituted or mono- or polysubstituted aliphatic group optionally containing one or more heteroatoms as chain members; or
- an unsubstituted or mono- or polysubstituted, unsaturated or saturated cycloaliphatic group which optionally contains one or more heteroatoms as ring members, and which optionally may be bound via a linear or branched, unsubstituted or mono- or polysubstituted alkylene, alkenylene or alkinylene group optionally containing one or more heteroatoms as chain members, and which optionally may be condensed with an unsubstituted or mono- or polysubstituted mono- or polycyclic ring system; or
- an unsubstituted or mono- or polysubstituted aryl or heteroaryl group which optionally may be bound via a linear or branched, unsubstituted or mono- or polysubstituted alkylene, alkenylene or alkinylene group optionally containing one or more heteroatoms as chain members, and which optionally may be condensed with an unsubstituted or mono- or polysubstituted mono- or polycyclic ring system;
$R^{10}$ denotes:
- a linear or branched, saturated or unsaturated, unsubstituted or mono- or polysubstituted aliphatic group optionally containing one or more heteroatoms as chain members; or
- an unsubstituted or mono- or polysubstituted phenyl group, with the proviso that either of the two meta positions and the para position of said phenyl group are not both substituted with substituents which are bound to the phenyl group via identical atoms selected from the group consisting of oxygen, sulfur and nitrogen; or
- an unsubstituted or mono- or polysubstituted group selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]- tetrahydroquinazolinyl; 2H-benzo[1.4]oxazin-3(4H)-onyl, (3,4)-dihydroquinolin-2(1H)-onyl, [3,4]-dihydro-2H-1,4-benzoxazinyl and benzothiazolyl; or an unsubstituted or mono- or polysubstituted aryl or heteroaryl group which is bound via a —(CH$_2$)—, —(CH$_2$)$_2$— or —(CH$_2$)$_3$ group, and which optionally may be condensed with an unsubstituted or mono- or polysubstituted mono- or polycyclic ring system; or a —C(=O)—NR$^{13}$R$^{14}$ group;

R$^{11}$ and R$^{13}$ each independently denote:

a linear or branched, saturated or unsaturated, unsubstituted or mono- or polysubstituted aliphatic group; or an unsubstituted or mono- or polysubstituted, unsaturated or saturated cycloaliphatic group which optionally contains one or more heteroatoms as ring members, and which optionally may be bound via a —(CH$_2$)$_w$— group, wherein w is 1, 2, 3, 4 or 5, and which optionally may be condensed with an unsubstituted or mono- or polysubstituted mono- or polycyclic ring system; or an unsubstituted or mono- or polysubstituted aryl or heteroaryl group which optionally may be bound via a —(CH$_2$)—, —(CH$_2$)$_2$— or —(CH$_2$)$_3$ group, and which optionally may be condensed with an unsubstituted or mono- or polysubstituted mono- or polycyclic ring system;

R$^{12}$ and R$^{14}$ each independently denote hydrogen, or a linear or branched, saturated or unsaturated, unsubstituted or mono- or polysubstituted aliphatic group;

an unsubstituted or mono- or polysubstituted, unsaturated or saturated cycloaliphatic group which optionally contains one or more heteroatoms as ring members, and which optionally may be bound via a linear or branched, unsubstituted or mono- or polysubstituted alkylene, alkenylene or alkinylene group optionally containing one or more heteroatoms as chain members, and which optionally may be condensed with an unsubstituted or mono- or polysubstituted mono- or polycyclic ring system; or or an unsubstituted or mono- or polysubstituted aryl or heteroaryl group which optionally may be bound via a —(CH$_2$)— group, and which optionally may be condensed with an unsubstituted or mono- or polysubstituted mono- or polycyclic ring system;

or

R$^{11}$ and R$^{12}$, or R$^{13}$ and R$^{14}$, respectively, together with the nitrogen atom to which they are bound form an unsubstituted or mono- or polysubstituted, unsaturated or saturated heterocycloaliphatic ring which optionally contains one or more further heteroatoms as rign members, and which optionally may be condensed with an unsubstituted or mono- or polysubstituted mono- or polycyclic ring system;

wherein substituents of the above-mentioned heterocycloaliphatic group formed by R$^{11}$ and R$^{12}$, or by R$^{13}$ and R$^{14}$, are independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—NH$_2$, —C(=O)—NH—C$_{1-5}$ alkyl, —C(=O)—N—(C$_{1-5}$ alkyl)$_2$, cyclohexyl, cyclopentyl, pyridinyl, pyridazinyl, pyrimidinyl, [1,2,5]-thiadiazolyl, thiazolyl, —(CH$_2$)-benzo[b]furanyl, —O-phenyl, —O-benzyl, phenyl and benzyl, wherein the cyclic portion of a pyrimidinyl, [1,2,5]-thiadiazolyl, thiazolyl, pyridinyl, cyclopentyl, cyclohexyl, pyridazinyl, —O-phenyl, —O-benzyl, phenyl, —(CH$_2$)-benzo[b]furanyl and benzyl group optionally may be substituted with substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl; and substituents of the above-mentioned aliphatic groups are independently selected from the group consisting of F, Cl, Br, I, —CN, —NO$_2$, —OH, —SH and —NH$_2$;

or a salt or solvate thereof.

2. A compound according to claim 1, wherein said compound is present in the form of an isolated or purified stereoisomer.

3. A compound according to claim 1, wherein said compound is present in the form of a mixture of stereoisomers in any mixing ratio.

4. A compound according to claim 3, wherein said compound is present in the form of a racemic mixture.

5. A compound according to claim 1, wherein n is 0, 1 or 2;

I.)

R$^1$ denotes:

a linear or branched, saturated or unsaturated, optionally substituted C$_{1-10}$ aliphatic group;

an unsaturated or saturated, optionally substituted 3, 4, 5, 6, 7, 8 or 9-membered cycloaliphatic group which optionally may be condensed with a saturated, unsaturated or aromatic, optionally substituted mono- or polycyclic ring system;

an optionally substituted 5 to 14-membered aryl or heteroaryl group which optionally may be condensed with a saturated or unsaturated, optionally substituted mono- or polycyclic ring system;

a —C(=O)—NR$^{11}$R$^{12}$ group; or

—(CHR$^{15}$)—X$_e$—(CHR$^{16}$)$_f$—Y$_g$—(CHR$^{17}$)$_h$—Z$_k$—R$^{18}$ wherein e=0 or 1, f=0 or 1, g=0 or 1, h=0 or 1 and k=0 or 1, wherein X, Y and Z each independently denote O, S, NH, N(CH$_3$), N(C$_2$H$_5$) or N[CH(CH$_3$)$_2$];

and

R$^2$, R$^3$, R$^4$, R$^5$, R$^6$, R$^7$ and R$^8$ each independently denote hydrogen, or a linear or branched, saturated or unsaturated, optionally substituted C$_{1-10}$ aliphatic group;

or

II.)

R$^1$ and R$^3$ together denote a —(CH$_2$)$_p$ group wherein p=3, 4, 5 or 6; and R$^2$, R$^4$, R$^5$, R$^6$, R$^7$ and R$^8$ each independently denote hydrogen, or a linear or branched, saturated or unsaturated, optionally substituted C$_{1-10}$ aliphatic group;

or

III.)

R$^1$, R$^2$, R$^7$ and R$^8$ each independently denote hydrogen, and

R$^3$, R$^4$, R$^5$ and R$^6$ each independently denote a linear or branched, saturated or unsaturated, optionally substituted C$_{1-10}$ aliphatic group;

and

R$^9$ denotes hydrogen, or a linear or branched, saturated or unsaturated, optionally substituted C$_{1-10}$ aliphatic group; or an unsaturated or saturated, optionally substituted 3, 4, 5, 6, 7, 8 or 9-membered cycloaliphatic group which optionally may be condensed with a saturated, unsaturated or aromatic, optionally substituted mono- or polycyclic ring system; or an optionally substituted 5 to 14-membered aryl or heteroaryl group which optionally may be condensed with a saturated or unsaturated, optionally substituted mono- or polycyclic ring system; or
—(CHR$^{19}$)—X$_q$—(CHR$^{20}$)$_r$—Y$_s$—(CHR$^{21}$)$_t$—Z$_u$—R$^{22}$, wherein q is 0 or 1; r is 0 or 1; s is 0 or 1; t is 0 or 1; u is 0 or 1; and X, Y and Z each independently denote O, S, NH, N(CH$_3$), N(C$_2$H$_5$) or N[CH(CH$_3$)$_2$];

R$^{10}$ denotes:
  a linear or branched, saturated or unsaturated, optionally substituted C$_{1-10}$ aliphatic group; or
  a phenyl group which may be unsubstituted or substituted with 1, 2, 3, 4 or 5 substituents independently selected from the group consisting of F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-10}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —NH—S(=O)$_2$—C$_{1-5}$ alkylenephenyl, —NH—S(=O)$_2$—C$_{1-5}$ alkylenenaphthyl, —NH—S(=O)$_2$ phenyl, —NH—S(=O)$_2$ naphthyl, cyclohexyl, cyclopentyl, morpholinyl, piperidinyl, piperazinyl, pyrrolidinyl, pyridinyl, pyridazinyl, —(CH$_2$)-benzo[b]furanyl, —O-phenyl, —O-benzyl, phenyl and benzyl;
    wherein the cyclic portion of a pyridinyl, cyclopentyl, cyclohexyl, morpholinyl, piperidinyl, piperazinyl, pyrrolidinyl, pyridinyl, pyridazinyl, —S(=O)$_2$ phenyl, —O-phenyl, —O-benzyl, phenyl, —(CH$_2$)-benzo[b]furanyl, —NH—S(=O)$_2$—C$_{1-5}$ alkylenephenyl, —NH—S(=O)$_2$—C$_{1-5}$ alkylenenaphthyl, —NH—S(=O)$_2$ phenyl, —NH—S(=O)$_2$naphthyl or benzyl group optionally may be substituted with 1, 2, 3, 4 or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, CF$_3$, phenyl and —O-benzyl;
  with the proviso that either of the two meta positions and the para position of said phenyl group are not both substituted with substituents which are respectively bound to the phenyl group via identical atoms selected from the group consisting of oxygen, sulfur and nitrogen; or
  an optionally substituted group selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl; 2H-benzo[1.4]oxazin-3(4H)-onyl, (3,4)-dihydroquinolin-2(1H)-onyl, [3,4]-dihydro-2H-1,4-benzoxazinyl and benzothiazolyl; or
  an optionally substituted 5 to 14-membered aryl or heteroaryl group which optionally may be condensed with a saturated or unsaturated, optionally substituted mono- or polycyclic ring system, and which is bound via a —(CH$_2$)—, —(CH$_2$)$_2$— or —(CH$_2$)$_3$— group; or
  a —C(=O)—NR$^{13}$R$^{14}$ group;

R$^{11}$ and R$^{13}$ each independently denote:
  a linear or branched, saturated or unsaturated, optionally substituted C$_{1-10}$ aliphatic group; or
  an unsaturated or saturated, optionally substituted 3, 4, 5, 6, 7, 8 or 9-membered cycloaliphatic group which optionally may be condensed with a saturated, unsaturated or aromatic, optionally substituted mono- or polycyclic ring system or bound via a —(CH$_2$)$_w$— group wherein w=1, 2, 3, 4 or 5; or
  an optionally substituted 5 to 14-membered aryl or heteroaryl group which optionally may be condensed with a saturated or unsaturated, optionally substituted mono- or polycyclic ring system, and which optionally may be bound via a —(CH$_2$)—, —(CH$_2$)$_2$— or —(CH$_2$)$_3$ group;

R$^{12}$ and R$^{14}$ each independently denote hydrogen, or
  a linear or branched, saturated or unsaturated, optionally substituted C$_{1-10}$ aliphatic group; or
  an unsaturated or saturated, optionally substituted 3, 4, 5, 6, 7, 8 or 9-membered cycloaliphatic group which optionally may be condensed with a saturated, unsaturated or aromatic, optionally substituted mono- or polycyclic ring system, and which optionally may be bound via a —(CH$_2$)$_w$— group, wherein w=1, 2, 3, 4 or 5; or
  an optionally substituted 5 to 14-membered aryl or heteroaryl group which optionally may be condensed with a saturated or unsaturated, optionally substituted mono- or polycyclic ring system, and which optionally may be bound via a —(CH$_2$) group;

or
R$^{11}$ and R$^{12}$, or R$^{13}$ and R$^{14}$, respectively, together with the nitrogen atom to which they are bound form a saturated or unsaturated, optionally substituted 4, 5, 6, 7, 8 or 9-membered heterocycloaliphatic ring which optionally may be condensed with a saturated, unsaturated or aromatic, optionally substituted mono- or polycyclic ring system;

R$^{15}$, R$^{16}$, R$^{17}$, R$^{19}$, R$^{20}$ and R$^{21}$ each independently denote hydrogen, or
  a linear or branched, saturated or unsaturated, optionally substituted C$_{1-10}$ aliphatic group;

and
R$^{18}$ and R$^{22}$ each independently denote:
  a linear or branched, saturated or unsaturated, optionally substituted C$_{1-10}$ aliphatic group; or
  an unsaturated or saturated, optionally substituted 3, 4, 5, 6, 7, 8 or 9-membered cycloaliphatic group which optionally may be condensed with a saturated, unsaturated or aromatic, optionally substituted mono- or polycyclic ring system; or
  an optionally substituted 5 to 14-membered aryl or heteroaryl group which optionally may be condensed with a saturated or unsaturated, optionally substituted mono- or polycyclic ring system;

wherein
  the above-mentioned C$_{1-10}$ aliphatic groups each may optionally be substituted with 1, 2, 3, 4, 5, 6, 7, 8 or 9 substituents independently selected from the group consisting of F, Cl, Br, I, —CN, —NO$_2$, —OH, —SH and —NH$_2$;
  the above-mentioned cycloaliphatic groups each may optionally be substituted with 1, 2, 3, 4 or 5 substituents independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —S(=O)$_2$—NH—C$_{1-5}$ alkyl, cyclohexyl, cyclopentyl, pyridinyl, pyridazinyl, —(CH$_2$)-benzo[b]furanyl, —O-phenyl, —O-benzyl, phenyl and benzyl groups;
  wherein the cyclic portion of a pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl group optionally may be substituted with 1, 2, 3, 4 or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl;
the above-mentioned cycloaliphatic groups each may optionally contain 1, 2, 3, 4 or 5 heteroatoms independently selected from the group consisting of oxygen, nitrogen and sulfur as ring members;
the above-mentioned heterocycloaliphatic groups formed by R$^{11}$ and R$^{12}$, or by R$^{13}$ and R$^{14}$, optionally may be substituted with 1, 2, 3, 4 or 5 substituents independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—NH$_2$, —C(=O)—NH—C$_{1-5}$ alkyl, —C(=O)—N—(C$_{1-5}$ alkyl)$_2$, cyclohexyl, cyclopentyl, pyridinyl, pyridazinyl, pyrimidinyl, [1,2,5]-thiadiazolyl, thiazolyl, —(CH$_2$)-benzo[b]furanyl, —O-phenyl, —O-benzyl, phenyl and benzyl;
  wherein the cyclic portion of a pyrimidinyl, [1,2,5]-thiadiazolyl, thiazolyl, pyridinyl, cyclopentyl, cyclohexyl, pyridazinyl, —O-phenyl, —O-benzyl, phenyl, —(CH$_2$)-benzo[b]furanyl and benzyl group optionally may be substituted with 1, 2, 3, 4 or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl;
and the above-mentioned heterocycloaliphatic groups formed by R$^{11}$ and R$^{12}$, or by R$^{13}$ and R$^{14}$, optionally may contain 1, 2 or 3 additional heteroatoms independently selected from the group consisting of oxygen, nitrogen and sulfur as ring members;
the rings of the above-mentioned mono- or polycyclic ring systems optionally may be substituted with 1, 2, 3, 4 or 5 substituents independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —S(=O)$_2$—NH—C$_{1-5}$ alkyl, cyclohexyl, cyclopentyl, pyridinyl, pyridazinyl, —(CH$_2$)— benzo[b]furanyl, —O-phenyl, —O-benzyl, phenyl and benzyl;
  wherein the cyclic portion of a pyridinyl, cyclopentyl, cyclohexyl, pyridazinyl, —S(=O)$_2$ phenyl, —O-phenyl, —O-benzyl, phenyl, —(CH$_2$)-benzo[b]furanyl or benzyl group optionally may be substituted with 1, 2, 3, 4 or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl;
the rings of the above-mentioned mono- or polycyclic ring systems each have 5, 6 or 7 members and optionally may contain 1, 2, 3, 4 or 5 heteroatoms independently selected from the group consisting of oxygen, nitrogen and sulfur as ring members;
unless otherwise defined, the above-mentioned groups selected from the group consisting of phenyl, naphthyl (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl; 2H-benzo[1.4]oxazin-3(4H)-onyl, (3,4)-dihydroquinolin-2(1H)-onyl, [3,4]-dihydro-2H-1,4-benzoxazinyl and benzothiazolyl and aryl or heteroaryl groups optionally may be substituted with 1, 2, 3, 4 or 5 substituents independently selected from the group consisting of F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —N[S(=O)$_2$]—C$_{1-5}$—NH—S(=O)$_2$—C$_{1-5}$ alkylenephenyl, —NH—S(=O)$_2$—C$_{1-5}$ alkylenenaphthyl, —NH—S(=O)$_2$ phenyl, —NH—S(=O)$_2$ naphthyl, —S(=O)$_2$—NH—C$_{1-5}$ alkyl, cyclohexyl, cyclopentyl, piperidinyl, morpholinyl, pyrrolidinyl, pyridinyl, pyridazinyl, —(CH$_2$)-benzo[b]furanyl, —O-phenyl, —O-benzyl, phenyl and benzyl;
  wherein the cyclic portion of a pyridinyl, cyclopentyl, cyclohexyl, piperidinyl, morpholinyl, pyrrolidinyl, pyridazinyl, —S(=O)$_2$ phenyl, —O-phenyl, —O-benzyl, phenyl, —(CH$_2$)-benzo[b]furanyl, —NH—S(=O)$_2$—C$_{1-5}$ alkylenephenyl, —NH—S(=O)$_2$—C$_{1-5}$ alkylenenaphthyl, —NH—S(=O)$_2$ phenyl, —NH—S(=O)$_2$ naphthyl or benzyl group optionally may be substituted with 1, 2, 3, 4 or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl;
and
the above-mentioned heteroaryl groups optionally may contain 1, 2, 3, 4 or 5 heteroatoms independently selected from the group consisting of oxygen, nitrogen and sulfur as ring members.

6. A compound according to claim 1, wherein
R$^1$ denotes:
  a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl; wherein the group optionally may be substituted with 1, 2, 3, 4 or 5 substituents independently selected from the group consisting of F, Cl, Br, I, —CN, —NO$_2$, —OH, —SH and —NH$_2$; or a cyclic group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl; wherein the cyclic group optionally may be substituted with 1, 2, 3, 4 or 5 substituents independently selected from the group consisting of oxo (=O), thioxo (=S), F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)-β-CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, pyridinyl, pyridazinyl, —(CH$_2$)-benzo[b]furanyl, —O-phenyl, —O-benzyl, phenyl and benzyl;

wherein the cyclic portion of a pyridinyl, cyclopentyl, cyclohexyl, pyridazinyl, —S(=O)$_2$ phenyl, —O-phenyl, —O-benzyl, phenyl, —(CH$_2$)-benzo[b]furanyl or benzyl group optionally may be substituted with 1, 2, 3, 4 or 5 substituents independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl; or an aryl group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzotriazolyl, benzoxazolyl, benzisoxazolyl and benzothiazolyl; wherein the aryl group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, pyridinyl, pyridazinyl, —(CH$_2$)-benzo[b]furanyl, —O-phenyl, —O-benzyl, phenyl and benzyl;

wherein the cyclic portion of a pyridinyl, cyclopentyl, cyclohexyl, pyridazinyl, —S(=O)$_2$ phenyl, —O-phenyl, —O-benzyl, phenyl, —(CH$_2$)-benzo[b]furanyl or benzyl group optionally may be substituted with 1, 2, 3, 4 or 5 substituents independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl; or a —C(=O)—NR$^{11}$R$^{12}$ group; or
—(CHR$^{15}$)—R$^{18}$, (CHR$^{15}$)—(CHR$^{16}$)—R$^{18}$, —(CHR$^{15}$)—(CHR$^{16}$)—O—R$^{18}$, —(CHR$^{15}$)—(CHR$^{16}$)—(CHR$^{17}$)—R$^{18}$, —(CHR$^{15}$)—(CHR$^{16}$)—S—(CHR$^{17}$)—R$^{18}$ or —(CHR$^{15}$)—(CHR$^{16}$)—(CHR$^{17}$)—N(CH$_3$)—R$^{18}$;

and
R$^2$, R$^3$, R$^4$, R$^5$, R$^6$, R$^7$ and R$^8$ each independently denote hydrogen, or
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl.

7. A compound according to claim 1, wherein
R$^1$ and R$^3$ together denote a —(CH$_2$)$_p$ group, wherein p=3, 4, 5 or 6; and
R$^2$, R$^4$, R$^5$, R$^6$, R$^7$ and R$^8$ each independently denote hydrogen, or
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl.

8. A compound according to claim 1, wherein
R$^1$, R$^2$, R$^7$ and R$^8$ each denote hydrogen, and
R$^3$, R$^4$, R$^5$ and R$^6$ each independently denote a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl.

9. A compound according to claim 1, wherein
R$^9$ denotes hydrogen, or
a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl; or
an aryl group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzotriazolyl, benzoxazolyl, benzisoxazolyl and benzothiazolyl; wherein the aryl group optionally may be substituted with 1, 2, 3, 4 or 5 substituents independently selected from the group consisting of F, Cl, Br, I, —CN, —CF₃, —SF₅, —OH, —O—CH₃, —O—C₂H₅, —NH₂, —NO₂, —O—CF₃, —S—CF₃, —SH, —S—CH₃, —S—C₂H₅, methyl, ethyl, n-propyl, isopropyl, n-butyl, sec-butyl, isobutyl, tert-butyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)—C(CH₃)₃, —N(CH₃)₂, —N(C₂H₅)₂, —NH—CH₃, —NH—C₂H₅, —NH—C(=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—C(CH₃)₃, —C(=O)—NH₂, —C(=O)—NH—CH₃, —C(=O)—NH—C₂H₅, —C(=O)—N—(CH₃)₂, and —C(=O)—N—(C₂H₅)₂; or —(CHR¹⁹)—R²², —(CHR¹⁹)—(CHR²⁰)—R²², —(CHR¹⁹)—(CHR²⁰)—O—R²², —(CHR¹⁹)—(CHR²⁰)—(CHR²¹)—R²², —(CHR¹⁹)—(CHR²⁰)—S—(CHR²¹)—R²² or —(CHR¹⁹)—(CHR²⁰)—(CHR²¹)—N(CH₃)—R²².

10. A compound according to claim 1, wherein R¹⁰ denotes:

a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl; or an aryl group selected from the group consisting of phenyl, naphthyl, benzyl, phenethyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl and benzothiazolyl; wherein the cyclic portion of any of the above-mentioned aryl groups optionally may be substituted with 1, 2, 3, 4 or 5 substituents independently selected from the group consisting of F, Cl, Br, I, —CN, —CF₃, —SF₅, —OH, —O—CH₃, —O—C₂H₅, —NH₂, —NO₂, —O—CF₃, —S—CF₃, —SH, —S—CH₃, —S—C₂H₅, methyl, ethyl, n-propyl, isopropyl, n-butyl, sec-butyl, isobutyl, tert-butyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)—C(CH₃)₃, —N(CH₃)₂, —N(C₂H₅)₂, —NH—CH₃, —NH—C₂H₅, C(=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—C(CH₃)₃, —C(=O)—NH₂, —C(=O)—NH—CH₃, —C(=O)—NH—C₂H₅, —C(=O)—N—(CH₃)₂, —C(=O)—N—(C₂H₅)₂, —S(=O)₂—CH₃, —S(=O)₂—C₂H₅, —S(=O)₂ phenyl, —NH—S(=O)₂—CH₃, —NH—S(=O)₂—C₂H₅, —NH—S(=O)₂ phenyl, —S(=O)₂—NH—CH₃, —S(=O)₂—NH—C₂H₅, cyclohexyl, cyclopentyl, pyridinyl, pyridazinyl, —(CH₂)-benzo[b]furanyl, —O-phenyl, —O-benzyl, phenyl and benzyl;

wherein the cyclic portion of a pyridinyl, cyclopentyl, cyclohexyl, pyridazinyl, —S(=O)₂ phenyl, —NH—S(=O)₂ phenyl, —O-phenyl, —O-benzyl, phenyl, —(CH₂)— benzo[b]furanyl or benzyl group optionally may be substituted with 1, 2, 3, 4 or 5 substituents independently selected from the group consisting of F, Cl, Br, —OH, —CF₃, —SF5, —CN, —NO₂, methyl, ethyl, n-propyl, isopropyl, n-butyl, sec-butyl, isobutyl, tert-butyl, —O—CH₃, —O—C₂H₅, —O—CF₃, —S—CF₃, phenyl and —O-benzyl;

with the proviso that either of the two meta positions and the para position of a phenyl group are not both substituted with substituents which are respectively bound to the phenyl group via an identical atom selected from the group consisting of oxygen, sulfur and nitrogen; or a —C(=O)—NR¹³R¹⁴ group.

11. A compound according to claim 1, wherein R¹⁰ denotes:

a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl; or a phenyl group corresponding to formula XX

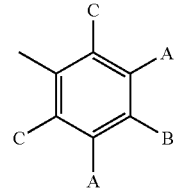

XX wherein the line denotes the bond of this phenyl group to the spiro compound of formula I; and A, B and C each independently denote a substituent selected from the group consisting of H, F, Cl, Br, I, —CN, —CF₃, —SF₅, —OH, —O—CH₃, —O—C₂H₅, —NH₂, —NO₂, —O—CF₃, —S—CF₃, —SH, —S—CH₃, —S—C₂H₅, methyl, ethyl, n-propyl, isopropyl, n-butyl, sec-butyl, isobutyl, tert-butyl, cyclohexyl, cyclopentyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)—C(CH₃)₃, —N(CH₃)₂, —N(C₂H₅)₂, —NH—CH₃, —NH—C₂H₅, —NH—C(=O)—O—CH₃, C(=O)—O—C₂H₅, —NH—C(=O)—O—C(CH₃)₃, —C(=O)—H, —C(=O)—CH₃, —C(=O)—C₂H₅, —C(=O)—C(CH₃)₃, —C(=O)—NH₂, —C(=O)—NH—CH₃, —C(=O)—NH—C₂H₅, —C(=O)—N—(CH₃)₂, —C(=O)—N—(C₂H₅)₂, —S(=O)₂—CH₃, —S(=O)₂—C₂H₅, —S(=O)₂ phenyl, —NH—S(=O)₂—CH₃, —NH—S(=O)₂—C₂H₅, —S(=O)₂—NH—CH₃, —S(=O)₂—NH—C₂H₅ and —NH—S(=O)₂ phenyl; with the proviso that either of the two positions A and position B of said phenyl group are not both substituted with substituents which are respectively bound to the phenyl group via an identical atom selected from the group consisting of oxygen, sulfur and nitrogen; or an aryl group selected from the group consisting of benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl, [3,4]-dihydro-2H-1,4-benzoxazinyl and benzothiazolyl; wherein the cyclic portion of any of the above-mentioned groups optionally may be substituted with 1, 2, 3, 4 or 5 substituents independently selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—$C(CH_3)_3$, —O—C(=O)—$CH_3$, —O—C(=O)—$C_2H_5$, —O—C(=O)—$C(CH_3)_3$, —$N(CH_3)_2$, —$N(C_2H_5)_2$, —NH—$CH_3$, —NH—$C_2H_5$, —NH—C(=O)—O—$CH_3$, —NH—C(=O)—O—$C_2H_5$, —NH—C(=O)—O—$C(CH_3)_3$, —C(=O)—H, —C(=O)—$CH_3$, —C(=O)—$C_2H_5$, —C(=O)—$C(CH_3)_3$, —C(=O)—$NH_2$, —C(=O)—NH—$CH_3$, —C(=O)—NH—$C_2H_5$, —C(=O)—N—$(CH_3)_2$, —C(=O)—N—$(C_2H_5)_2$, —S(=O)$_2$—$CH_3$, —S(=O)$_2$—$C_2H_5$, —S(=O)$_2$ phenyl, —NH—S(=O)$_2$—$CH_3$, —NH—S(=O)$_2$—$C_2H_5$, —S(=O)$_2$—NH—$CH_3$, —S(=O)$_2$—NH—$C_2H_5$, cyclohexyl, cyclopentyl, pyridinyl, pyridazinyl, —($CH_2$)-benzo[b]furanyl, —O-phenyl, —O-benzyl, phenyl and benzyl; wherein the cyclic portion of a pyridinyl, cyclopentyl, cyclohexyl, pyridazinyl, —S(=O)$_2$ phenyl, —O-phenyl, —O-benzyl, phenyl, —($CH_2$)-benzo[b]furanyl or benzyl group optionally may be substituted with 1, 2, 3, 4 or 5 substituents independently selected from the group consisting of F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—$CF_3$, —S—$CF_3$, phenyl and —O-benzyl; or a —C(=O)—$NR^{13}R^{14}$ group.

12. A compound according to claim 1, wherein $R^{11}$ and $R^{13}$ each independently denote:
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl; or
a cyclic group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl; wherein said cyclic group optionally may be bound via a —($CH_2$)— or —($CH_2$)$_2$— group; or
an aryl group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzotriazolyl, benzoxazolyl, benzisoxazolyl and benzothiazolyl;
wherein the aryl group optionally may be substituted with 1, 2, 3, 4 or 5 substituents independently selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—$C(CH_3)_3$, —O—C(=O)—$CH_3$, —O—C(=O)—$C_2H_5$, —O—C(=O)—$C(CH_3)_3$, —$N(CH_3)_2$, —$N(C_2H_5)_2$, —NH—$CH_3$, —NH—$C_2H_5$, —NH—C(=O)—O—$CH_3$, —NH—C(=O)—O—$C_2H_5$, —NH—C(=O)—O—$C(CH_3)_3$, —C(=O)—H, —C(=O)—$CH_3$, —C(=O)—$C_2H_5$, —C(=O)—$C(CH_3)_3$, —C(=O)—$NH_2$, —C(=O)—NH—$CH_3$, —C(=O)—NH—$C_2H_5$, —C(=O)—N—$(CH_3)_2$, —C(=O)—N—$(C_2H_5)_2$, —S(=O)$_2$—$CH_3$, —S(=O)$_2$—$C_2H_5$, —S(=O)$_2$ phenyl, —NH—S(=O)$_2$—$CH_3$, —NH—S(=O)$_2$—$C_2H_5$, —N[S(=O)$_2$—$CH_3$]$_2$, —N[S(=O)$_2$—$C_2H_5$]$_2$, —S(=O)$_2$—NH—$CH_3$, —S(=O)$_2$—NH—$C_2H_5$, cyclohexyl, cyclopentyl, piperidinyl, morpholinyl, pyrrolidinyl, pyridinyl, pyridazinyl, —($CH_2$)-benzo[b]furanyl, —O-phenyl, —O-benzyl, phenyl and benzyl;
wherein the cyclic portion of a pyridinyl, cyclopentyl, cyclohexyl, piperidinyl, morpholinyl, pyrrolidinyl, pyridazinyl, —S(=O)$_2$ phenyl, —O-phenyl, —O-benzyl, phenyl, —($CH_2$)-benzo[b]furanyl or benzyl group optionally may be substituted with 1, 2, 3, 4 or 5 substituents independently selected from the group consisting of F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—$CF_3$, —S—$CF_3$, phenyl and —O-benzyl;
and wherein the aryl group optionally may be bound via a —($CH_2$)— or —($CH_2$)$_2$— group.

13. A compound according to claim 1, wherein $R^{12}$ and $R^{14}$ each denote hydrogen.

14. A compound according to claim 1, wherein $R^{11}$ and $R^{12}$, or $R^{13}$ and $R^{14}$, together with the nitrogen atom to which they are bound form a cyclic moiety selected from the group consisting of pyrrolidinyl, piperidinyl, (1,3,4,5)-tetrahydropyrido[4,3-b]indolyl, (3,4)-dihydro-1H-isoquinolinyl, (1,3,4,9)-tetrahydro-[b]-carbolinyl, imidazolidinyl, (1,3)-thiazolidinyl, piperazinyl, morpholinyl, azepanyl, diazepanyl and thiomorpholinyl; wherein said cyclic moiety optionally may be substituted with 1, 2, 3, 4 or 5 substituents independently selected from the group consisting of oxo (=O), thioxo (=S), F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —$N(CH_3)_2$, —$N(C_2H_5)_2$, —NH—$CH_3$, —NH—$C_2H_5$, —NH—C(=O)—O—$C_2H_5$, —NH—C(=O)—O—$C(CH_3)_3$, —C(=O)—$NH_2$, —C(=O)—NH—$CH_3$, —C(=O)—NH—$C_2H_5$, —C(=O)—N—$(CH_3)_2$, —C(=O)—N—$(C_2H_5)_2$, cyclohexyl, cyclopentyl, pyridinyl, pyridazinyl, pyrimidinyl, [1,2,5]-thiadiazolyl, thiazolyl, —($CH_2$)-benzo[b]furanyl, —O-phenyl, —O-benzyl, phenyl and benzyl;
wherein the cyclic portion of a pyrimidinyl, [1,2,5]-thiadiazolyl, thiazolyl, pyridinyl, cyclopentyl, cyclohexyl, pyridazinyl, —O-phenyl, —O-benzyl, phenyl, —($CH_2$)-benzo[b]furanyl or benzyl group optionally may be substituted with 1, 2, 3, 4 or 5 substituents independently selected from the group consisting of F, Cl, Br, —OH, —CF$_3$, —SF$_5$, —CN, —NO$_2$, -methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl.

15. A compound according to claim 1, wherein $R^{15}$, $R^{16}$, $R^{17}$, $R^{19}$, $R^{20}$ and $R^{21}$ each independently denote hydrogen or a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl.

16. A compound according to claim 1, wherein $R^{18}$ and $R^{22}$ each independently denote:
- a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl; or
- a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzotriazolyl, benzoxazolyl, benzisoxazolyl and benzothiazolyl.

17. A compound according to claim 1, wherein n is 0 or 1.

18. A compound according to claim 1, wherein
n is 1;

I.)
$R^1$ denotes:
- a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl; or
- a cyclic group selected from the group consisting of cyclopropyl, cyclobutyl, cyclopentyl, cyclohexyl and cycloheptyl; or
- an aryl group selected from the group consisting of phenyl and naphthyl;
  wherein the aryl group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$ and —C(=O)—N—(C$_2$H$_5$)$_2$;
- a —C(=O)—NR$^{11}$R$^{12}$ group; or
- —(CHR$^{15}$)—R$^{18}$ or —(CHR$^{15}$)—(CHR$^{16}$)—R$^{18}$; and $R^2$, $R^3$, $R^4$, $R^5$, $R^6$, $R^7$ and $R^8$ each independently denote hydrogen or a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

or

II.)
$R^1$ and $R^3$ together denote a —(CH$_2$)$_p$ group wherein p=3 or 4; and
$R^2$, $R^4$, $R^5$, $R^6$, $R^7$ and $R^8$ each independently denote hydrogen or a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

or

III.)
$R^1$, $R^2$, $R^7$ and $R^8$ each denote hydrogen, and
$R^3$, $R^4$, $R^5$ and $R^6$ each independently denote a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;

and $R^9$ denotes hydrogen, or
- a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl; or
- an aryl group selected from the group consisting of phenyl and naphthyl;
  wherein said aryl group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)-β-C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$ and —C(=O)—N—(C$_2$H$_5$)$_2$;

or

—(CHR$^{19}$)—R$^{22}$ or —(CHR$^{19}$)—(CHR$^{20}$)—R$^{22}$;

$R^{10}$ denotes:
- a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl; or
- an aryl group selected from the group consisting of phenyl, naphthyl, benzyl, phenethyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl and benzothiazolyl;

wherein the aryl group optionally may be substituted with 1, 2, 3, 4 or 5 substituents independently selected from the group consisting of F, Cl, Br, I, —CN, —CF$_3$, —SF$_5$, —OH, —CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —NH—S(=O)$_2$ phenyl, —S(=O)$_2$—NH—CH$_3$, —S(=O)$_2$—NH—C$_2$H$_5$, cyclohexyl, cyclopentyl, pyridinyl, pyridazinyl, —(CH$_2$)-benzo[b]furanyl, —O-phenyl, —O-benzyl, phenyl and benzyl;

wherein the cyclic portion of a pyridinyl, cyclopentyl, cyclohexyl, pyridazinyl, —S(=O)$_2$ phenyl, —NH—S(=O)$_2$ phenyl, —O-phenyl, —O-benzyl, phenyl, —(CH$_2$)-benzo[b]furanyl or benzyl group optionally may be substituted with 1, 2, 3, 4 or 5 substituents independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl;

with the proviso that either of the two meta positions and the para position of this phenyl group are not both substituted with substituents which are respectively bound to the phenyl group via an identical atom selected from the group consisting of oxygen, sulfur and nitrogen; or a —C(=O)—NR$^{13}$R$^{14}$ group;

R$^{11}$ denotes a group selected from the group consisting of phenyl, naphthyl, indolyl, pyridinyl, (1,3)-benzodioxolyl and (1,4)-benzodioxanyl; wherein said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$, —NH—C$_2$H$_5$, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, piperidinyl, 4-methylpiperidinyl and phenyl; wherein a phenyl group optionally may be substituted with 1, 2 or 3 substituents selected from the group consisting of F, Cl and Br, and optionally may be bound via a —(CH$_2$) group or —(CH$_2$)$_2$— group;

R$^{13}$ denotes a group selected from the group consisting of phenyl, naphthyl, (1,3)-benzodioxolyl, (1,4)-benzodioxanyl, pyridinyl, quinazolinyl, quinoxalinyl, quinolinyl, isoquinolinyl, benzimidazolyl, benzotriazolyl, benzoxazolyl, benzisoxazolyl and benzothiazolyl; wherein said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —N[S(=O)$_2$—CH$_3$]$_2$, —N[S(=O)$_2$—C$_2$H$_5$]$_2$, —S(=O)$_2$—NH—CH$_3$ and —S(=O)$_2$—NH—C$_2$H$_5$, and said group optionally may be bound via a —(CH$_2$)— group or —(CH$_2$)$_2$— group;

R$^{12}$ and R$^{14}$ each denote hydrogen; or

R$^{11}$ and R$^{12}$, or R$^{13}$ and R$^{14}$, respectively, together with the nitrogen atom to which they are bound form a ring selected from the group consisting of pyrrolidinyl, piperidinyl, (1,3,4,5)-tetrahydropyrido[4,3-b]indolyl, (3,4)-dihydro-1H-isoquinolinyl, (1,3,4,9)-tetrahydro-[b]-carbolinyl, imidazolidinyl, (1,3)-thiazolidinyl, piperazinyl, morpholinyl, azepanyl, diazepanyl and thiomorpholinyl, wherein said ring optionally may be substituted with 1, 2, 3, 4 or 5 substituents independently selected from the group consisting of oxo(=O), thioxo (=S), F, Cl, Br, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$, pyridinyl, pyridazinyl, pyrimidinyl, [1,2,5]-thiadiazolyl, thiazolyl, phenyl and benzyl;

wherein the cyclic portion of a pyrimidinyl, [1,2,5]-thiadiazolyl, thiazolyl, pyridinyl, pyridazinyl, phenyl or benzyl group optionally may be substituted with 1, 2, 3, 4 or 5 substituents independently selected from the group consisting of F, Cl, Br, —OH, —CF$_3$, methyl, ethyl, n-propyl, isopropyl, n-butyl, sec-butyl, isobutyl, tert-butyl, —O—CH$_3$, —O—C$_2$H$_5$, —O—CF$_3$ and —S—CF$_3$;

R$^{15}$, R$^{16}$, R$^{19}$ and R$^{20}$ each denote hydrogen;

and

R$^{18}$ and R$^{22}$ each independently denote:

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl; or a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzotriazolyl, benzoxazolyl, benzisoxazolyl and benzothiazolyl.

19. A compound according to claim 1, wherein n is 1,

I.)

R$^1$ denotes:

a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl; or a group selected from the group consisting of cyclopropyl, cyclobutyl, cyclopentyl, cyclohexyl and cycloheptyl; or
a phenyl group; or
a —C(=O)—NR$^{11}$R$^{12}$ group;
$R^2$, $R^7$ and $R^8$ each denote hydrogen; and
$R^3$, $R^4$, $R^5$, $R^6$ each independently denote hydrogen, or
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
or
II.)
$R^1$ and $R^3$ together denote a —(CH$_2$)$_4$ group;
$R^2$, $R^4$, $R^7$ and $R^8$ each denote hydrogen; and
$R^5$ and $R^6$ each independently denote hydrogen, or
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
or
III.)
$R^1$, $R^2$, $R^7$ and $R^8$ each denote hydrogen, and
$R^3$, $R^4$, $R^5$ and $R^6$ each independently denote a methyl or ethyl group;
and
$R^9$ denotes hydrogen, or
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl; or
a phenyl group;
$R^{10}$ denotes:
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl; or
a phenyl group corresponding to formula XX

XX wherein
the line denotes the bond of this phenyl group to the Spiro compound of formula I; and
A, B and C each independently denote a substituent selected from the group consisting of H, F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, cyclohexyl, cyclopentyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$ and —NH—S(=O)$_2$ phenyl;
with the proviso that either of the two positions A and the position B of said phenyl group are not both substituted with substituents which are respectively bound to the phenyl group via an identical atom selected from the group consisting of oxygen, sulfur and nitrogen; or
a group selected from the group consisting of benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl, [3,4]-dihydro-2H-1,4-benzoxazinyl and benzothiazolyl; wherein the respective cyclic portion of the above-mentioned groups optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, pyridinyl, pyridazinyl, —(CH$_2$)— benzo[b]furanyl, —O-phenyl, —O-benzyl, phenyl and benzyl;
wherein the cyclic portion of a pyridinyl, cyclopentyl, cyclohexyl, pyridazinyl, —S(=O)$_2$ phenyl, —O-phenyl, —O-benzyl, phenyl, —(CH$_2$)— benzo[b]furanyl or benzyl group optionally may be substituted with 1, 2, 3, 4 or 5 substituents independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl; or
a —C(=O)—NR$^{13}$R$^{14}$ group;
$R^{11}$ denotes a group selected from the group consisting of phenyl, indolyl, (1,3)-benzodioxolyl, pyridinyl, (1,4)-benzodioxanyl and naphthyl; wherein the group optionally may be substituted with 1, 2, 3, 4 or 5 substituents independently selected from the group consisting of F, Cl, Br, —CF$_3$, —SF$_5$, —OH, —O—CH$_3$, —O—C$_2$H$_5$, —O—CF$_3$, phenyl, 3-chloro-4-fluorophenyl, 4-methylpiperidinyl, piperidinyl, methyl, ethyl, n-propyl, isopropyl, n-butyl, sec-butyl, isobutyl, tert-butyl, —NH—S(=O)$_2$—CH$_3$, —NH—S(=O)$_2$—C$_2$H$_5$, —S(=O)$_2$ —NH—CH$_3$ and —S(=O)$_2$—NH—C$_2$H$_5$, and optionally may be bound via a —(CH$_2$)— group;

R$^{13}$ denotes a group selected from the group consisting of phenyl, naphthyl, (1,3)-benzodioxolyl, (1,4)-benzodioxanyl, pyridinyl, quinolinyl and isoquinolinyl;

wherein the group optionally may be substituted with 1, 2, 3, 4 or 5 substituents independently selected from the group consisting of —SF$_5$, F, Cl, Br, —CF$_3$, —OH, —O—CH$_3$, —O—C$_2$H$_5$, —NH$_2$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$, —NH—C$_2$H$_5$, —NH—S(=O)$_2$—CH$_3$, —NH—S(=O)$_2$—C$_2$H$_5$, —N[S(=O)$_2$—CH$_3$]$_2$, —N[S(=O)$_2$—C$_2$H$_5$)]$_2$, —S(=O)$_2$—NH—CH$_3$ and —S(=O)$_2$—NH—C$_2$H$_5$, and optionally may be bound via a —(CH$_2$)— group;

R$^{12}$ and R$^{14}$ each denote hydrogen; or

R$^{11}$ and R$^{12}$, or R$^{13}$ and R$^{14}$, respectively, together with the nitrogen atom to which they are bound form a (3,4)-dihydro-1H-isoquinolinyl group which optionally may be substituted with 1, 2, 3, 4 or 5 substituents independently selected from the group consisting of —OH, —O—CH$_3$ and —O—C$_2$H$_5$; or a group selected from the group consisting of piperazinyl, 2-methylpiperazinyl, (2,6)-dimethylpiperazinyl and diazepanyl, wherein the group on a nitrogen atom can be respectively substituted with a substituent selected from the group consisting of pyridinyl, pyridazinyl, pyrimidinyl, [1,2,5]-thiadiazolyl, thiazolyl and phenyl; wherein the cyclic portion of a pyrimidinyl, [1,2,5]-thiadiazolyl, thiazolyl, pyridinyl, pyridazinyl or phenyl group optionally may be substituted with 1, 2, 3, 4 or 5 substituents independently selected from the group consisting of F, Cl, Br, —OH, —CF$_3$, methyl, ethyl, n-propyl, isopropyl, n-butyl, sec-butyl, isobutyl and tert-butyl.

20. A compound according to claim 1, wherein
n is equal to 1,

I.)
R$^1$ denotes:
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl; or
a cyclic group selected from the group consisting of cyclopropyl, cyclobutyl, cyclopentyl, cyclohexyl and cycloheptyl; or
a phenyl group; or
a —C(=O)—NR$^{11}$R$^{12}$ group
R$^2$, R$^7$ and R$^8$ each denote hydrogen; and
R$^3$, R$^4$, R$^5$, R$^6$ each independently denote hydrogen, or
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
or
R$^1$ and R$^3$ together denote a —(CH$_2$)$_4$— group;
R$^2$, R$^4$, R$^7$ and R$^8$ each denote hydrogen; and
R$^5$ and R$^6$ each independently denote hydrogen, or
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl;
or
III.)
R$^1$, R$^2$, R$^7$ and R$^8$ each denote hydrogen; and
R$^3$, R$^4$, R$^5$ and R$^6$ each independently denote a methyl or ethyl group;
and R$^9$ denotes hydrogen, or
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl; or
a phenyl group;

R$^{10}$ denotes:
a group selected from the group consisting of methyl, ethyl, n-propyl, isopropyl, n-butyl, sec-butyl, isobutyl, tert-butyl, (1,1)-dimethylpropyl, n-pentyl, sec-pentyl, n-hexyl and n-heptyl; or
a group selected from the group consisting of phenyl, 2-methanesulfonamidephenyl, 2-ethanesulfonamidephenyl, 2-trifluoromethylphenyl, 2-trifluoromethylsulfanylphenyl, 2-ethylphenyl, 2-tert-butylphenyl, 2-ethylaminosulfonylphenyl, 2-methylaminosulfonylphenyl, 2-bromophenyl, 2-chlorophenyl, 2-fluorophenyl, 2-methylphenyl, 2-trifluoromethoxyphenyl, 2-methoxyphenyl, 2-ethoxyphenyl, 2-propylphenyl, 2-iodophenyl, 3-chlorophenyl, 3-methylphenyl, 3-tert-butylphenyl, 3-trifluoromethylsulfanylphenyl, 3-trifluoromethylphenyl, 3-methanesulfonamidephenyl, 3-ethanesulfonamidephenyl, 3-fluorophenyl, 3-propylphenyl, 3-isopropylphenyl, 3-bromophenyl, 3-methoxyphenyl, 3-ethylphenyl, 3-ethylaminosulfonylphenyl, 3-methylaminosulfonylphenyl, 3-ethoxyphenyl, 3-trifluoromethoxyphenyl, 3-iodophenyl, 4-methylaminosulfonylphenyl, 4-ethylaminosulfonylphenyl, 4-methanesulfonamidephenyl, 4-ethanesulfonamidephenyl, 4-bromophenyl, 4-methoxyphenyl, 4-chlorophenyl, 4-fluorophenyl, 4-tert-butylphenyl, 4-trifluoromethylsulfanylphenyl, 4-methylphenyl, 4-isopropylphenyl, 4-trifluoromethylphenyl, 4-propylphenyl, 4-iodophenyl, 4-trifluoromethoxyphenyl, 4-ethylphenyl, 4-ethoxyphenyl, 2-fluoro-3-trifluoromethylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, (2,4)-dibromophenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, (3,4)-dichlorophenyl, 4-fluoro-3-trifluoromethylphenyl, 3-fluoro-4-trifluoromethylphenyl, (3,4)-difluorophenyl, 4-chloro-3-trifluoromethyl, 4-bromo-3-methylphenyl, 4-bromo-5-methylphenyl, 3-chloro-4-fluorophenyl, (3,4)-dibromophenyl, 4-chloro-3-methylphenyl, 4-bromo-3-methylphenyl, 4-fluoro-3-methylphenyl, (3,5)-dimethoxyphenyl, (3,5)-bis-trifluoromethylphenyl, (3,5)-difluorophenyl, (3,5)-dichlorophenyl, 3-fluoro-5-trifluoromethylphenyl, 5-fluoro-3-trifluoromethylphenyl, (3,5)-dibromophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methylphenyl, (2,4,5)-trifluorophenyl, (2,4,5)-trichlorophenyl, (2,4)-dichloro-5-fluorophenyl, (2,4, 6)-trichlorophenyl, (2,4,6)-trimethylphenyl, (2,4,6)-trifluorophenyl, (2,4,6)-trimethoxyphenyl, (2,3,4,5)-tetrafluorophenyl, 4-methoxy-2,3,6-trimethylphenyl, 4-methoxy-2,3,6-trimethylphenyl, 4-chloro-2,5-dimethylphenyl, 2-chloro-6-fluoro-3-methylphenyl, 6-chloro-2-fluoro-3-methyl, (2,3,4,5,6)-pentafluorophenyl, 3-fluoro-4-methylsulfonamidophenyl, 3-chloro-4-methylsulfonamidophenyl, 3-bromo-4-methylsulfonamidophenyl, 3-methoxy-4-methylsulfonamidophenyl, 3-hydroxy-4-methylsulfonamidophenyl, 3-trifluoromethyl-4-methylsulfonamidophenyl, 3-trifluoromethoxy-4-methylsulfonamidophenyl, 3-methyl-4-methylsulfonamidophenyl, 3-ethyl-4-methylsulfonamidophenyl, 3-isopropyl-4-methylsulfonamidophenyl, 3-propyl-4-methylsulfonamidophenyl, 3-tert-butyl-4-methylsulfonamidophenyl, 3-fluoro-4-phenylsulfonamidophenyl, 3-chloro-4-phenylsulfonamidophenyl, 3-bromo-4-phenylsulfonamidophenyl, 3-methoxy-4-phenylsulfonamidophenyl, 3-hydroxy-4-phenylsulfonamidophenyl, 3-trifluoromethyl-4-phenylsulfonamidophenyl, 3-trifluoromethoxy-4-phenylsulfonamidophenyl, 3-methyl-4-phenylsulfonamidophenyl, 3-ethyl-4-phenylsulfonamidophenyl, 3-isopropyl-4-phenylsulfonamidophenyl, 3-propyl-4-phenylsulfonamidophenyl, 3-tert-butyl-4-phenylsulfonamidophenyl, 4-fluoro-3-methylsulfonamidophenyl, 4-chloro-3-methylsulfonamidophenyl, 4-bromo-3-methylsulfonamidophenyl, 4-methoxy-3-methylsulfonamidophenyl, 4-hydroxy-3-methylsulfonamidophenyl, 4-trifluoromethyl-3-methylsulfonamidophenyl, 4-trifluoromethoxy-3-methylsulfonamidophenyl, 4-methyl-3-methylsulfonamidophenyl, 4-ethyl-3-methylsulfonamidophenyl, 4-isopropyl-3-methylsulfonamidophenyl, 4-propyl-3-methylsulfonamidophenyl, 4-tert-butyl-3-methylsulfonamidophenyl, 4-fluoro-3-phenylsulfonamidophenyl, 4-chloro-3-phenylsulfonamidophenyl, 4-bromo-3-phenylsulfonamidophenyl, 4-methoxy-3-phenylsulfonamidophenyl, 4-hydroxy-3-phenylsulfonamidophenyl, 4-trifluoromethyl-3-phenylsulfonamidophenyl, 4-trifluoromethoxy-3-phenylsulfonamidophenyl, 4-methyl-3-phenylsulfonamidophenyl, 4-ethyl-3-phenylsulfonamidophenyl, 4-isopropyl-3-phenylsulfonamidophenyl, 4-propyl-3-phenylsulfonamidophenyl and 4-tert-butyl-3-phenylsulfonamidophenyl; or a group selected from the group consisting of benzyl, phenethyl, thiazolyl, naphthyl, (1,3)-benzodioxolyl, (1,4)-benzodioxanyl and pyridinyl; wherein the cyclic portion of the above-mentioned groups optionally may be substituted with 1, 2, 3, 4 or 5 substituents independently selected from the group consisting of F, Cl, Br, I, —$CF_3$, —OH, —O—$CH_3$, —O—$C_2H_5$, methyl, ethyl, n-propyl, isopropyl, n-butyl, sec-butyl, isobutyl and tert-butyl; or a —C(=O)—$NR^{13}R^{14}$ group;

$R^{11}$ denotes a group selected from the group consisting of phenyl, indolyl, pyridinyl, (1,3)-benzodioxolyl, (1,4)-benzodioxanyl and naphthyl; wherein said group optionally may be substituted with 1, 2, 3, 4 or 5 substituents independently selected from the group consisting of F, Cl, Br, —$CF_3$, —$SF_5$, —OH, —O—$CH_3$, —O—$C_2H_5$, —O—$CF_3$, piperidinyl, 4-methylpiperidinyl, 3-chloro-4-fluorophenyl, methyl, ethyl, n-propyl, isopropyl, n-butyl, sec-butyl, isobutyl, tert-butyl, —NH—S(=O)$_2$—$CH_3$, —NH—S(=O)$_2$—$C_2H_5$, —S(=O)$_2$—NH—$CH_3$ and —S(=O)$_2$—NH—$C_2H_5$, and optionally may be bound via a —($CH_2$)— group;

$R^{13}$ denotes a group selected from the group consisting of phenyl, naphthyl, (1,3)-benzodioxolyl, (1,4)-benzodioxanyl, pyridinyl, quinolinyl and isoquinolinyl, wherein said group optionally may be substituted with 1, 2, 3, 4 or 5 substituents independently selected from the group consisting of —$SF_5$, F, Cl, Br, —$CF_3$, —OH, —O—$CH_3$, —O—$C_2H_5$, —$NH_2$, methyl, ethyl, n-propyl, isopropyl, n-butyl, sec-butyl, isobutyl, tert-butyl, —N($CH_3$)$_2$, —N($C_2H_5$)$_2$, —NH—$CH_3$, —NH—$C_2H_5$, —NH—S(=O)$_2$—$CH_3$, —NH—S(=O)$_2$—$C_2H_5$, —N[S(=O)$_2$—$CH_3$]$_2$, —N[S(=O)$_2$—$C_2H_5$]$_2$, —S(=O)$_2$—NH—$CH_3$ and —S(=O)$_2$—NH—$C_2H_5$, and optionally may be bound via a —($CH_2$)— group;

$R^{12}$ and $R^{14}$ each denote hydrogen; or $R^{11}$ and $R^{12}$, or $R^{13}$ and $R^{14}$, respectively, together with the nitrogen atom to which they are bound form:

a (3,4)-dihydro-1H-isoquinolinyl group which optionally may be substituted with 1, 2, 3, 4 or 5 substituents independently selected from the group consisting of —OH, —O—$CH_3$ and —O—$C_2H_5$; or a group selected from the group consisting of piperazinyl, 2-methylpiperazinyl, (2,6)-dimethylpiperazinyl and diazepanyl; wherein said group can be substituted at a nitrogen atom with a substituent selected from the group consisting of pyridinyl, pyridazinyl, pyrimidinyl, [1,2,5]-thiadiazolyl, thiazolyl and phenyl;

wherein the cyclic portion of a pyrimidinyl, [1,2,5]-thiadiazolyl, thiazolyl, pyridinyl, pyridazinyl or phenyl substitutent optionally may be substituted with 1, 2, 3, 4 or 5 substituents independently selected from the group consisting of F, Cl, Br, —OH, —$CF_3$, methyl, ethyl, n-propyl, isopropyl, n-butyl, sec-butyl, isobutyl and tert-butyl.

21. A compound according claim 1, selected from the group consisting of:

[1] 8-tert-butyl-1-oxa-2-azaspiro[4.5]dec-2-ene-3-carboxylic acid-4-aminobenzylamide

[2] trans-8-tert-butyl-1-oxa-2-azaspiro[4.5]dec-2-ene-3-carboxylic acid-4-methanesulfonylaminobenzylamide

[3] cis-8-tert-butyl-1-oxa-2-azaspiro[4.5]dec-2-ene-3-carboxylic acid-4-methanesulfonylaminobenzylamide

[4] 8-tert-butyl-1-oxa-2-azaspiro[4.5]dec-2-ene-3-carboxylic acid isoquinolin-5-ylamide

[5] trans-(8-tert-butyl-1-oxa-2-azaspiro[4.5] dec-2-en-3-yl)-(4-thiazol-2-ylpiperazin-1-yl)methanone

[6] cis-(8-tert-butyl-1-oxa-2-azaspiro[4.5]dec-2-en-3-yl)-(4-thiazol-2-ylpiperazin-1-yl)methanone

[7] cis-8-tert-butyl-1-oxa-2-azaspiro[4.5]dec-2-ene-3-carboxylic acid-3-fluoro-4-methanesulfonylaminobenzylamide

[8] trans-(8-tert-butyl-1-oxa-2-azaspiro[4.5]dec-2-en-3-yl)-[4-(3-trifluoromethylpyridin-2-yl)piperazin-1-yl] methanone

[9] cis-(8-tert-butyl-1-oxa-2-azaspiro[4.5]dec-2-en-3-yl)-[4-(3-trifluoromethylpyridin-2-yl)piperazin-1-yl] methanone

[10] trans-(8-tert-butyl-1-oxa-2-azaspiro[4.5]dec-2-en-3-yl)-[4-(4-hydroxyphenyl)piperazin-1-yl]methanone

[11] cis-(8-tert-butyl-1-oxa-2-azaspiro[4.5]dec-2-en-3-yl)-[4-(4-hydroxyphenyl)piperazin-1-yl]methanone

[12] (8-tert-butyl-1-oxa-2-azaspiro[4.5]dec-2-en-3-yl)-(6,7-dihydroxy-3,4-dihydro-1H-isoquinolin-2-yl)methanone

[13] cis-(8-tert-butyl-1-oxa-2-azaspiro[4.5]dec-2-en-3-yl)-[4-(6-methylpyridazin-3-yl)piperazin-1-yl]methanone
[14] trans-(8-tert-butyl-1-oxa-2-azaspiro[4.5]dec-2-en-3-yl)-[4-(6-methylpyridazin-3-yl)piperazin-1-yl]methanone
[15] cis-(8-tert-butyl-1-oxa-2-azaspiro[4.5]dec-2-en-3-yl)-(4-pyrimidin-2-ylpiperazin-1-yl)methanone
[16] trans-(8-tert-butyl-1-oxa-2-azaspiro[4.5]dec-2-en-3-yl)-(4-pyrimidin-2-ylpiperazin-1-yl)methanone
[17] cis-(8-tert-butyl-1-oxa-2-azaspiro[4.5]dec-2-en-3-yl)-[4-(4-chloro-[1,2,5]thiadiazol-3-yl)piperazin-1-yl]methanone
[18] trans-(8-tert-butyl-1-oxa-2-azaspiro[4.5]dec-2-en-3-yl)-(6,7-dimethoxy-3,4-dihydro-1H-isoquinolin-2-yl)methanone
[19] cis-(8-tert-butyl-1-oxa-2-azaspiro[4.5]dec-2-en-3-yl)-(6,7-dimethoxy-3,4-dihydro-1H-isoquinolin-2-yl)methanone
[20] trans-(8-tert-butyl-1-oxa-2-azaspiro[4.5]dec-2-en-3-yl)-[4-(4-chloro-[1,2,5]thiadiazol-3-yl)piperazin-1-yl]methanone
[21] trans-(8-tert-butyl-1-oxa-2-azaspiro[4.5]dec-2-en-3-yl)-[4-(3-chloropyridin-2-yl)-[1,4]diazepan-1-yl]methanone
[22] cis-(8-tert-butyl-1-oxa-2-azaspiro[4.5]dec-2-en-3-yl)-[4-(3-chloropyridin-2-yl)-[1,4]diazepan-1-yl]methanone
[23] trans-8-tert-butyl-1-oxa-2-azaspiro[4.5]dec-2-ene-3-carboxylic acid (pyridin-4-ylmethyl)amide
[24] cis-8-tert-butyl-1-oxa-2-azaspiro[4.5]dec-2-ene-3-carboxylic acid (pyridin-4-ylmethyl)amide
[25] trans-8-tert-butyl-1-oxa-2-azaspiro[4.5]dec-2-ene-3-carboxylic acid-3-fluoro-4-methanesulfonylaminobenzylamide
[26] trans-8-tert-butyl-1-oxa-2-azaspiro[4.5]dec-2-ene-3-carboxylic acid-4-hydroxy-3-methoxybenzylamide
[27] cis-8-tert-butyl-1-oxa-2-azaspiro[4.5] dec-2-ene-3-carboxylic acid-4-hydroxy-3-methoxybenzylamide
[28] trans-(8-tert-butyl-1-oxa-2-azaspiro[4.5]dec-2-en-3-yl)-[4-(3-chloropyridin-2-yl)piperazin-1-yl]methanone
[29] cis-(8-tert-butyl-1-oxa-2-azaspiro[4.5]dec-2-en-3-yl)-[4-(3-chloropyridin-2-yl)piperazin-1-yl]methanone
[30] 3',4',4a',5',6',7',8',8a'-octahydro-1'H,4H-spiro[isoxazol-5,2'-naphthalene]-3-carboxylic acid-(4-tert-butylphenyl)amide
[31] 3',4',4a',5',6',7',8',8a'-octahydro-1'H,4H-spiro[isoxazol-5,2'-naphthalene]-3-carboxylic acid-(4-tert-butylbenzyl)amide
[32] 3',4',4a',5',6',7',8',8a'-octahydro-1'H,4H-spiro[isoxazol-5,2'-naphthalene]-3-carboxylic acid-3-fluoro-4-methanesulfonylaminobenzylamide
[33] 3-methyl-1-oxa-2-azaspiro[4.5]dec-2-ene-8-carboxylic acid-(4-tert-butylphenyl)amide
[34] 3-phenyl-3',4',4a',5',6',7',8',8a'-octahydro-1'H,4H-spiro[isoxazol-5,2'-naphthalene]
[35] 3,8-diphenyl-1-oxa-2-azaspiro[4.5]dec-2-ene
[36] 8 phenyl-3-p-tolyl-1-oxa-2-azaspiro[4.5]dec-2-ene
[37] 8 phenyl-3-(4-trifluormethylphenyl)-1-oxa-2-azaspiro[4.5]dec-2-ene
[38] 7,7,9,9-tetramethyl-3-phenyl-1-oxa-2-azaspiro[4.5]dec-2-ene
[39] 3-(4-tert-butylphenyl)-8 phenyl-1-oxa-2-azaspiro[4.5]dec-2-ene
[40] 4-tert-butyl-3-phenyl-3',4',4a',5',6',7',8',8a'-octahydro-1'H,4H-spiro[isoxazol-5,2'-naphthalene]
[41] 3-(4-tert-butylphenyl)-7,7,9,9-tetramethyl-1-oxa-2-azaspiro[4.5]dec-2-ene
[42] 8 phenyl-3-pyridin-2-yl-1-oxa-2-azaspiro[4.5]dec-2-ene
[43] 8-(1,1-dimethylpropyl)-3-pyridin-2-yl-1-oxa-2-azaspiro[4.5]dec-2-ene
[44] 3-(4-tert-butylphenyl)-8-(1,1-dimethylpropyl)-1-oxa-2-azaspiro[4.5]dec-2-ene
[45] 3-(4-tert-butylphenyl)-8-ethyl-1-oxa-2-azaspiro[4.5]dec-2-ene
[46] cis-[3-(4-tert-butylphenyl)-1-oxa-2-azaspiro[4.5]dec-2-en-8-yl]-[4-(3-chloropyridin-2-yl)piperazin-1-yl]methanone
[47] trans-[3-(4-tert-butylphenyl)-1-oxa-2-azaspiro[4.5]dec-2-en-8-yl]-[4-(3-chloropyridin-2-yl)piperazin-1-yl]methanone
[48] cis-[4-(3-chloropyridin-2-yl)piperazin-1-yl]-(3-phenyl-1-oxa-2-azaspiro[4.5]dec-2-en-8-yl)methanone
[49] trans-[4-(3-chloropyridin-2-yl)piperazin-1-yl]-(3-phenyl-1-oxa-2-azaspiro[4.5]dec-2-en-8-yl)methanone
[50] 3-phenyl-1-oxa-2-azaspiro[4.5]dec-2-ene-8-carboxylic acid-(4-tert-butylphenyl)amide
[51] 3-phenyl-1-oxa-2-azaspiro[4.5]dec-2-ene-8-carboxylic acid-cis-(4-tert-butylphenyl)amide
[52] 3-phenyl-1-oxa-2-azaspiro[4.5]dec-2-ene-8-carboxylic acid-cis-3-fluoro-4-methanesulfonylaminobenzylamide
[53] 3-phenyl-1-oxa-2-azaspiro[4.5]dec-2-ene-8-carboxylic acid-trans-3-fluoro-4-methanesulfonylaminobenzylamide
[54] 8-tert-butyl-1-oxa-2-azaspiro[4.5]dec-2-ene-3-carboxylic acid-(4-tert-butyl phenyl)amide
[55] 3-phenyl-1-oxa-2-azaspiro[4.5]dec-2-ene-8-carboxylic acid-trans-(4-tert-butylphenyl)amide
[56] 8-tert-butyl-N-(4-(methylsulfonamido)benzyl)-1-oxa-2-azaspiro[4.5]dec-2-ene-3-carboxamide
[57] N-(4-tert-butylphenyl)-3-methyl-1-oxa-2-azaspiro[4.5]dec-2-ene-8-carboxamide hydrochloride
[58] ((5R,8R)-8-tert-butyl-1-oxa-2-azaspiro[4.5]dec-2-en-3-yl)(4-(3-chloropyridin-2-yl)-2,6-dimethylpiperazin-1-yl)methanone
[59] ((5S,8S)-8-tert-butyl-1-oxa-2-azaspiro[4.5]dec-2-en-3-yl)(4-(3-chloropyridin-2-yl)-2,6-dimethylpiperazin-1-yl)methanone
[60] ((5R,8R)-8-tert-butyl-1-oxa-2-azaspiro[4.5]dec-2-en-3-yl)(4-(3-chloropyridin-2-yl)-2-methylpiperazin-1-yl)methanone
[61] ((5S,8S)-8-tert-butyl-1-oxa-2-azaspiro[4.5]dec-2-en-3-yl)(4-(3-chloropyridin-2-yl)-2-methylpiperazin-1-yl)methanone
[62] (4-(3-chloropyridin-2-yl)piperazin-1-yl)(3-(3-methoxyphenyl)-1-oxa-2-azaspiro[4.5]dec-2-en-8-yl)methanone
[63] 3-(3-methoxyphenyl)-N-(4-(trifluormethoxy)benzyl)-1-oxa-2-azaspiro[4.5]dec-2-ene-8-carboxamide
[64] N-(1H-indol-5-yl)-3-(3-methoxyphenyl)-1-oxa-2-azaspiro[4.5]dec-2-ene-8-carboxamide
[65] N-(3-fluoro-4-(methylsulfonamido)benzyl)-3-(3-methoxyphenyl)-1-oxa-2-azaspiro[4.5]dec-2-ene-8-carboxamide
[66] N-(4-tert-butylphenyl)-3-(3-methoxyphenyl)-1-oxa-2-azaspiro[4.5]dec-2-ene-8-carboxamide
[67] N-(2,3-dihydrobenzo[b][1,4]dioxin-6-yl)-3-(3-methoxyphenyl)-1-oxa-2-azaspiro[4.5] dec-2-ene-8-carboxamide
[68] N-(4-tert-butylphenyl)-3-(4-fluorophenyl)-1-oxa-2-azaspiro[4.5]dec-2-ene-8-carboxamide

[69] (5R,8R)-3-phenyl-N-42-(piperidin-1-yl)-6-(trifluormethyl)pyridin-3-yl)methyl)-1-oxa-2-azaspiro[4.5]dec-2-ene-8-carboxamide

[70] (5R,8R)—N-((2-(4-methylpiperidin-1-yl)-6-(trifluormethyl)pyridin-3-yl)methyl)-3-phenyl-1-oxa-2-azaspiro[4.5]dec-2-ene-8-carboxamide

[71] (5S,8S)—N-((2-(3-chloro-4-fluorophenyl)-6-(trifluormethyl)pyridin-3-yl)methyl)-3-phenyl-1-oxa-2-azaspiro[4.5]dec-2-ene-8-carboxamide

[72] (5S,8S)—N-((2-(4-methylpiperidin-1-yl)-6-(trifluormethyl)pyridin-3-yl)methyl)-3-phenyl-1-oxa-2-azaspiro[4.5]dec-2-ene-8-carboxamide

[73] (5S,8S)-3-phenyl-N-((2-(piperidin-1-yl)-6-(trifluormethyl)pyridin-3-yl)methyl)-1-oxa-2-azaspiro[4.5]dec-2-ene-8-carboxamide

[74] (5R,8R)—N-(2,3-dihydrobenzo[b][1,4]dioxin-6-yl)-3-phenyl-1-oxa-2-azaspiro[4.5] dec-2-ene-8-carboxamide

[75] (5S,8S)—N-(2,3-dihydrobenzo[b][1,4]dioxin-6-yl)-3-phenyl-1-oxa-2-azaspiro[4.5] dec-2-ene-8-carboxamide

[79] 8-tert-butyl-N-(2,3-dihydrobenzo[b][1,4]dioxin-5-yl)-1-oxa-2-azaspiro[4.5]dec-2-ene-3-carboxamide

[80] N-(3-fluoro-4-(methylsulfonamido)benzyl)-8-tert-pentyl-1-oxa-2-azaspiro[4.5]dec-2-ene-3-carboxamide

[81] N-(2,3-dihydrobenzo[b][1,4]dioxin-5-yl)-8-tert-pentyl-1-oxa-2-azaspiro[4.5] dec-2-ene-3-carboxamide

[82] 8-cyclohexyl-N-(3-fluoro-4-(methylsulfonamido)benzyl)-1-oxa-2-azaspiro[4.5]dec-2-ene-3-carboxamide

[83] 8-tert-butyl-N-(7-hydroxynaphthalen-1-yl)-1-oxa-2-azaspiro[4.5]dec-2-ene-3-carboxamide

[84] N-(4-tert-butylphenyl)-3-(4-(3-chloropyridin-2-yl)piperazin-1-carbonyl)-1-oxa-2-azaspiro[4.5]dec-2-ene-8-carboxamide

[85] N-(4-tert-butylbenzyl)-3-(4-(3-chloropyridin-2-yl)piperazin-1-carbonyl)-1-oxa-2-azaspiro[4.5]dec-2-ene-8-carboxamide

[86] 8-tert-butyl-N-(5-hydroxynaphthalen-1-yl)-1-oxa-2-azaspiro[4.5]dec-2-ene-3-carboxamide

[87] 8-tert-butyl-N-(2-fluoro-5-(methylsulfonamido)phenyl)-1-oxa-2-azaspiro[4.5]dec-2-ene-3-carboxamide

[88] 8-tert-butyl-N-(2-fluoro-5-(N-(methylsulfonyl)methylsulfonamido)phenyl)-1-oxa-2-azaspiro[4.5]dec-2-ene-3-carboxamide

[89] 8-tert-butyl-N-(4-fluoro-3-(methylsulfonamido)phenyl)-1-oxa-2-azaspiro[4.5]dec-2-ene-3-carboxamide

[90] 8-tert-butyl-N-(3-fluoro-4-(methylsulfonamido)phenyl)-1-oxa-2-azaspiro[4.5]dec-2-ene-3-carboxamide

[91] 8-tert-butyl-N-(3-fluoro-4-(N-(methylsulfonyl)methylsulfonamido)phenyl)-1-oxa-2-azaspiro[4.5]dec-2-ene-3-carboxamide

[92] 8-tert-butyl-1-oxa-2-azaspiro[4.5]dec-2-ene-3-carboxylic acid-4-pentafluorosulfanylbenzylamide, and

[93] 3-(3-methoxyphenyl)-1-oxa-2-azaspiro[4.5]dec-2-ene-8-carboxylic acid-(4-pentafluorosulfanylphenyl) amide, or a salt or solvate thereof.

22. A method of preparing a compound corresponding to formula I according to claim 1, said process comprising:

reacting a compound corresponding to formula II

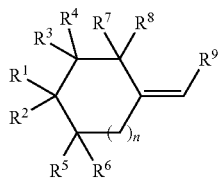

wherein n and $R^2$ to $R^9$ are as defined in claim 1, and $R^1$ is as defined in claim 1, with the exception of a —C(=O)—$NR^{11}R^{12}$ group, or denotes a —C(=O)—OR group; wherein R denotes a linear or branched $C_{1-6}$ alkyl group;

in a reaction medium in the presence of a base, with a compound corresponding to formula III

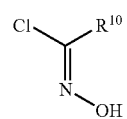

wherein $R^{10}$ has the meaning given in claim 1, with the exception of a —C(=O)—$NR^{13}R^{14}$ group, or denotes a —C(=O)—OR group; wherein R is as defined above, to obtain a product compound corresponding to formula IV

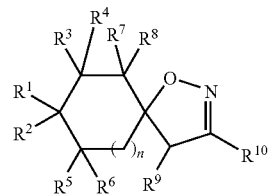

wherein n and $R^2$ to $R^9$ are as defined above, $R^1$ has the meaning given in claim 1, with the exception of a —C(=O)—$NR^{11}R^{12}$ group, or denotes a —C(=O)—OR group, and $R^{10}$ has the meaning given in claim 1, with the exception of a —C(=O)—$NR^{13}R^{14}$ group, or denotes a —C(=O)—OR group, wherein R in each case independently denotes a linear or branched $C_{1-6}$ alkyl group;

and optionally reacting a compound corresponding to formula IV, wherein n and $R^2$ to $R^9$ are as defined above, and $R^1$ denotes —C(=O)—OR, wherein R is as defined above, and $R^{10}$ has the meaning given in claim 1, with the exception of a —C(=O)—$NR^{13}R^{14}$ group, in a reaction medium in the presence of a base,
to obtain a product compound of corresponding to formula V,

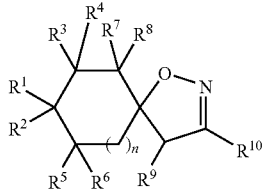

wherein n and $R^2$ to $R^9$ are as defined above, $R^1$ denotes —C(=O)—OH and $R^{10}$ has the meaning given in claim 1, with the exception of a —C(=O)—NR$^{13}$R$^{14}$ group;

and reacting a compound corresponding to formula V,
in a reaction medium in the presence of a coupling reagent,
and optionally in the presence of a base,
with a compound corresponding to the formula

HNR$^{11}$R$^{12}$ wherein $R^{11}$ and $R^{12}$ ahave the meanings given in claim 1, to obtain a product compound corresponding to formula I, wherein n and $R^2$ to $R^9$ are as defined above, $R^1$ denotes a —C(=O)—NR$^{11}$R$^{12}$ group, wherein $R^{11}$ and $R^{12}$ are as defined above, and $R^{10}$ has the meaning given in claim 1, with the exception of a —C(=O)—NR$^{13}$R$^{14}$ group;

or optionally reacting a compound corresponding to formula IV, wherein n and $R^2$ to $R^9$ are as defined above, $R^1$ has the meaning given in claim 1, with the exception of a —C(=O)—NR$^{11}$R$^{12}$ group, and $R^{10}$ denotes a —C(=O)—OR group; wherein R denotes a linear or branched $C_{1-6}$ alkyl group, in a reaction medium in the presence of a base,
to obtain a product compound corresponding to formula VI

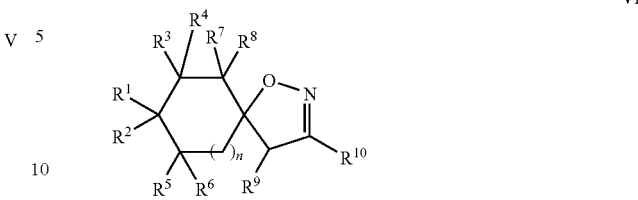

wherein n and $R^2$ to $R^9$ are as defined above, $R^1$ has the meaning given in claim 1, with the exception of a —C(=O)—NR$^{11}$R$^{12}$ group, and $R^{10}$ denotes —C(=O)—OH;

and reacting a compound of formula VI
in a reaction medium in the presence of a coupling reagent,
and optionally in the presence of a base, with a compound corresponding to the formula

HNR$^{13}$R$^{14}$ wherein $R^{13}$ and $R^{14}$ a have the meanings given in claim 1, to obtain a product compound of formula I, wherein n and $R^2$ to $R^9$ are as defined above, $R^1$ has the meaning given in claim 1, with the exception of a —C(=O)—NR$^{11}$R$^{12}$ group, or $R^1$ denotes a —C(=O)—NR$^{13}$R$^{14}$ group; wherein $R^{13}$ and $R^{14}$ are as defined above;

and optionally isolating or purifying any of the product compounds.

23. A pharmaceutical composition comprising a compound according to claim 1, and at least one physiologically compatible excipient.

24. A method of treating or inhibiting a disorder or disease state selected from the group consisting of pain, urinary incontinence and overactive bladder in a subject in need thereof, said method comprising administering to said subject a therapeutically effective amount of a compound corresponding to formula I according to claim 1.

25. A method according to claim 24, wherein said disorder or disease state is pain selected from the group consisting of acute pain, chronic pain and neuropathic pain.

* * * * *